(12) United States Patent
Barón et al.

(10) Patent No.: US 12,048,852 B2
(45) Date of Patent: Jul. 30, 2024

(54) DERMAL LIGHT DELIVERY DEVICE FOR LIGHT THERAPY

(71) Applicant: StimuSIL, Inc., Wilmington, DE (US)

(72) Inventors: Juan Mazzuchelli Barón, Madrid (ES); Ana Isabel Villalba Villar, Madrid (ES); Pablo Villalba Villar, Lisbon (PT); Guillermo Cantalapiedra Pro, Madrid (ES); Mehmet Alpaslan Kosoglu, Fairfax, VA (US)

(73) Assignee: StimuSIL, Inc., Wilmington, DE (US)

( * ) Notice: Subject to any disclaimer, the term of this patent is extended or adjusted under 35 U.S.C. 154(b) by 0 days.

(21) Appl. No.: 18/217,380

(22) Filed: Jun. 30, 2023

(65) Prior Publication Data
US 2024/0009478 A1 Jan. 11, 2024

Related U.S. Application Data

(60) Provisional application No. 63/358,450, filed on Jul. 5, 2022.

(51) Int. Cl.
*A61N 5/06* (2006.01)
(52) U.S. Cl.
CPC ......... *A61N 5/0601* (2013.01); *A61N 5/0617* (2013.01); *A61N 2005/0612* (2013.01); *A61N 2005/063* (2013.01); *A61N 2005/0632* (2013.01)
(58) Field of Classification Search
CPC ............... A61N 5/0601; A61N 5/0617; A61N 2005/0612; A61N 2005/063; A61N 2005/0632; A61N 5/06–2005/073; A61B 18/20–18/28
See application file for complete search history.

(56) References Cited

U.S. PATENT DOCUMENTS

| 4,564,011 A * | 1/1986 | Goldman | A61B 18/22 |
| | | | 606/17 |
| 6,355,054 B1 | 3/2002 | Neuberger | |
| 6,916,329 B1 * | 7/2005 | Zhao | A61N 1/0502 |
| | | | 606/189 |
| 8,798,722 B2 * | 8/2014 | Rylander | A61B 5/0059 |
| | | | 600/478 |
| 9,061,135 B1 * | 6/2015 | Keller | A61N 1/056 |
| 9,345,526 B2 * | 5/2016 | Elkins | A61M 37/0015 |

(Continued)

FOREIGN PATENT DOCUMENTS

KR 102151923 B1 9/2020

OTHER PUBLICATIONS

PCT International Search Report and Written Opinion in International Appln. No. PCT/US2023/069499, mailed on Feb. 7, 2024, 24 pages.

*Primary Examiner* — Jonathan T Kuo
(74) *Attorney, Agent, or Firm* — Fish & Richardson P.C.

(57) ABSTRACT

A light delivery device for delivering light therapy includes a light source configured to emit light, one or more first piercing members extending from a distal surface of the light delivery device, the one or more first piercing members being light-transmissive and being configured to be inserted into a subdermal or intradermal portion of the skin of the subject as the distal surface is placed against the skin of the subject. The one or more first piercing members are configured to, when inserted into the skin of the subject, deliver the light to the subdermal or intradermal portion of the skin of the subject.

30 Claims, 36 Drawing Sheets

(56) References Cited

U.S. PATENT DOCUMENTS

| | | | |
|---|---|---|---|
| 10,220,124 B2* | 3/2019 | Rylander | A61M 37/0015 |
| 10,363,080 B2* | 7/2019 | Elkins | A61M 37/0015 |
| 10,561,800 B2* | 2/2020 | Marlin | A61M 5/31571 |
| 11,185,688 B2* | 11/2021 | Hannaman | A61N 1/306 |
| 2008/0154247 A1 | 6/2008 | Dallarosa et al. | |
| 2011/0009737 A1 | 1/2011 | Manstein | |
| 2012/0065629 A1* | 3/2012 | Elkins | A61B 18/02 606/21 |
| 2012/0165682 A1 | 6/2012 | Keeney et al. | |
| 2012/0197357 A1 | 8/2012 | Dewey et al. | |
| 2013/0304163 A1* | 11/2013 | Moon | A61N 5/0617 607/88 |
| 2015/0094648 A1 | 4/2015 | Toyohara et al. | |
| 2017/0281877 A1* | 10/2017 | Marlin | A61M 5/3234 |
| 2018/0185624 A1 | 7/2018 | Ueno et al. | |
| 2018/0360527 A1* | 12/2018 | Boinagrov | A61B 90/361 |
| 2019/0030329 A1* | 1/2019 | Hannaman | A61M 5/46 |
| 2019/0046811 A1 | 2/2019 | Bean et al. | |
| 2020/0253813 A1 | 8/2020 | Kuhns | |
| 2020/0367961 A1* | 11/2020 | Podmore | A61N 5/0616 |
| 2023/0087102 A1 | 3/2023 | Xu et al. | |

* cited by examiner

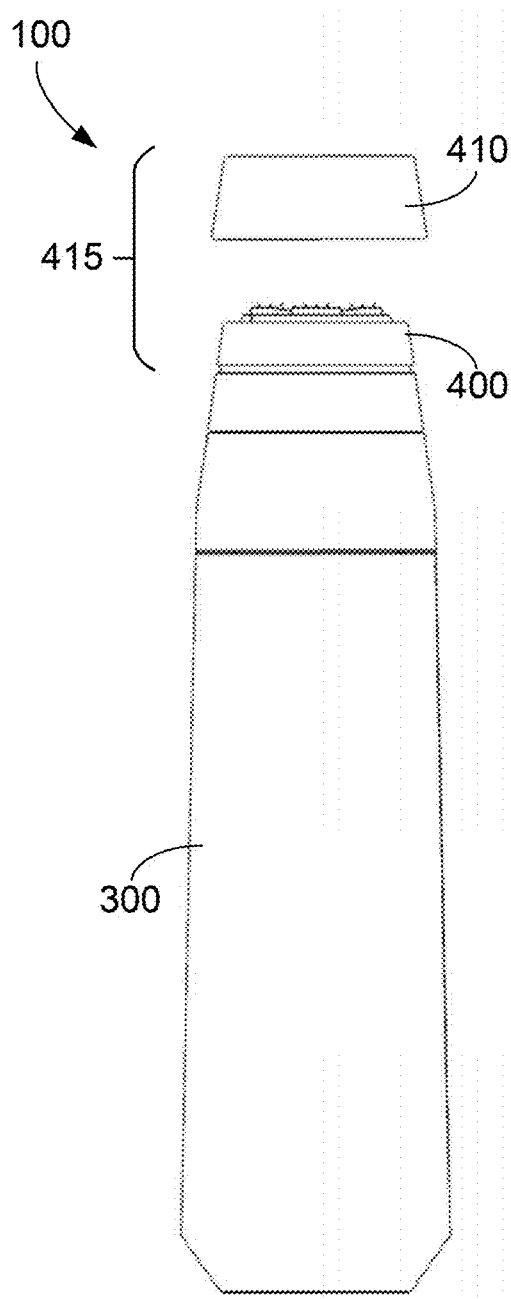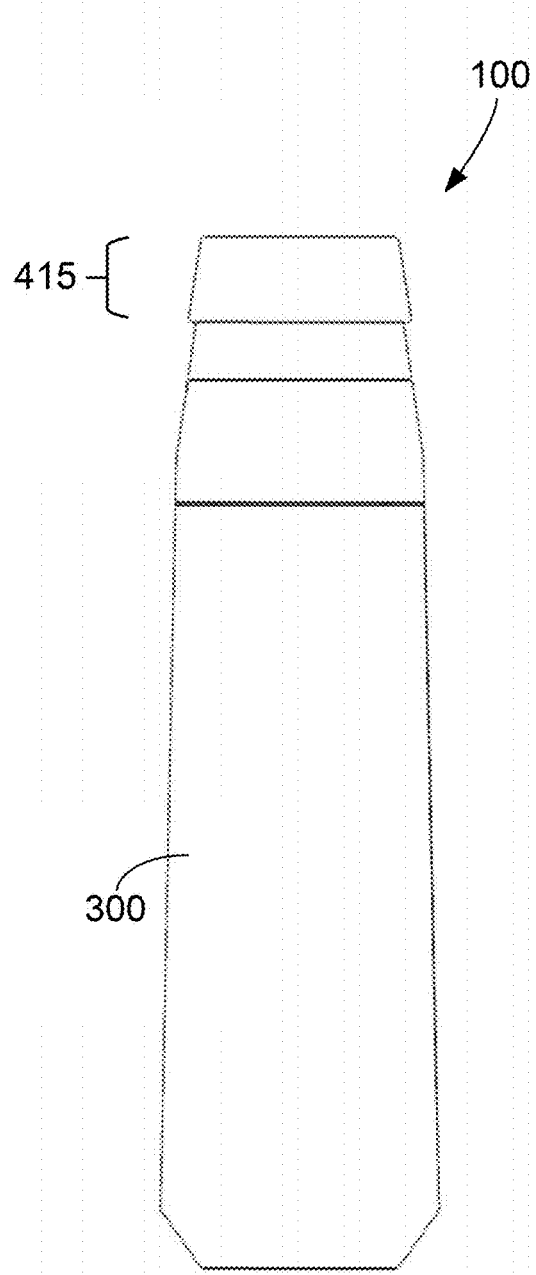
FIG. 4B  FIG. 4C

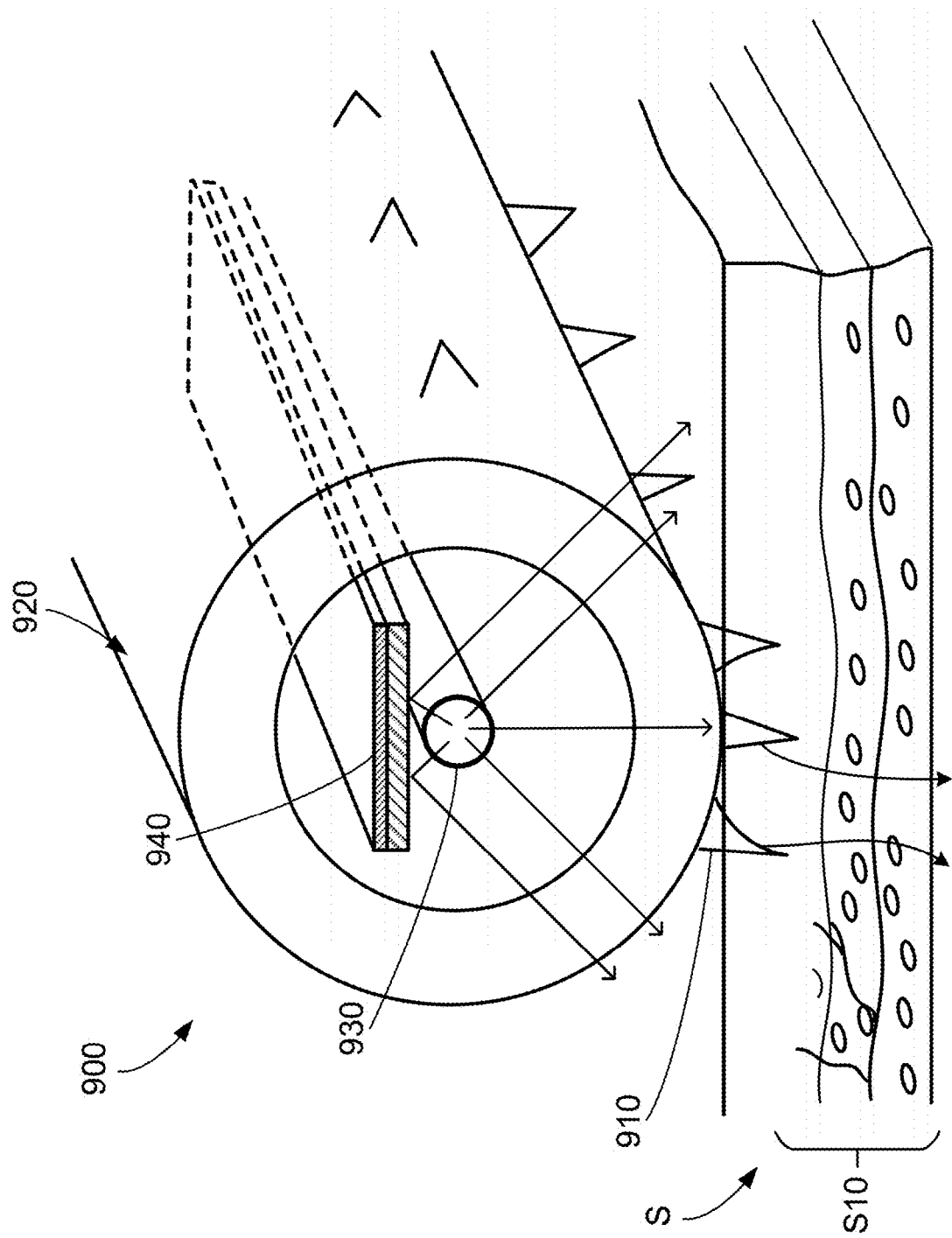

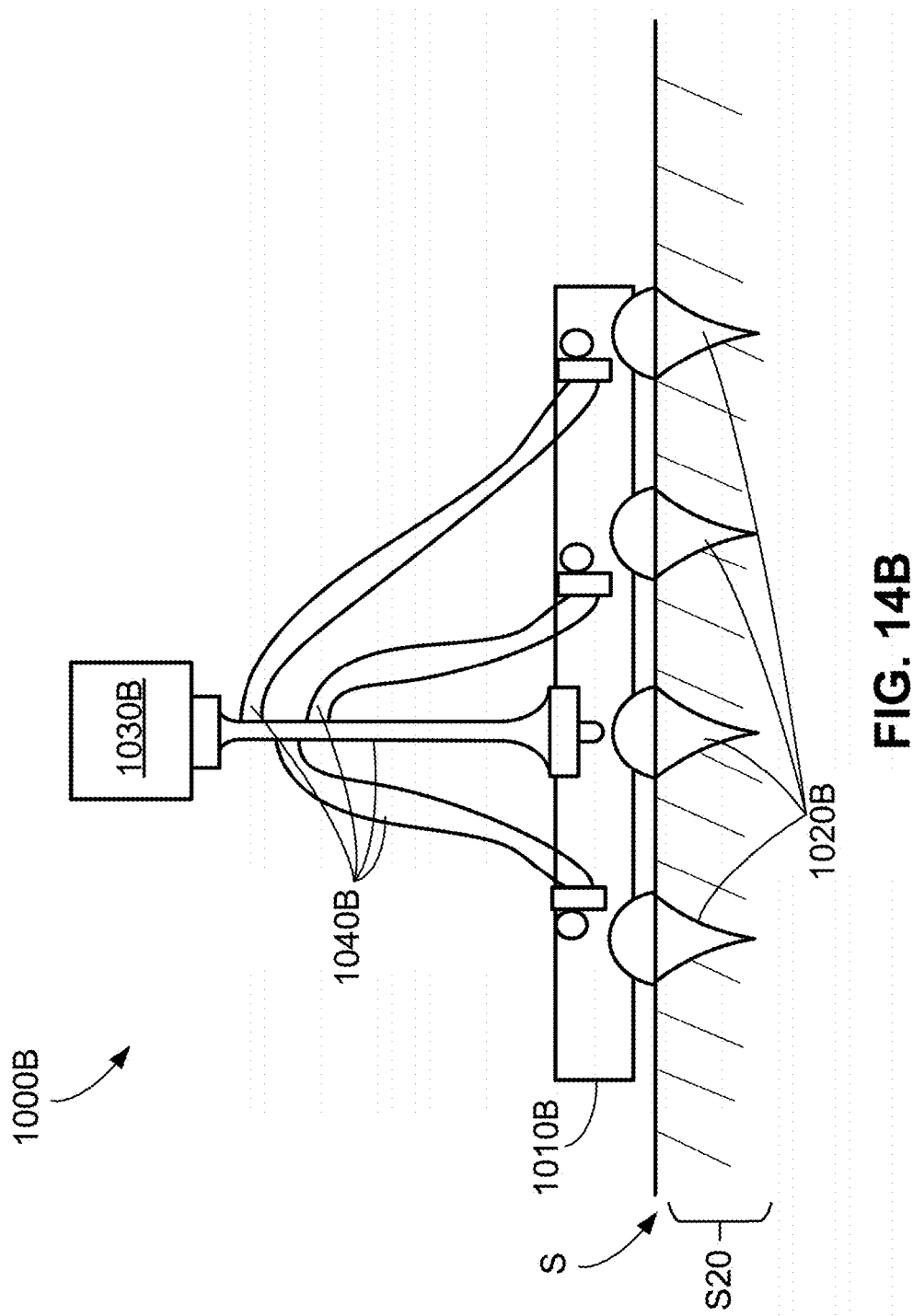

DERMAL LIGHT DELIVERY DEVICE FOR LIGHT THERAPY

TECHNICAL FIELD

This specification relates to a light delivery device for light therapy.

BACKGROUND

Light can be delivered to a biological surface, e.g., a surface of skin of a subject, in order to treat a condition. For example, phototherapy or light therapy is a medical therapy that involves using light to deliver a dose of light to a subject for treating a medical condition. Phototherapy can be used to provide aesthetic and dermatological treatments to a subject.

Photobiomodulation is a form of phototherapy that involves applying low levels of light to a biological surface for achieving a therapeutic or aesthetic outcome. For example, for stimulating hair growth, one method for photobiomodulation involves targeting a surface of the skin with a laser beam. With this approach, a significant portion of the energy in the laser beam is reflected and/or absorbed by the surface of the skin. As a result, to increase delivery of energy to a portion of the skin below the surface, e.g., the dermal level or the subdermal level, power can be increased, thereby increasing the risk of burning tissue.

SUMMARY

This disclosure features devices, methods, and systems that involve penetrating a surface of a biological surface, e.g., skin, of a subject with a needle and transmitting light through the needle to deliver the light to a subsurface depth. For example, an example device can include a needle that is inserted into skin of a subject, and a light source that is activated to emit light through the needle into a subdermal or intradermal portion of the skin of the subject. The needle can be an optical needle designed to allow delivery of light directly to the subdermal or intradermal layers. The device, when applied to the skin of the subject, can provide a therapeutic dose of light to the subdermal or intradermal portion of the skin and a therapeutic dose of mechanical damage to the skin, e.g., microdamage.

In one aspect, a light delivery device for delivering light therapy to skin of a subject is featured. The light delivery device includes a light source configured to emit light, one or more first piercing members extending from a distal surface of the light delivery device, the one or more first piercing members being light-transmissive and being configured to be inserted into a subdermal or intradermal portion of the skin of the subject as the distal surface is placed against the skin of the subject. The one or more first piercing members are configured to, when inserted into the skin of the subject, deliver the light to the subdermal or intradermal portion of the skin of the subject.

In another aspect, a system including a light delivery device and a charging system for the light delivery device is featured. The light delivery device that delivers light therapy to skin of a subject is featured. The light delivery device includes a light source configured to emit light, one or more first piercing members extending from a distal surface of the light delivery device, the one or more first piercing members being light-transmissive and being configured to be inserted into a subdermal or intradermal portion of the skin of the subject as the distal surface is placed against the skin of the subject. The one or more first piercing members are configured to, when inserted into the skin of the subject, deliver the light to the subdermal or intradermal portion of the skin of the subject.

In another aspect, a cartridge mountable to a light delivery device for delivering light therapy to skin of a subject is featured. The cartridge includes a housing mountable to the light delivery device. The cartridge includes one or more first piercing members attached to the housing, the one or more first piercing members extending from a distal surface of the cartridge, the one or more first piercing members being light-transmissive. The one or more first piercing members are configured to be inserted into a subdermal or intradermal portion of the skin of the subject as the cartridge is placed against the skin of the subject. The one or more first piercing members are configured to, when the cartridge is mounted to the light delivery device and when the one or more first piercing members are inserted into the skin of the subject, deliver light emitted by the light delivery device to the subdermal or intradermal portion of the skin of the subject.

In another aspect, a method of delivering light therapy to skin of a subject is featured. The method includes inserting a one or more first piercing members of a light delivery device into a subdermal or intradermal portion of the skin of the subject and initiating delivery of light through the one or more first piercing members to the subdermal or intradermal portion of the skin of the subject.

In another aspect, a method of aligning a light delivery device with a skin surface is featured. The method includes sensing a contact between a cartridge of the light delivery device with a skin surface, wherein the light delivery device comprises a handpiece coupled to the cartridge, the cartridge comprising a surface contact sensor and the handpiece comprising a display module, and measuring a capacitance between the cartridge and the surface using the surface contact sensor.

Implementations (e.g., of the devices, systems, cartridges, and methods described in this disclosure) can include one or more of the following features, each of which are combinable with one another to form further implementations.

In some implementations, the light delivery device further includes a cartridge including the one or more first piercing members. The cartridge can further include one or more second piercing members extending from a distal surface of the cartridge. The one or more second piercing members can be configured to be inserted into the subdermal or intradermal portion of the skin of the subject as the cartridge is placed against the skin of the subject.

In some implementations, the cartridge includes an outer casing, a core to which the one or more second piercing members are attached, and a needle holder to which the one or more first piercing members are attached, the needle holder configured to align the one or more first piercing members relative to the light emitted by the light source.

In some implementations, the light delivery device further includes an optical transmission system for transmitting the light emitted by the light source to the one or more first piercing members. The needle holder can be configured to align the one or more first piercing members relative to the light emitted by the light source. The needle holder can be configured to align the one or more first piercing members relative to the optical transmission system. In some implementations, the light source is spaced from the one or more first piercing members.

In some implementations, a width of the insertable portion of each piercing member of the one or more second piercing members is between 0.001 millimeters and 3 millimeters, and a width of the insertable portion of each piercing member of the one or more first piercing members is between 0.03 millimeters and 2 millimeters.

In some implementations, the width of the insertable portion of each piercing member of the one or more second piercing members is between 0.001 mm to 0.3 mm, and the width of the insertable portion of each piercing member of the one or more first piercing members is between 0.03 millimeters and 0.6 millimeters.

In some implementations, each piercing member of the one or more second piercing members is formed of a first material different from a second material of which each piercing member of the one or more first piercing members is formed.

In some implementations, the first material is a metal material, and the second material includes at least one of a polymer, ceramic, or glass material.

In some implementations, a quantity of the one or more second piercing members is between 1 and 100.

In some implementations, the quantity of the one or more second piercing members is between 10 and 50.

In some implementations, a quantity of the one or more second piercing members is at least 2 times a quantity of the one or more first piercing members.

In some implementations, the quantity of the one or more second piercing members is at least 3 times the quantity of the one or more first piercing members.

In some implementations, the one or more second piercing members are opaque to the light.

In some implementations, the light delivery device further includes an optical transmission system for transmitting the light emitted by the light source to the one or more first piercing members. The optical transmission system can include at least one optical element selected from the group consisting of: a fiber optic cable, a lens, a waveguide, or an optical diffuser.

In some implementations, the optical transmission system includes the lens, the lens being positioned between the light source and the one or more first piercing members. The lens can include a numerical aperture between 0.5 and 0.95.

In some implementations, the one or more first piercing members may include a lens.

In some implementations, the lens of the optical transmission system may be more than one lens.

In some implementations, a wavelength of the light emitted by the light source is between 280 nanometers and 3000 nanometers.

In some implementations, the light delivery device is configured such that a power of a portion of light delivered by each piercing member of the one or more first piercing members is at least 1 mW.

In some implementations, each piercing member of the one or more first piercing members is configured to be inserted to a depth of 0.001 to 3 millimeters relative to a surface of the skin.

In some implementations, each piercing member of the one or more first piercing members is configured to be inserted to a depth of at least 0.1 millimeters relative to a surface of the skin.

In some implementations, each piercing member of the one or more first piercing members protrudes beyond the distal surface of the light delivery device by a distance between 0.5 millimeters and 2.5 millimeters.

In some implementations, the distance is between 1 millimeter and 2 millimeters.

In some implementations, the one or more first piercing members are configured to, when inserted into the skin of the subject, deliver at least a portion of the light bypassing the melanin layer of the skin.

In some implementations, a surface of each piercing member of the one or more first piercing members is polished.

In some implementations, a quantity of the one or more first piercing members is between 1 and 50.

In some implementations, the quantity of the one or more first piercing members is between 1 and 10.

In some implementations, the light delivery device further includes one or more contact sensors configured to detect contact between the distal surface of the light delivery device and the skin of the subject.

In some implementations, the light delivery device includes the one or more contact sensors.

In some implementations, the one or more contact sensors includes at least three contact sensors configured to detect contact between the distal surface of the light delivery device and the skin.

In some implementations, the at least three contact sensors include three contact sensors configured to detect the contact between the distal surface of the light delivery device and the skin, the three contact sensors positioned to form a triangle.

In some implementations, the one or more contact sensors includes a capacitive sensor.

In some implementations, the light delivery device further includes a status indicator responsive to a signal generated by the one or more contact sensors.

In some implementations, the status indicator includes a visual display disposed on a proximal end of the device.

In some implementations, the status indicator communicates a direction for tilting the device to achieve a desired alignment.

In some implementations, the visual display comprises a first light, a second light, and a third light, wherein each of the first, second, and third lights of the visual display corresponds with a contact sensor.

In some implementations, the light source comprises a plurality of light sources corresponding to a number of first piercing members.

In some implementations, the light delivery device further includes a cartridge including the one or more first piercing members, and a handpiece assembly. The cartridge can be configured to be mounted to the handpiece assembly.

In some implementations, the light delivery device further includes a cartridge sensor configured to detect whether the cartridge is mounted to the handpiece assembly.

In some implementations, the light delivery device further includes one or more processors configured to prevent initiation of emission of the light by the light source in response to the cartridge sensor detect that the cartridge is not mounted to the handpiece assembly.

In some implementations, the light delivery device further includes a re-use prevention mechanism for preventing the cartridge from being coupled to the handpiece assembly after the cartridge is removed from the handpiece assembly.

In some implementations, the re-use prevention mechanism includes a breakable re-use prevention member configured to couple the cartridge to the handpiece assembly and configured to break in response to the cartridge being removed from the handpiece assembly.

In some implementations, the breakable re-use prevention member is positioned along an outer casing of the cartridge.

The breakable re-use prevention member can protrude inwardly from the outer casing of the cartridge.

In some implementations, the re-use prevention mechanism includes an electronically-readable tag on the cartridge, and an electronic reader on the handpiece assembly.

In some implementations, the light delivery device includes an electrical re-use prevention mechanism for preventing initiation of emission of the light by the light source, wherein the electrical re-use prevention mechanism comprises a cartridge memory, a cartridge unique identification (UID), and a UID reader.

In some implementations, the light delivery device includes a handpiece memory configured to store unique identifications of the cartridge coupled to the handpiece.

In some implementations, the light delivery device further includes a handpiece assembly. The one or more first piercing members can be integral to the handpiece assembly.

In some implementations, the light delivery device further includes an actuator to initiate emission of the light by the light source.

In some implementations, the light delivery device further includes a cartridge including the one or more first piercing members. The cartridge can include a conformable layer defining at least part of the distal surface of the cartridge.

In some implementations, the conformable layer is formed of a silicone or thermoplastic polyurethane.

In some implementations, the cartridge includes an electronically-readable tag configured to be read by a handpiece assembly to which the cartridge is attached and to prevent re-use of the cartridge.

In some implementations, the light delivered to the subdermal or intradermal portion of the skin of the subject is configured to promote hair growth and prevention of ingrown hair.

In some implementations, the light delivered to the skin of the subject is configured to treat subdermal fat tissue for aesthetic purposes such as reduction of circumference, fat dysmorphia or cellulite.

In some implementations, the light delivered to the skin of the subject is configured to treat a variety of dermatological conditions associated with cutis laxa, for example, turkey neck, dermatomegaly, dermatolysis, dermatocholosis, and chalazoderma.

In some implementations, the light delivered to the skin of the subject is configured to treat a variety of dermatological conditions associated with the appearance of the skin, for example, insufficient collagen production, rhytids, wrinkles, hypertrophic scars, keloids, and other forms of scarring.

In some implementations, the light delivered to the skin of the subject is configured to treat a variety of dermatological conditions associated with the melanin layer of the skin, for example, hypopigmenetation and hyperpigmentation disorders such as vitiligo, pityriasis versicolor, pityrasis alba, and nevus anemicus.

In some implementations, the light delivered to the skin of the subject is configured to treat a variety of dermatological conditions related to hair growth, for example, alopecia areata, chemotherapy-induced alopecia, seasonal hair shedding, treatment of silver, gray, and/or white hairs, restoring pigmentation to hair follicles, stress related hair loss, dandruff, dry or thinning skin, or other treatments or conditions related to hair loss and hair aging.

In some implementations, the light delivered to the skin of the subject is configured to improve short and long-term survival and growth of follicular grafts of hair transplantation.

In some implementations, the method of operating the light delivery device further includes inserting one or more second piercing members of the light delivery device into the subdermal or intradermal portion of the skin of the subject.

In some implementations, the method of operating the light delivery device further includes placing the light delivery device on the skin of the subject. Inserting the one or more second piercing members and inserting the one or more first piercing members of the cartridge can occur as the light delivery device is placed on the skin of the subject.

In some implementations, during the delivery of the light, a wavelength of the light is between 280 nanometers and 3000 nanometers.

In some implementations, during the delivery of the light, a power of a portion of light delivered by each piercing member of the one or more first piercing members is at least 1 mW.

In some implementations, inserting the one or more first piercing members of the light delivery device into the subdermal or intradermal portion of the skin of the subject includes inserting each piercing member of the one or more first piercing members to a depth of 0 to 3 millimeters relative to a surface of the skin.

In some implementations, inserting the one or more first piercing members of the light delivery device into the subdermal or intradermal portion of the skin of the subject includes inserting each piercing member of the one or more first piercing members to a depth of at least 0.1 millimeters relative to a surface of the skin.

In some implementations, the method of operating the light delivery device further includes detecting contact between the light delivery device and the skin of the subject. Initiating the delivery of the light through the one or more first piercing members to the subdermal or intradermal portion of the skin of the subject can include initiating the delivery of the light through the one or more first piercing members to the subdermal or intradermal portion of the skin of the subject after detecting the contact between the light delivery device and the skin of the subject.

In some implementations, the method of operating the light delivery device further includes attaching a cartridge to a handpiece assembly before inserting the one or more first piercing members into the subdermal or intradermal portion of the skin of the subject. The cartridge can include the one or more first piercing members. Initiating the delivery of the light through the one or more first piercing members to the subdermal or intradermal portion of the skin of the subject can include causing a light source of the handpiece assembly to deliver the light through the one or more first piercing members.

In some implementations, the method of operating the light delivery device further includes removing the cartridge from the handpiece assembly, and preventing use of the light delivery device with the cartridge after removing the cartridge from the handpiece assembly.

Advantages of the devices, systems, and methods described in this disclosure may include those described below and elsewhere in this disclosure.

In some implementations, the method of aligning a light delivery device with a skin surface includes sensing a contact between a cartridge of the light delivery device with a skin surface, wherein the light delivery device comprises a handpiece coupled to the cartridge, the cartridge comprising a surface contact sensor and the handpiece comprising a display module. The method also includes measuring a capacitance between the cartridge and the surface using the surface contact sensor. Measuring the capacitance can include measuring a first capacitance at a first contact area using a first surface contact sensor and a second capacitance at a second contact area using a second surface contact sensor.

In some implementations, the method of aligning a light delivery device with a skin surface includes processing the capacitance, determining a measured alignment of the light delivery device based on the measured capacitance, comparing the measured alignment with a designed alignment, and displaying, via the display module, a direction for tilting the light delivery device to achieve the desired alignment. Displaying the direction can include activating an LED ring of the display module, wherein the LED ring provides visual feedback to a user regarding the level of contact established between the skin and the cartridge.

In some implementations, the method of aligning a light delivery device with a skin surface includes detecting the cartridge is installed on the handpiece before the sensing, and reading, using a code reader of the handpiece, a unique identification of the cartridge.

In implementations for use with the skin, stimulation by light that targets physiological structures in epidermal, subdermal, and intradermal layers of skin (including the melanin layer) can have benefits in aesthetics, hair loss, skin rejuvenation, collagen induction, and in treating other medical and aesthetic conditions of a subject as described in this disclosure. The implementations described in this disclosure can allow for delivery of light that can more efficiently provide power to the target layer of tissue and can minimize losses of power due to intermediate layers of tissue and due to complex optical transmission systems. Furthermore, the devices, systems, and methods can be minimally invasive and can be applied safely and without injection of an anesthetic. Any punctures to the skin produced from penetration by the needles can heal relatively quickly, e.g., within hours, after treatment.

Because the devices, systems, and methods allow for light to be delivered to a subsurface portion of the skin, phototherapy treatment provided by the light can be more targeted and thereby have greater efficacy. Piercing members can serve a dual purpose of penetrating the surface of the skin and of serving as a conduit for light delivery to a subdermal or intradermal portion of the skin. In this way, the devices, systems, and methods can provide two modalities of therapy—microdamage and phototherapy—that can improve the overall efficacy of treatment of a condition.

The dimensions of the piercing members (e.g., width, length, and quantity), the amount of penetration of the piercing members, and the materials of the piercing members can be further selected to ensure an optimal range of microdamage and an optimal amount of light delivery. For example, the size and length of the piercing members can be designed to achieve a therapeutic amount of microdamage, and the exposed portions of the piercing members can be sized and dimensioned to achieve a therapeutic amount of light delivered to the subdermal or intradermal portion of the skin. Furthermore, the piercing members can be built with a material and geometry that minimizes energy losses for the delivered light, and the piercing members can provide a tip designed to concentrate the energy from the light and allow for the light to be dispersed in the subsurface layer in a radiating manner to more evenly distribute the light in the dermis.

In implementations of light delivery devices in which the piercing members form part of a replaceable cartridge for attaching to a handpiece assembly, the cartridge can improve the ease of use of the light delivery device. A user can easily remove a used cartridge from the handpiece assembly and attach a new cartridge to the handpiece assembly, thus obviating the need for complex sterilization procedures. Furthermore, replaceable cartridges can reduce the amount of general maintenance (e.g., inspection for damaged needles) that the user would need to perform.

Implementations including re-use prevention mechanisms can ensure that a user does not attempt to attach a used cartridge on a handpiece assembly, thus preventing cross-contamination between different subjects on which the light delivery device is used and preventing non-sterile use of a cartridge. Additionally, the re-use prevention mechanisms can prevent third-party and unofficial cartridges from being paired with the handpiece assembly. This can improve overall safety of the devices, systems, and methods described in this disclosure.

Optical transmission systems used for transmitting light from a light source to the piercing members can be configured to achieve a desired amount of energy of light delivered to the piercing needles. For example, lenses, diffusers, and other optical elements can be integrated into the optical transmission systems for achieving this desired amount of energy. Furthermore, activation of the light source can similarly be controlled—e.g., activated for an amount of time, activated to deliver a certain number of pulses, etc.—to ensure an optimal dose of light is delivered.

In implementations in which contact sensing or a contact sensor is used, the devices, systems, and methods can initiate delivery of light in a way that reduces the potential occurrence of user error and that promotes safe use. For example, the contact sensor can ensure that a user can only deliver light when the cartridge contacts the skin of the subject, thereby preventing the user from initiating delivery of light before light can be delivered to the subdermal or intradermal portion of the skin. This can avoid light being directed inadvertently at the eyes of a user or a subject, thus improving safety of the light delivery device. The contact sensor can be designed to detect that the cartridge stably contacts the surface of the skin.

The implementations described in this disclosure can involve a cartridge including a conformable layer that engages with a skin surface. The conformable layer can improve therapeutic outcomes by making it easier for a user to place the cartridge against the skin in a manner that ensures that the piercing members can penetrate the surface of the skin.

As used herein, the term "needle(s)" and "piercing member(s)" are used to describe an element that can pierce the skin. The needles and/or piercing members may be microneedles, singular, plural, disposable, reusable, flexible, rigid, with a variety of sizes and shapes, including cylindrical, tapered, and prismatic. Some needles and piercing members deliver light, and some may not. The examples described herein are not limited in this context.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

FIGS. 4A-4C are first exploded side, second exploded side, and unexploded side views, respectively, of an example of a light delivery device.

FIGS. 13B-13C are perspective and side views, respectively, of the example of the light delivery device of FIG. 13A being used on skin of a subject.

FIGS. 14A-14C and 15A-15B are schematic side views of examples of light delivery devices including patches to be affixed to a biological surface.

Like reference numbers and designations in the various drawings indicate like elements.

DETAILED DESCRIPTION

Examples of light delivery devices described in this disclosure aim to deliver mechanical damage and light energy into biological tissue, e.g., skin, to achieve a therapeutic effect or treatment. The delivery of mechanical damage can be achieved through various methods, including manual movement of a roller, manual pressing with a stamp, using a linear actuator with a cyclical reciprocating motion, using springs, hydraulic pneumatics, magnets, and the like, or other methods described in this disclosure.

The light delivery device can include a handpiece assembly, and light can be generated in the handpiece assembly using an appropriate light source (e.g., fiber laser, a diode, a laser diode, a light emitting diode, among other light sources described in this disclosure, and a combination thereof), including one or more light sources. The light can be transmitted to a distal end of the light delivery device via an optical transmission system. This optical transmission system can include an optical fiber, a waveguide, or a fiberoptic cable, or the light can be transmitted through free space. In some implementations, the light delivery device can include lenses, optical windows, mirrors, or other optical elements for directing the light toward the distal end of the light delivery device. In some implementations, light can be generated at or near the distal end of the light delivery device.

At the distal end of the device, the light can be delivered directly into the biological tissue at varying depths using a piercing member that is configured to puncture the biological tissue and that is at least partially optically transparent to allow delivery of the light. Special optics like light diffusers or lenses could be utilized to help distribute the light more evenly or to a larger area of the biological tissue.

Direct insertion of light transmitting microneedles into the skin can have the benefit of increasing the amount of energy delivered to a desired depth, e.g., the depth of a hair follicle root in implementations in which the light delivery device is used to promote hair growth and/or prevent or treat hair loss.

Example Light Delivery Device Systems

Figure 1A:
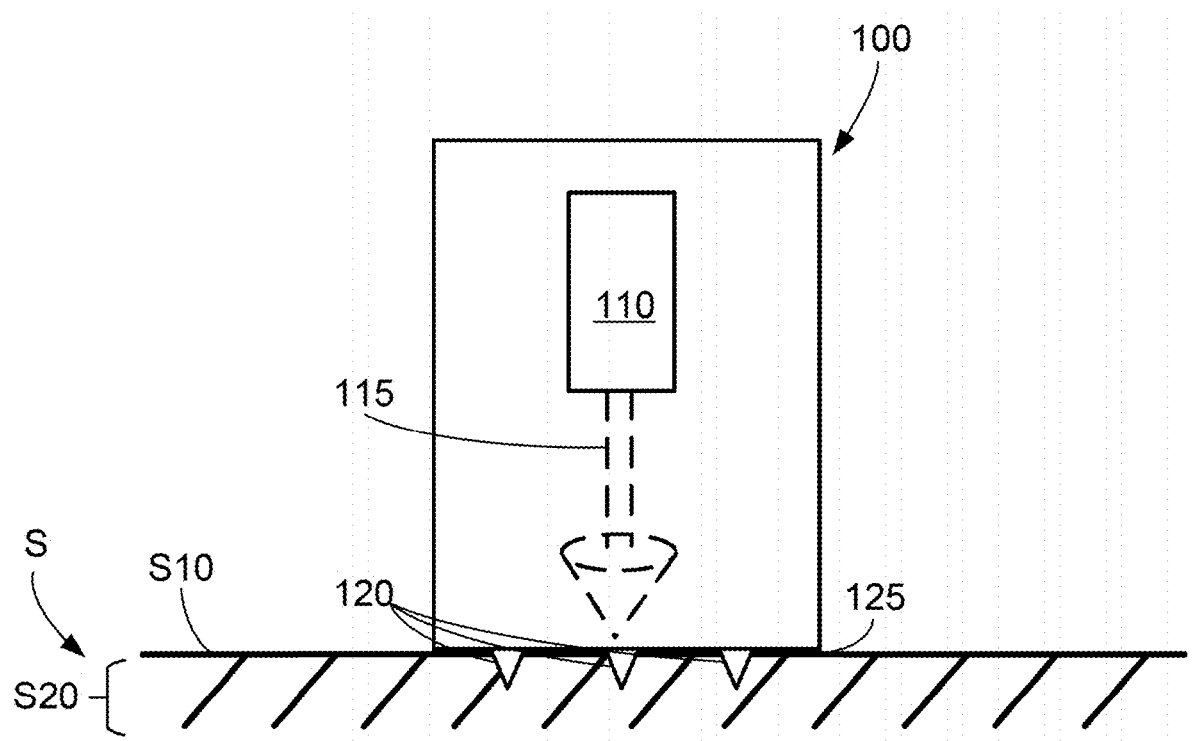
FIG. 1A is a schematic view of an example of a light delivery device.

FIG. 1A schematically illustrates an example of a light delivery device 100 for delivering light therapy to a biological tissue, e.g., skin S. The light delivery device 100 includes a light source 110 configured to emit light 115 and piercing members 120 extending from a distal surface 125 of the light delivery device 100. The light delivery device 100, e.g., the distal surface 125 of the light delivery device 100, is configured to be placed against a surface S10 of the skin S. The piercing members 120 are light-transmissive, thus allowing the light 115 to be transmitted through surfaces of the piercing members 120. In some examples, the light source 110 may be a plurality of similar or different light sources that can be combined into a single piercing member (e.g., needle) or multiple piercing members (e.g., needles).

The piercing members 120 are further configured to be inserted into a subdermal or intradermal portion S20 (including the melanin layer) of the skin S as the light delivery device 100 is placed against the skin S. When the piercing members 120 are inserted into the skin S, the piercing members 120 can deliver the light 115 by the light source 110 to the subdermal or intradermal portion S20 (including the melanin layer) of the skin S.

Figure 1B:
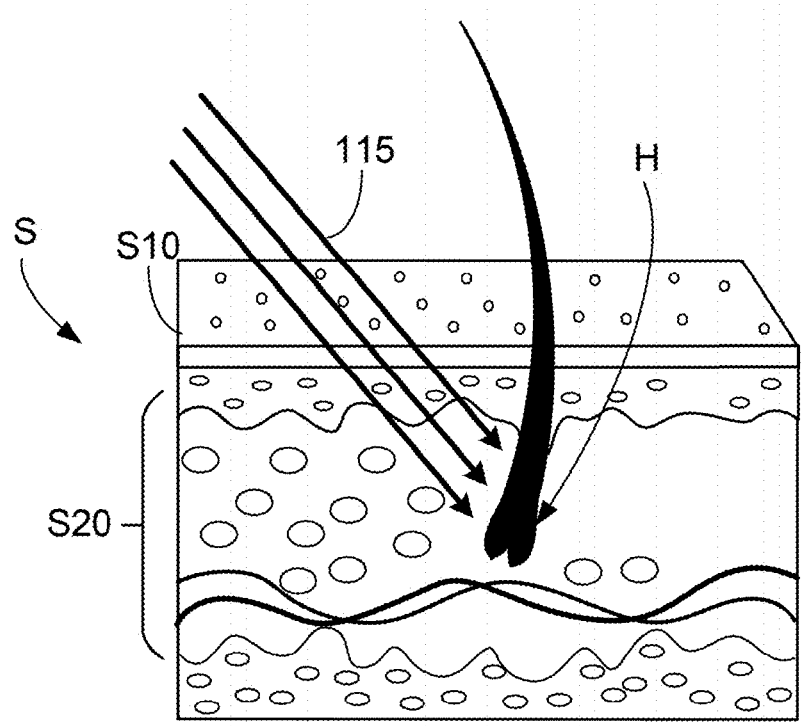
FIG. 1B is a schematic illustration of light delivered to skin of a subject.

Examples configurations of the light delivery device 100 and systems and methods associated with the light delivery device 100 are provided in this disclosure. By enabling delivery of light to the subdermal or intradermal portion S20 (including the melanin layer) of the skin S, these example configurations of the light delivery device 100 allow more targeted delivery of the light 115 to a subsurface layer of tissue, e.g., in the subdermal or intradermal portion S20 (including the melanin layer) of the skin S, as shown in FIG. 1B. This can thus improve therapeutic outcomes. Indeed, in the example shown in FIG. 1B, as compared to examples in which light is delivered at a surface of skin, the light 115 is shown as being delivered to a portion of the tissue closer to the target layer of tissue associated with a hair follicle H. Such implementations can more effectively achieve the therapeutic effect of stimulating hair growth.

Figure 2A:
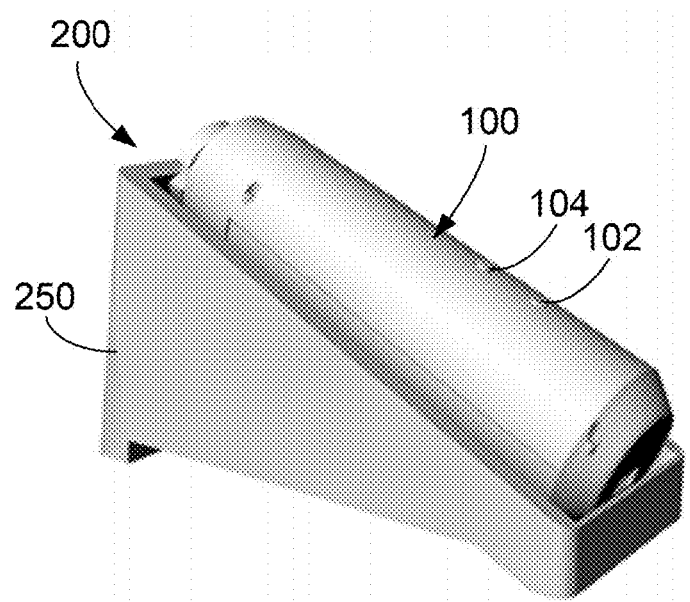
FIGS. 2A-2B are perspective views of an example of at least a portion of a light delivery device, with FIG. 2A showing a handpiece assembly of the light delivery device connected to a charging system, and FIG. 2B showing the handpiece assembly of the light delivery device disconnected from the charging system.
Figure 2B:
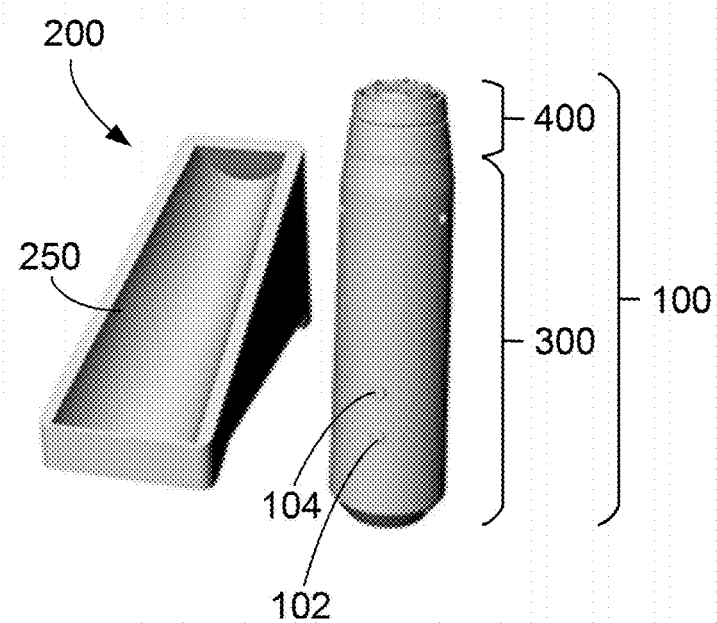

FIGS. 2A-2B illustrate an example of a system 200 including the light delivery device 100 and a charging station 250. The light delivery device 100 includes a handpiece assembly 300 and a cartridge 400 attached to the handpiece assembly 300. In some implementations, the cartridge 400 is integral to the handpiece assembly 300. In other implementations, the cartridge 400 is removably attached to the handpiece assembly 300. For example, the cartridge 400 can be single-use, while the handpiece assembly 300 can be multi-use. In particular, the handpiece assembly 300 can be reusable and rechargable. In some examples, the handpiece assembly 300 may be electrically coupled to a power source. As described in greater detail elsewhere in this disclosure, the cartridge 400 can include the piercing members 120 (shown in FIG. 1A) of the light delivery device 100. Additionally, as described further below, the handpiece assembly 300 may include a one-use security measure to prevent a used cartridge from being used multiple times.

In examples in which the handpiece assembly 300 is multi-use, the light delivery device 100 can be charged using the charging station 250. The charging station 250 can be plugged into an outlet, e.g., an AC standard outlet, and the handpiece assembly 300 can be connected to the charging station 250 to store and charge the handpiece assembly 300. For example, the handpiece assembly 300 can include an energy storage device 140 (shown in FIG. 3A), e.g., a battery, that is rechargeable. The energy storage device 140 is configured to be recharged when the handpiece assembly 300 is connected to the charging station 250 (FIG. 2A).

The light delivery device 100 can be removed from the charging station 250 in order to be used for providing treatment (FIG. 2B). The light delivery device 100 can include one or more actuators (e.g., buttons, switches, or other actuators) for operating the light delivery device 100. For example, a button 102 can be used for turning on and turning off the light delivery device 100, and an actuator (e.g., a mechanical button 104, a capacitive button, or a potentiometer) can be used for activating a light source (described elsewhere in this disclosure) for delivering light therapy. In some implementations, the light delivery device 100 can include a control system 500 or 500A (shown in FIGS. 3A and 3B) (e.g., including one or more processors) responsive to operation of the one or more buttons for controlling the light delivery device 100.

Example Control Systems

Figure 3A:
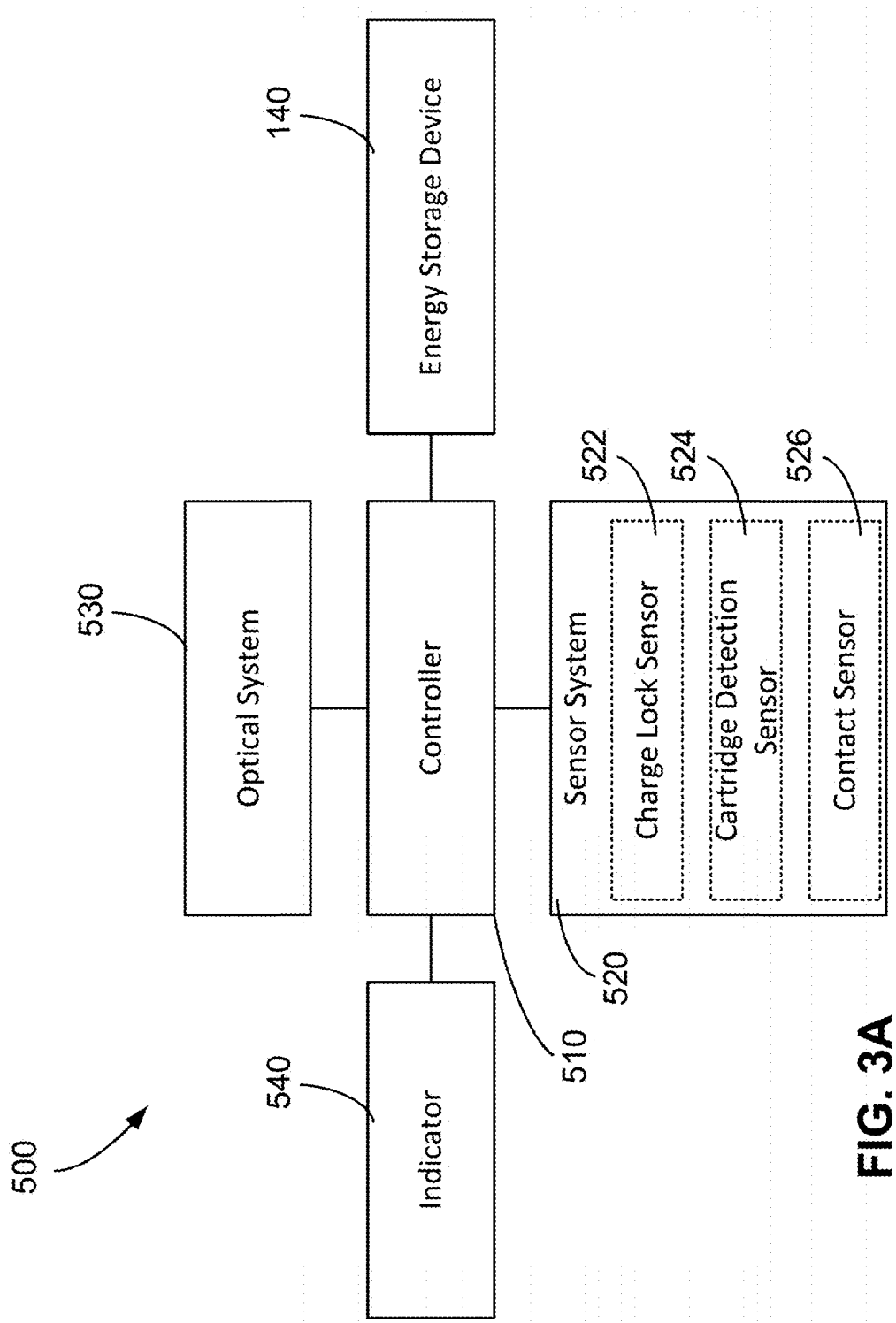
FIG. 3A is a block diagram of an example of a control system for a light delivery device.

FIG. 3A illustrates an example of the control system 500 for the light delivery device 100. The control system 500 can include the energy storage device 140, a controller 510, a sensor system 520, an optical system 530, and an indicator 540.

The optical system 530 includes the light source of the light delivery device 100 and an optical transmission system (described elsewhere in this disclosure) for receiving and directing light emitted by the light source. The indicator 540 is a status indicator and can include one or more tactile indicator devices (e.g., a vibration unit), audible indicator devices (e.g., a speaker), or visual indicator devices (e.g., an indicator light) for providing alerts or notifications to a user indicative of a status of the light delivery device 100.

The controller 510 includes one or more processors for controlling operations of the control system 500. For example, the controller 510 can respond to a signal generated by the one or more buttons of the light delivery device 100 by generating a control signal for controlling the energy storage device 140 (e.g., to ensure safe use of the energy storage device 140), the sensor system 520, the optical system 530, and/or the indicator 540.

The sensor system 520 includes sensors configured to generate signals received by the controller 510. The sensor system 520 can include, for example, the buttons 102, 104. The sensor system 520 can further include a charge lock sensor 522 to prevent the light source of the optical system 530 from being activated under certain conditions. The charge lock sensor 522, for example, can detect when the light delivery device 100 is being charged (e.g., by the charging station 250). In response to the charge lock sensor 522 detecting that the light delivery device 100 is being charged, the controller 510 can prevent operation of the optical system 530 (e.g., prevent operation of the light source of the optical system 530).

In implementations in which the light delivery device 100 includes a cartridge 400, the sensor system 520 can further include a cartridge detection sensor 524 for detecting whether a cartridge is attached to the handpiece assembly 300 of the light delivery device 100. The controller 510 can be configured to allow operation of the optical system (e.g., allow operation of the light source of the optical system 530) only when the cartridge detection sensor 524 detects that the cartridge 400 is attached to the handpiece assembly 300. For example, the controller 510 can be configured to prevent initiation of emission of the light by the light source in response to the cartridge detection sensor 524 detecting that the cartridge is not mounted to the handpiece assembly 300. In some implementations, the cartridge detection sensor 524 includes firmware (e.g., mediated by the controller 510) to prevent initiation of emission of the light and/or hardware (e.g., an analog circuit) to prevent initiation of emission of the light. Further, as described below, the cartridge detection sensor 524 or other sensor can detect whether a used cartridge 400 is being reattached to the handpiece assembly 300. If the cartridge detector sensor 524 reads a unique identifier on the used cartridge 400, the controller 510 can prevent initiation of emission of the light by the light source.

The sensor system 520 can further include a contact sensor device 526 for detecting when the distal surface 125 of the light delivery device 100 (e.g., a distal surface of the cartridge 400) contacts a biological surface, e.g., a surface of skin of the subject. The controller 510 can be configured to allow operation of the optical system (e.g., allow operation of the light source of the optical system 530) only when the contact sensor device 526 detects contact with the biological surface. Examples of the contact sensor device 526 are described elsewhere in this disclosure. In one example, the contact sensor device 526 has a triangulated sensor mechanism that can sense when the distal surface of the cartridge 400 contacts and is properly aligned with the biological surface. The handpiece assembly 300 has a feedback mechanism that relays information to the user that the device is aligned or not aligned. If the device is not aligned, the handpiece assembly 300 indicates (by audio or visual input) in which direction the user should tilt the handpiece assembly 300 to align the device with the biological surface.

Figure 3B:
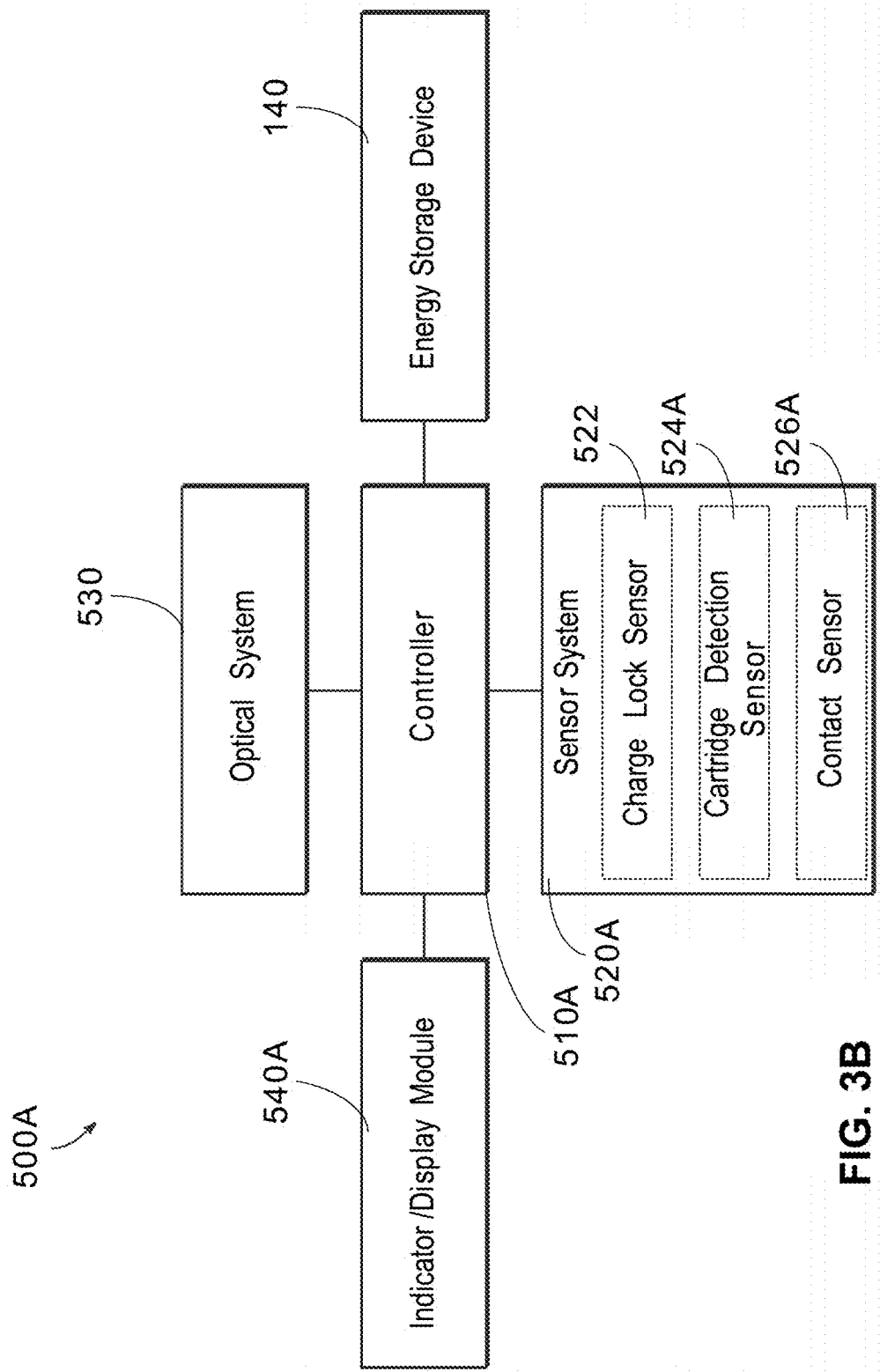
FIG. 3B is a block diagram of a different example of a control system for a light delivery device.

FIG. 3B illustrates another example of a control system 500A for the light delivery device 100. The control system 500A can include the energy storage device 140, a controller 510, and an optical system 530, as well as a different sensor system 520A and display module 540A. The control system 500A is similar to the control system 500 of FIG. 3A, but may be used to operate a different re-use prevention mechanism described herein using one or more contact sensors 527A of FIGS. 10B-10G. The sensor system 520A of the control system 500A may also include and operate the device 100 using the charge lock sensor 522 and cartridge detection sensor 526A.

It will be appreciated that many of the functions of the control system 500 described herein and with respect to the device 100 may be equally or similarly applied to the functions of the control system 500A with respect to the device 100A and other embodiments of the disclosure.

Example Handpiece Assemblies

Figure 4A:
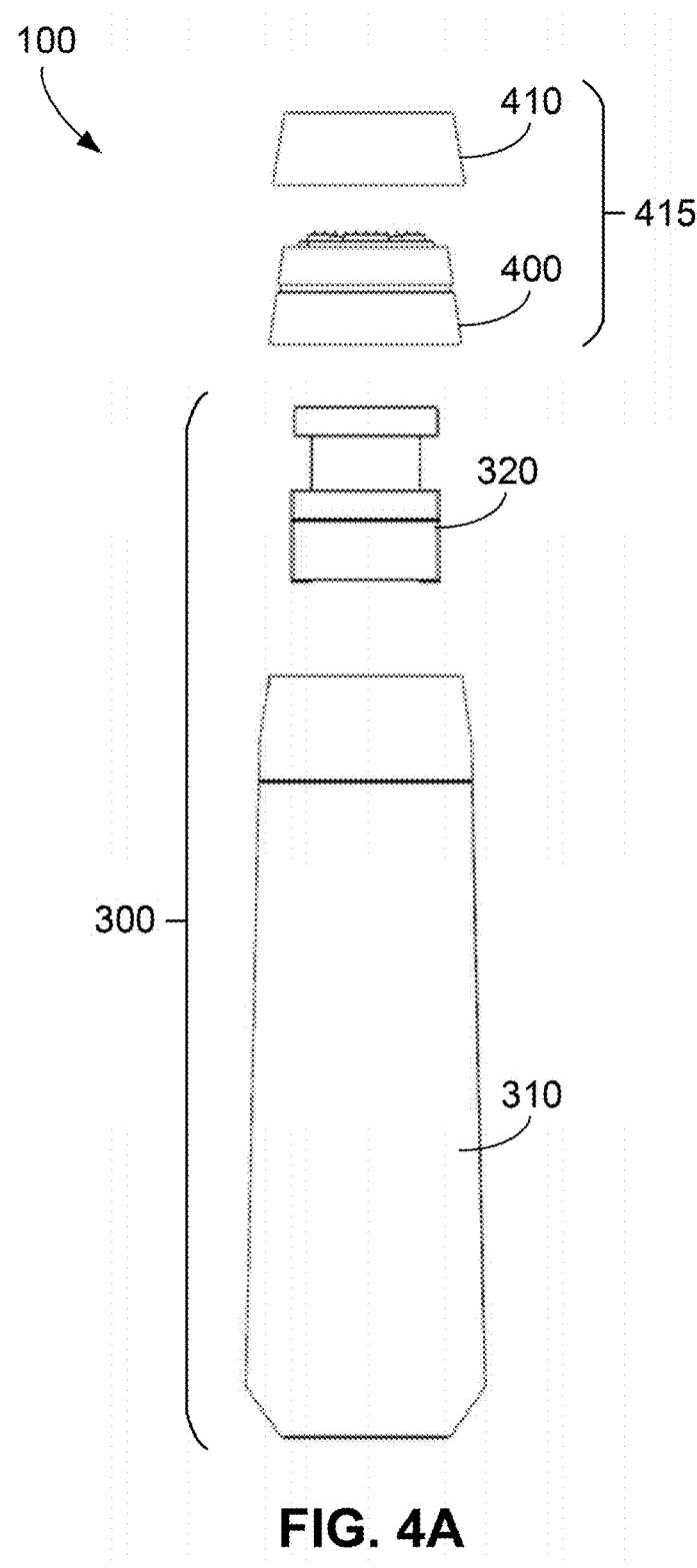

FIGS. 4A-4C illustrate an example of the light delivery device 100. As discussed, the light delivery device 100 includes the handpiece assembly 300 and the cartridge 400. The handpiece assembly 300 includes a handpiece 310 and optical transmission system 320. The handpiece 310 is a housing for systems of the light delivery device 100 and can be grasped by the user of the light delivery device 100 during use of the light delivery device 100, e.g., during delivery of light therapy by the light delivery device 100. The cartridge 400 is configured to be mounted to the handpiece assembly 300, as shown in FIG. 4B, e.g., via a threaded interface, a push-fit interface, or other attachment mechanisms.

The handpiece 310 can be manufactured using injection molding, casting, hot or cold forming, 3D printing, or other manufacturing techniques. The handpiece 310 can be made from a biocompatible material that can be disinfected between each use of the light delivery device 100. For example, the handpiece 310 can be formed of aluminum, stainless steel, ABS plastic, or another biocompatible material.

The cartridge 400 and a cartridge cap 410 can form a cartridge assembly 415, e.g., that is assembled as single-use, replaceable device. The cartridge cap 410 can be attached to the cartridge 400 to cover the piercing members of the cartridge 400, as shown in FIG. 4C. The cartridge cap 410 can prevent a user from inadvertent pricking.

Figure 5A:
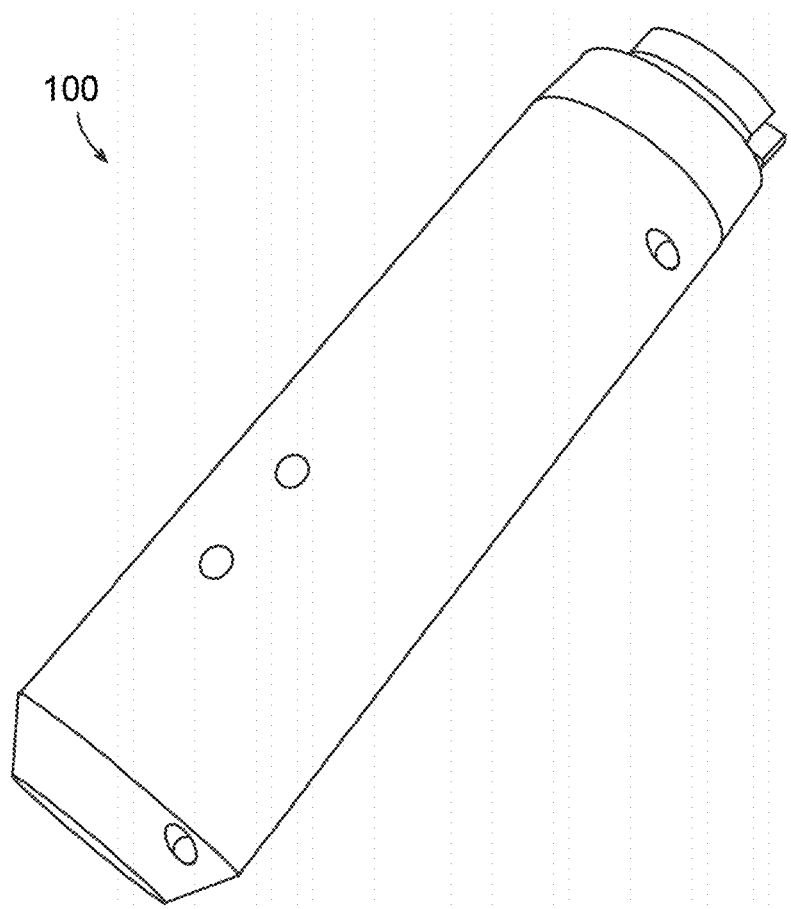
FIGS. 5A-5B are perspective and side views, respectively, of an example of a handpiece assembly for a light delivery device.
Figure 5B:
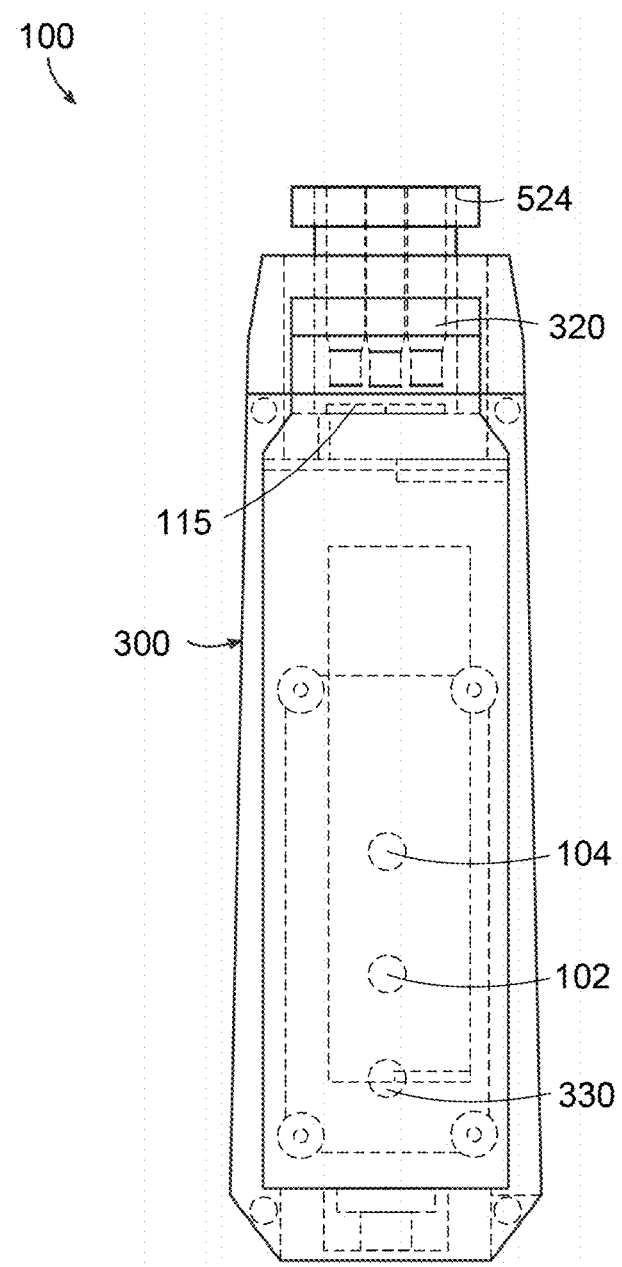

FIGS. 5A-5B illustrate an example of the handpiece assembly 300 for the light delivery device 100. As discussed in this disclosure, the handpiece assembly 300 can correspond to a reusable portion of the light delivery device 100. The handpiece assembly 300 includes structural components (e.g., the handpiece 310) and electrical components supported by the structural components. For example, as shown in FIG. 5B, the handpiece assembly 300 includes the buttons 102, 104, a visual status indicator 330 (of the indicator 540), the light source 110, the optical transmission system 320, and the cartridge detection sensor 524. In some implementations, the handpiece assembly 300 includes the energy storage device 140. The visual status indicator 330 can include one or more LED lights responsive to signals generated by the controller 510 (shown in FIG. 3A). The light source 110, as discussed in this disclosure, emits the light 115, which in turn is transmitted by the optical transmission system 320 to the piercing members of the cartridge 400. The light source 110 can include one or more light emitters positioned to emit light toward the optical transmission system 320. In implementations, the wavelength of the light emitted by the light source 110 can be in a range of approximately 280 nanometers (e.g., about 300 nm or more, about 320 nm or more, about 340 nm or more, about 360 nm or more, about 380 nm or more, about 400 nm or more, about 420 nm or more, about 440 nm or more, about 460 nm or more, about 480 nm or more, about 500 nm or more, about 520 nm or more, about 540 nm or more, about 560 nm or more, about 580 nm or more, about 600 nm or more, about 620 nm or more, about 640 nm or more, about 660 nm or more, about 680 nm or more, about 700 nm or more, about 720 nm or more, about 740 nm or more, about 760 nm or more, about 780 nm or more, about 800 nm or more, about 820 nm or more, about 840 nm or more, about 860 nm or more, about 880 nm or more, about 900 nm or more, about 920 nm or more, about 940 nm or more, about 960 nm or more, about 980 nm or more, about 1000 nm or more, about 1020 nm or more, about 1040 nm or more, about 1060 nm or more, about 1080 nm or more, about 1100 nm or more, about 1120 nm or more, about 1140 nm or more, about 1160 nm or more, about 1180 nm or more, about 1200 nm or more, about 1220 nm or more, about 1240 nm or more, about 1260 nm or more, about 1280 nm or more, about 1300 nm or more, about 1320 nm or more, about 1340 nm or more, about 1360 nm or more, about 1380 nm or more, about 1400 nm or more, about 1420 nm or more, about 1440 nm or more, about 1460 nm or more, about 1480 nm or more, about 1500 nm or more, about 1520 nm or more, about 1540 nm or more, about 1560 nm or more, about 1580 nm or more, about 1600 nm or more, about 1600 nm or more, about 1620 nm or more, about 1640 nm or more, about 1660 nm or more, about 1660 nm or more, about 1680 nm or more, about 1700 nm or more, about 1720 nm or more, about 1740 nm or more, about 1760 nm or more, about 1780 nm or more, about 1800 nm or more) to approximately 3000 nanometers or less (e.g., about 2980 nm or less, about 2960 nm or less, about 2940 nm or less, about 2920 nm or less, about 2900 nm or less, about 2880 nm or less, 2860 nm or less, about 2840 nm or less, about 2820 nm or less, about 2800 nm or less, about 2780 nm or less, 2760 nm or less, about 2740 nm or less, about 2720 nm or less, about 2700 nm or less, about 2680 nm or less, 2660 nm or less, about 2640 nm or less, about 2620 nm or less, about 2600 nm or less, about 2580 nm or less, 2560 nm or less, about 2540 nm or less, about 2520 nm or less, about 2500 nm or less, about 2480 nm or less, 2460 nm or less, about 2440 nm or less, about 2420 nm or less, about 2400 nm or less, about 2380 nm or less, 2360 nm or less, about 2340 nm or less, about 2320 nm or less, about 2300 nm or less, about 2280 nm or less, 2260 nm or less, about 2240 nm or less, about 2220 nm or less, about 2200 nm or less, about 2180 nm or less, 2160 nm or less, about 2140 nm or less, about 2120 nm or less, about 2100 nm or less, about 2180 nm or less, 2160 nm or less, about 2140 nm or less, about 2120 nm or less, about 2100 nm or less, about 2080 nm or less, 2060 nm or less, about 2040 nm or less, about 2020 nm or less, about 2000 nm or less, about 1980 nm or less, 1960 nm or less, about 1940 nm or less, about 1920 nm or less, about 1900 nm or less, about 1880 nm or less, 1860 nm or less, about 1840 nm or less, about 1820 nm or less). The light source may also use provide adjustable wavelengths (e.g., modulate wavelengths or alternate between different wavelengths).

Example Optical Systems

Figure 6A:
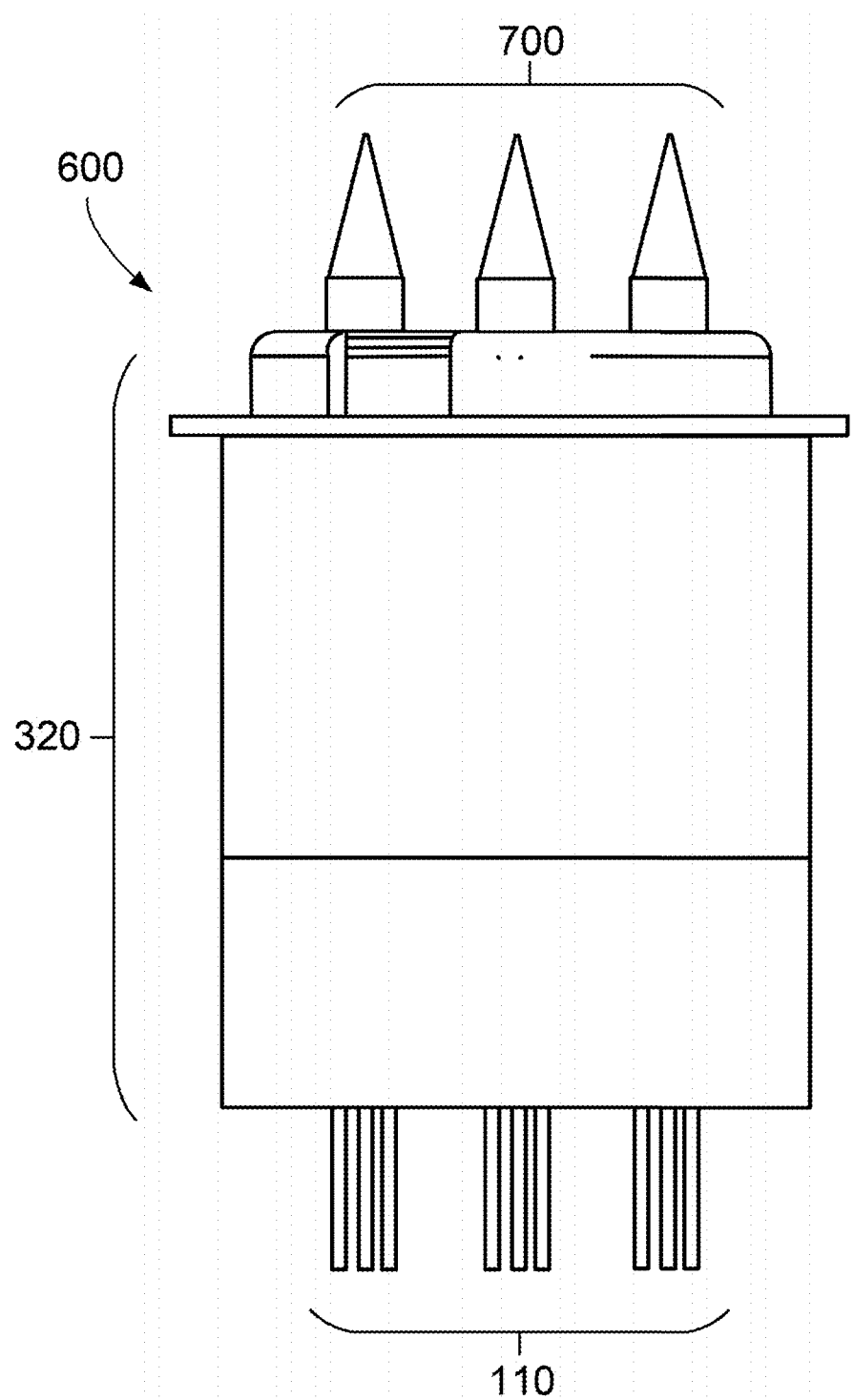
FIGS. 6A-6B are unexploded and exploded side views, respectively of an example of an optical transmission system for a light delivery device.
Figure 6B:
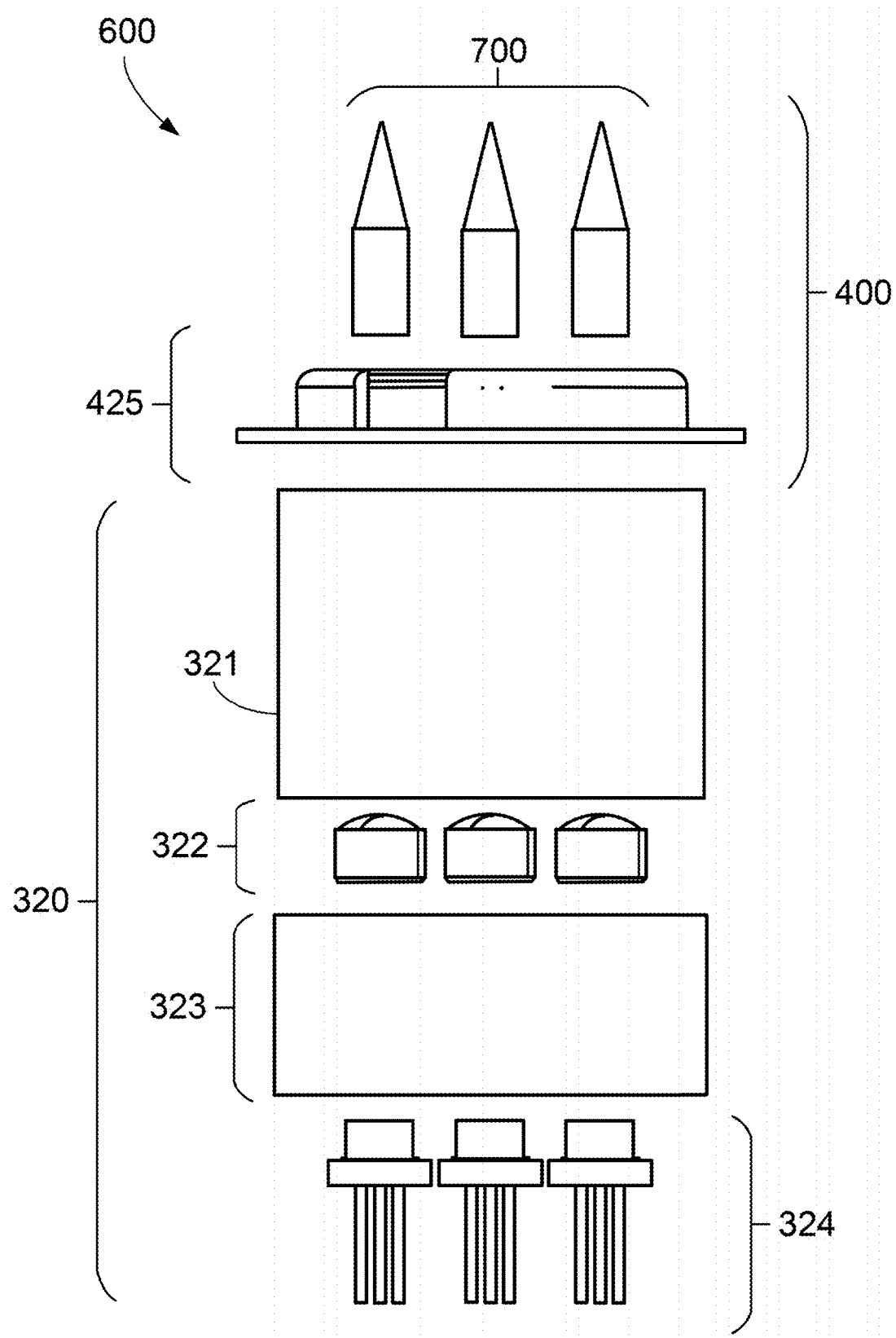

FIGS. 6A-6B illustrate examples of an optical system 600 including the light source 110 and optical needles 700. The optical system 600 can further include the optical transmission system 320. The optical needles 700 can correspond to all of or a subset of the piercing members 120 (FIG. 1A) of the light delivery device 100.

The optical transmission system 320 transmits the light emitted by the light source 110 to the optical needles 700. The optical transmission system 320 can include one or more optical elements for transmitting the light emitted by the light source 110 to the piercing members of the cartridge 400. In implementations, the one or more optical elements can include one or more of a fiber optic cable, a lens, a waveguide, or an optical diffuser. The one or more optical elements are positioned in a path of the light emitted by the light source 110.

In the example shown in FIG. 6B, the optical needles 700 and a needle holder 425 form at least part of the cartridge 400. A spacer 321, an array of lenses 322, a lens holder 323, and an array of light emitters 324 form at least part of the handpiece assembly 300. The light source 110 includes the array of light emitters 324. Each of the light emitters 324 can have an emitter size between 10 and 500 microns in diameter (e.g., between 30 and 300 microns in diameter). The light emitters 324 can be laser diodes, and the laser emitted by the light emitters 324 can have an output power between 1 and 1000 mW (e.g., between 5 and 300 mW) and a beam divergence half angle between 5 and 50 degrees (e.g., between 10 and 30 degrees). In some implementations, the light emitters 324 can be a semiconductor laser such as a laser diode, a light emitting diode with a tight emission wavelength band, a solid-state laser (e.g., a fiber laser), or another appropriate light emitter.

In the example shown in FIG. 6B, the optical transmission system 320 further includes the array of lenses 322. Each of the lenses 322 can have a numerical aperture between 0.5 and A diameter of each of the lenses 322 can be between 2 and 10 millimeters, e.g., between 2 and 8 millimeters, between 4 and 6 millimeters, about 4 mm, about 5 mm, about 6 mm, about 7 mm, about 8 mm, etc. A focal length of each of the lenses 322 can be between 4 and 8 millimeters, e.g., between 5 and 7 millimeters, between 5.5 and 6.5 millimeters, about 6 millimeters, etc. Each of the lenses 322 can be formed of a polymer material (e.g., polycarbonate) or glass material.

The needle holder 425, the spacer 321, and the lens holder 323 can be configured to align the optical needles 700 with the array of lenses 322. For example, these components can mate with one another in a way that ensures that the array of lenses 322 and the optical needles 700 are aligned with one another along a longitudinal axis. When aligned, proximal surfaces of the lenses 322 can be positioned a distance in a range of approximately 3 millimeters or more (e.g., about 3.5 mm or more, about 4 mm or more, about 4.5 mm or more, about 5 mm or more, about mm or more, about 6 mm or more) to approximately 12 millimeters or less (e.g., about 11.5 mm or less, about 11 mm or less, about 10.5 mm or less, about 10 mm or less, about 9.5 mm or less, about 9 mm or less, about 8.5 mm or less, about 8 mm or less, about 7.5 mm or less, about 7 mm or less, about 6.5 mm or less) from the light emitters 324, and distal surfaces of the lenses 322 can be positioned a distance in a range of approximately 33 millimeters or more (e.g., about mm or more, about 40 mm or more, about 45 mm or more, about 50 mm or more) to approximately 70 millimeters or less (e.g., about 65 mm or less, about 60 mm or less, about 55 mm or less) from proximal surfaces of the optical needles 700.

The light emitters 324, the lenses 322, and the optical needles 700 can have a one-to-one arrangement. For example, each of the light emitters 324 of the light source 110 can be positioned to emit light to a corresponding lens of the lenses 322, which in turn transmits the light to a corresponding piercing member of the optical needles 700. The optical needles 700 can serve as optical diffusers such that light transmitted to the optical needles 700 diffuse upon being transmitted through exterior surfaces of the optical needles 700.

Example Cartridge Assemblies

Figure 7A:
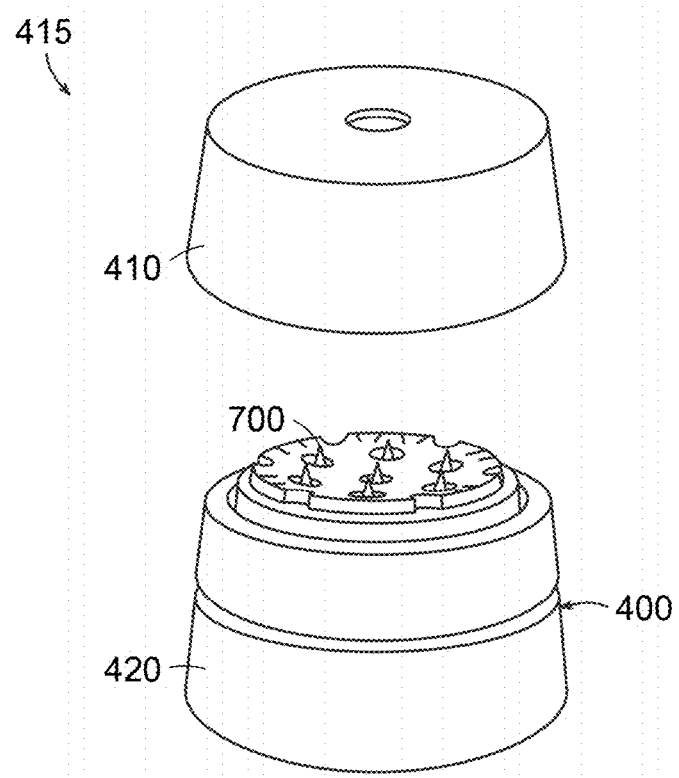
FIGS. 7A-7D are exploded perspective, unexploded side, unexploded side cross-sectional, and exploded side views, respectively, of an example of a cartridge assembly for a light delivery device.
Figure 7B:
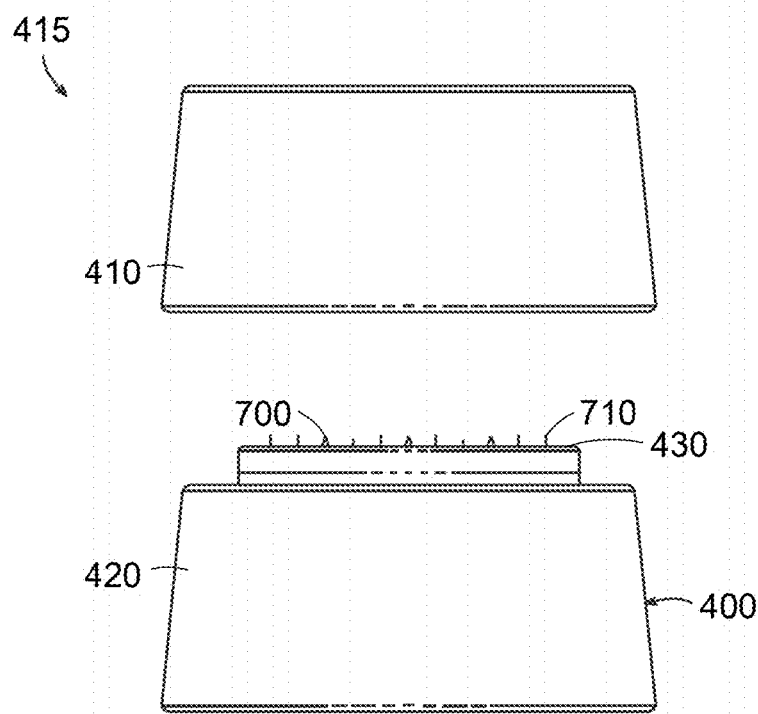

FIGS. 7A-7D illustrate an example of the cartridge assembly 415 including the cartridge 400 and the cartridge cap 410. The cartridge 400 includes a housing 420 and the piercing members 120. As shown in FIG. 7B, the piercing members 120 can include at least two types of piercing members, including the optical needles 700 and mechanical needles 710.

The housing 420 is mountable to part of the light delivery device 100, e.g., the handpiece assembly 300. The housing 420 includes one or more structural components for holding the piercing members 120 of the cartridge 400, for mating with the part of the light delivery device 100, and for mating with the cartridge cap 410. For example, as shown in FIG. 7D, the housing 420 includes an outer casing 421, a conformable cover 422, a cartridge cover 423, a core 424, the contact sensor 526, and the needle holder 425. The housing 420 can be manufactured using techniques such as injection molding, 3D printing, etching (by means of chemicals or lasers) from biocompatible materials, or other techniques. The housing 420 can be formed of biocompatible materials, including polymers or ceramics.

The conformable cover 422 is positioned within the outer casing 421 and at least partially defines a distal surface 430 of the cartridge 400. The conformable cover 422 provides a conformable layer that defines the distal surface 430, thereby allowing the distal surface 430 of the cartridge 400 to conform to underlying geometry against which the distal surface 430 is placed. The conformable cover 422 is formed of an elastic and/or compressible material. For example, the conformable cover 422 can be formed of a rubber or rubber-like material or an elastomer. In some implementations, the conformable cover 422 is formed of a polymer such as silicone or a thermoplastic polyurethane material.

The cartridge cover 423 is positioned within the outer casing 421 and is engaged with the outer casing 421. At least some of the piercing members 120 are mounted to the core 424. In the example shown in FIG. 7D, the mechanical needles 710 are mounted to the core 424. And at least some of the piercing members 120 are mounted to the needle holder 425. In the example shown in FIG. 7D, the optical needles 700 are mounted to the needle holder 425. The needle holder 425 can mate with the core 424 so that the optical needles 700 and the mechanical needles 710 are aligned with one another.

The contact sensor 526 can further include contact sensor alignment pins 426 (e.g., pin members extending from the contact sensor 526) mechanically aligned with the needle holder 425 that interface with the handpiece 100 to align the optical needles 700 relative to the light emitted by the light source 110 (shown in FIGS. 6A-6B) relative to the optical transmission system 320 (shown in FIGS. 6A-6B), and relative to the contact sensor 526. When the cartridge 400 is attached to the handpiece assembly 300, the contact sensor alignment pins 426 can mate with part of the spacer 321 (shown in FIGS. 6A-6B) to achieve this alignment.

Example Piercing Members

Figure 8A:
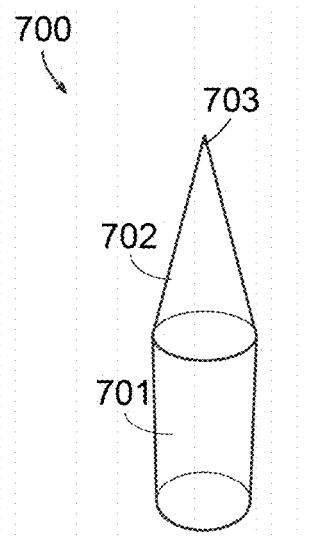
FIGS. 8A-8B are perspective and side views, respectively, of an example of a piercing member of the cartridge of FIGS. 7A-7D.
Figure 8B:
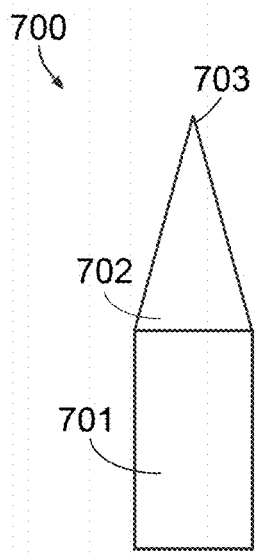

FIGS. 8A-8B illustrate an example of one of the optical needles 700. As discussed in this disclosure, the optical needles 700 receive light emitted by the light source 110 (shown in FIG. 6A) and allow the light to be dispersed into the subdermal or intradermal portion of the skin. Referring to FIGS. 8A-8B, the optical needle 700 is light-transmissive, e.g., allows transmission of at least 50%, at least 60%, at least 70%, at least 80%, at least 90%, at least 95%, or at least 99% of light in a wavelength between 280 and 3000 nanometers.

Surfaces of the optical needle 700 can be treated to achieve certain optical properties. For example, to improve the transmissivity of the optical needle 700, a surface of the optical needle 700 can be polished. An oil layer can be placed on the surface of the optical needle 700 to increase a numerical aperture of the optical needle 700. The surface of the optical needle 700 can be roughened or covered with diffusion elements (e.g., crystals) to enhance diffusivity of the optical needle 700, thereby allowing light transmitted through the optical needle 700 to diffuse as the light is delivered into the subdermal or intradermal portion of the skin. In some implementations, the optical needle 700 is at least partially covered with an opaque coating element. One or more portions of the surface of the optical needle 700 can be covered with an opaque coating element so that the light delivered through the optical needle 700 is primarily delivered through non-covered portions of the surface of the optical needle 700.

By being formed of a light-transmissive material, a separate light guide does not need to be inserted into the optical needle 700 to allow for delivery of light. Rather, the optical needle 700 functions both to penetrate the biological surface and to deliver the light. The optical needle 700 can be manufactured using machining, 3D printing, injection molding, casting, chemical, laser or another type of etching from a substrate, hot or cold forming, or another appropriate manufacturing method.

In some implementations, the optical needle 700 can further serve as focusing element or a lens to cause the light delivered into the optical needle 700 to be focused as it travels through the optical needle 700 and out through the distal surface of the optical needle 700. The geometry and optical characteristics of the optical needle 700 can be designed to achieve a desired energy delivery profile, e.g., with a desired uniformity and a desired concentration.

The optical needle 700 includes a proximal portion 701 and a distal portion 702. The proximal portion 701 can have a uniform width. In some implementations, the proximal portion 701 is cylindrical. The distal portion 702 has a tapered width, e.g., tapering to a distal tip 703 of the optical needle 700. The distal portion 702 can be conical or prismatic.

The cartridge 400 is configured such that at least part of the distal portion 702 of the optical needle 700 is insertable into biological tissue. In particular, the optical needle 700 is positioned relative to distal surface 430 of the cartridge 400 to protrude a particular amount from the distal surface 430. The optical needle 700 protrudes beyond the distal surface 430 of the cartridge 400 by a non-zero distance, e.g., a longitudinal distance from the distal tip 703 of the optical needle 700 to a proximal end of the optical needle 700. The amount that the optical needle 700 protrudes from the distal surface 430 of the cartridge can be selected to ensure that light delivered by the optical needle 700 is directed at a target layer of tissue, e.g., at a targeted part of a subdermal or intradermal layer of skin. In some implementations, this distance is at least millimeters, at least 1.0 millimeters, at least 1.5 millimeters, at least 2.0 millimeters, etc. In some implementations, this distance is between 0.5 and 2.5 millimeters, between 0.5 and 2.0 millimeters, between 1.0 and 2.5 millimeters, between 1.0 and 2.0 millimeters, etc. In some implementations, this distance is about 0.5 millimeters, about 1.0 millimeters, about 1.5 millimeters, about 2.0 millimeters, about 2.5 millimeters, etc.

The quantity of the optical needles 700 can be selected to ensure that the light delivered to the targeted area of the biological tissue is sufficiently distributed. The quantity of the optical needles 700 in the example of the cartridge 400 shown in FIG. 7A is 7, though this varies in implementations. In some implementations, the quantity of the optical needles 700 on the cartridge 400 can be at least 1, at least 3, at least 5, at least 7, at least 10, or more. In some implementations, the quantity of the optical needles is no more than 50, no more than 40, no more than 30, no more than 20, no more than 10, etc. In some implementations, the quantity of the optical needles is between 1 and 10, between 1 and 20, between 1 and 30, between 1 and 40, between 1 and 50, etc. The quantity of the optical needles 700 can be selected based on an overall contact area of the cartridge 400 on the biological surface. For example, the cartridge 400 can include 1 to 50 optical needles per square centimeter, e.g., 1 to 25 optical needles per square centimeter, 1 to 10 optical needles per square centimeter, at least 1 optical needle per square centimeter, at least 3 optical needles per square centimeter at least 5 optical needles per square centimeter, at least 7 optical needles per square centimeter, etc.

In implementations, the distal tip 703 of the optical needle 700 can have a thickness of no more than 10, 20, 30, 40, 50, 60, 70, 80, 90, 100, 110, 130, 140, 150, 160, 170, 180, 190, or 200. The optical needle 700 can be formed of an optically transparent material and/or a biocompatible material. For example, the optical needle 700 can be formed of a polymer material, a ceramic material, a glass material, silica, quartz, polymethyl methacrylate (PMMA), polystyrene, polycarbonate or another optically transparent material. The material of the optical needle 700 can include a biodegradable material, such as hyaluronic or polylactic acid. In some implementations, the optical needle 700 can be a composite material formed of two or more of any of the foregoing materials.

Figure 9A:
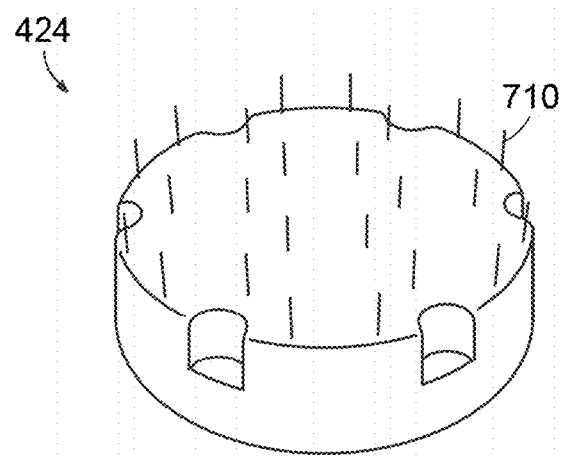
FIG. 9A is a perspective view of an example of a piercing member on the core of the cartridge assembly of the FIGS. 7A-7D.
Figure 9B:
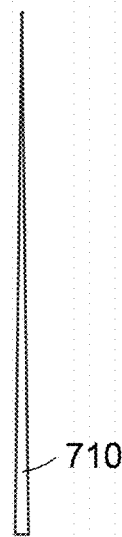
FIG. 9B is a side view of an example of the piercing member of FIG. 9A isolated from the core.

FIG. 9A illustrates an example of the core 424, including the mechanical needles 710 attached to the core 424. The mechanical needles 710 protrude distally from the core 424. FIG. 9B illustrates an example of one of the mechanical needles 710 on the core 424. In contrast to the optical needle 700, the mechanical needle 710 can be reflective or opaque to light, e.g., absorbs and/or reflects at least 50%, at least 60%, at least 70%, at least 80%, at least 90%, at least 95%, or at least 99% of light in a wavelength between 280 and 3000 nanometers. The mechanical needle 710 can be a microneedle that produces microdamage when inserted into skin of a subject.

The mechanical needle 710 protrudes beyond the distal surface 430 of the cartridge 400 by a non-zero distance, e.g., a longitudinal distance from a distal tip of the mechanical needle 710 to a proximal end of the mechanical needle 710. In some implementations, this distance is at least 0.5 millimeters, at least 1.0 millimeters, at least 1.5 millimeters, at least 2.0 millimeters, etc. In some implementations, this distance is between 0.5 and 2.5 millimeters, between 0.5 and 2.0 millimeters, between 1.0 and 2.5 millimeters, between 1.0 and 2.0 millimeters, etc. In some implementations, this distance is about 0.5 millimeters, about 1.0 millimeters, about 1.5 millimeters, about 2.0 millimeters, about 2.5 millimeters, etc.

The quantity of the mechanical needles 710 can be selected to ensure that the microdamage on the tissue is sufficiently distributed. The quantity of the mechanical needles 710 in the example of the cartridge 400 shown in FIG. 7A is 24, though this varies in implementations. In some implementations, the quantity of the mechanical needles 710 on the cartridge 400 can be at least 1, at least 3, at least 5, at least 7, at least 10, or more. In some implementations, the quantity of the mechanical needles is no more than 50, no more than 40, no more than 30, no more than 20, no more than 10, etc. In some implementations, the quantity of the mechanical needles is between 1 and 100, between 10 and 100, between 10 and 50, etc. The quantity of the mechanical needles 710 can be selected based on an overall contact area of the cartridge 400 on the biological surface. For example, the cartridge 400 can include 1 to 100 mechanical needles per square centimeter, e.g., 1 to 50 mechanical needles per square centimeter, 1 to 25 mechanical needles per square centimeter, 1 to 10 mechanical needles per square centimeter, at least 1 mechanical needle per square centimeter, at least 3 mechanical needles per square centimeter at least 5 mechanical needles per square centimeter, at least 7 mechanical needles per square centimeter, etc.

The optical needle 700 and the mechanical needle 710 can be formed of different materials. The mechanical needle 710 is opaque to light. The mechanical needle 710 can be formed of a non-light transmitting material, an optically reflective material, or an optically absorbent material. For example, the mechanical needle 710 can be formed of a metal, such as stainless steel or other medical-grade metallic materials. The material of the mechanical needle 710 can be castable, machinable, malleable, injection molded, 3D printed, hot or cold formed, machined, or etched. The material of the mechanical needle 710 can be a biocompatible material, such as a biocompatible metal (e.g., stainless steel, titanium, copper, aluminum, gold, silver etc.), a biocompatible polymer (e.g., acrylonitrile butadiene styrene, polyethylene, etc.), or other biocompatible material. For example, the material can be formed of biodegradable material, such as polylactic acid or hyaluronic acid. In some implementations, the mechanical needle 710 can be a composite material formed of two or more of any of the foregoing materials.

Relative dimensions of the optical needles 700 and the mechanical needles 710 can vary in implementations. Dimensions of the optical needles 700 and the mechanical needles 710 can be selected to provide sufficient microdamage (e.g., caused by the optical needles 700 and the mechanical needles 710) and provide sufficient light distribution (e.g., delivered by the optical needles 700). For example, the quantity of the mechanical needles 710 on the cartridge 400 can be at least 2 times the quantity of the optical needles 700, e.g., at least 1.5 times, at least 2.5 times, at least 3 times, at least 4 times, etc. the quantity of the optical needles.

A width of the mechanical needles 710 can be no more than a width of the optical needles 700. For example, a width of each needle of the mechanical needles 710 can be between 0.1 millimeters and 2 millimeters, and a width of each needle of the optical needles 700 can be between 2 and 5 millimeters. In some implementations, the width of the mechanical needles 710 can be between 0.1 and 0.3 millimeters, and the width of the optical needles 700 can be between 2.5 and 3.5 millimeters. In some implementations, the width of each needle of the mechanical needles 710 is about 0.2 millimeters, and the width of each needle of the optical needles 700 is about 3 millimeters. In some implementations, the width of the mechanical needles 710 is less than the width of the optical needles 700 by an amount between 2 and 4.7 millimeters, e.g., between 2 and 4 millimeters, between 2.5 and 3.5 millimeters, etc.

A width of the insertable portions of the needles 700, 710 that protrude from the cartridge, e.g., the portion of the needles that is inserted into the tissue, can vary from one another. In particular, the width of the insertable portions of the optical needles 700 can be between 0.1 and 2 millimeters. In some implementations, the width of the insertable portions of the mechanical needles 710 can be between 0.1 and 0.3 millimeters, and the width of the insertable portions of the optical needles 700 can be between 0.3 and 0.6 millimeters. In some implementations, the width of the insertable portions of each needle of the mechanical needles 710 is about 0.2 millimeters, and the width of the insertable portions of each needle of the optical needles 700 is about 0.5 millimeters. In some implementations, the width of the insertable portions of the mechanical needles 710 is less than the width of the insertable portions of the optical needles 700 by an amount between 0 and 0.5 millimeters, e.g., between 0 and 0.4, between 0 and 0.3, between 0 and 0.2 millimeters, between 0 and 0.1 millimeters, between 0.1 and 0.3 millimeters, between 0.2 and 0.3 millimeters, between 0.15 and 0.35 millimeters, etc.

Figure 10A:
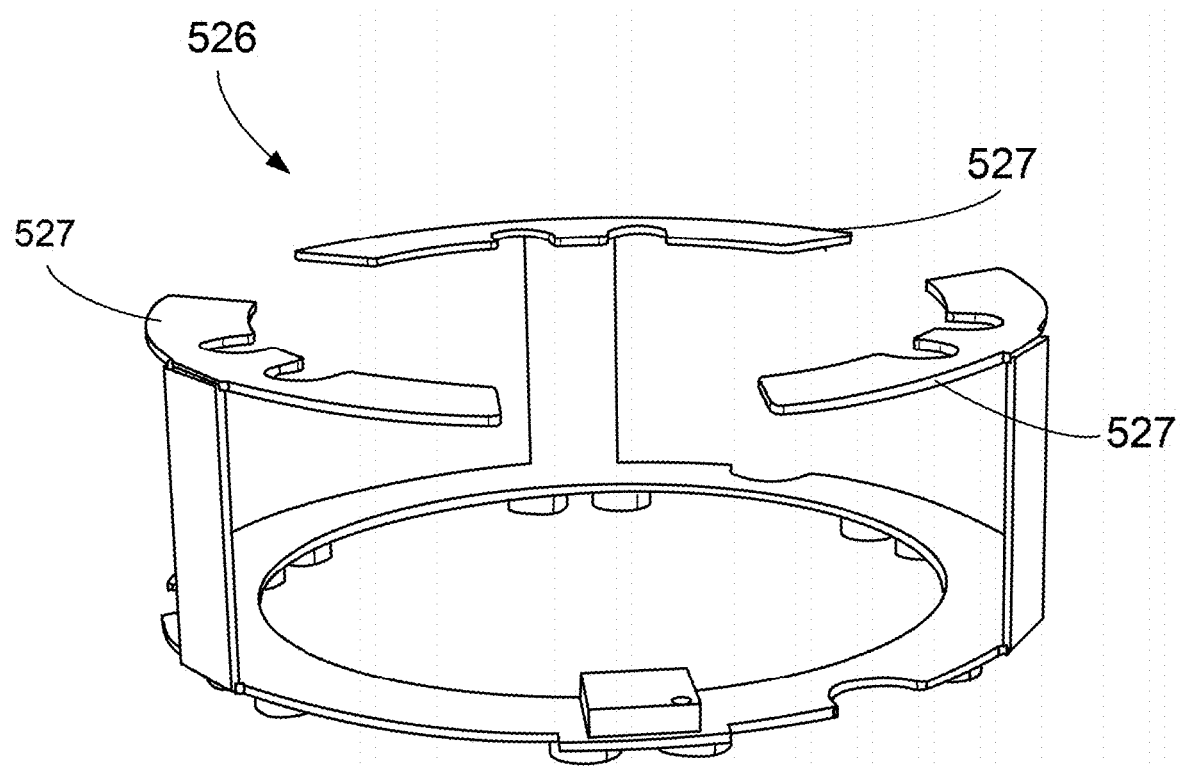
FIG. 10A is a perspective view of an example of a contact sensor.

FIG. 10A illustrates an example of a contact sensor device 526 of the light delivery device 100. In some implementations, the contact sensor device 526 is part of the cartridge 400 and is part of the single-use portion of the light delivery device 100 when the cartridge 400 is single-use. For example, the contact sensor device 526 can be positioned within the outer casing 421 of the cartridge 400 between the core 424 and the cartridge cover 423 (shown in FIG. 7D). In some implementations, the contact sensor device 526 is part of the handpiece assembly 300 and can thus be part of the multi-use portion of the light delivery device 100.

The contact sensor device 526, as described below, can detect contact or proximity between the distal surface of the light delivery device 100 and the biological surface. The contact sensor device 526 is configured to detect contact between the distal surface of the light delivery device 100 (e.g., the distal surface of the cartridge 400) and the biological surface (e.g., the surface of the skin of the subject). In some implementations, the contact sensor device 526 can detect that the biological surface is within a distance of 1 to 3 millimeters, e.g., 1 to 2 millimeters, 1.5 to 2.5 millimeters, no more than 1, 1.2, 1.4, 1.6, 1.8, 2, 2.2, 2.4, 2.6, 2.8, 3.0, 3.2, 3.4, 3.6, 3.8, 4.0, 4.2, 4.4, 4.6, 4.8, 5.0, 5.2, 5.4, 5.6, 5.8, 6.0, 6.2, 6.4, 6.6, 6.8, 7.0, 7.2, 7.4, 7.6, 7.8, 8.0, 8.2, 8.4, 8.6, 8.8, 9.0, 9.2, 9.4, 9.6, 9.8, or 10 millimeters, etc., from the distal surface of the light delivery device 100. In some implementations, the contact sensor device 526 can be used to detect an amount of pressure on the tissue. The detected amount of pressure can be used to determine an amount of insertion of the piercing members of the light delivery device. For example, delivery of light can be initiated in response to the amount of insertion being within a desired range or above a desired threshold. The contact sensor device 526 includes at least three separate contact sensors 527 configured to detect contact between the distal surface of the cartridge 400 and the biological surface. The three contact sensors 527 can be positioned to form a triangle. In some implementations, the contact sensor device 526 and each of the contact sensors 527 are capacitive sensors. The contact sensors 527 can be formed of tin, solder, copper, gold, or any other sterilizable and biocompatible material with or without metal plating techniques. In some examples, the contact sensor device 526 can include fewer or more than three separate contact sensors.

Figure 10B:
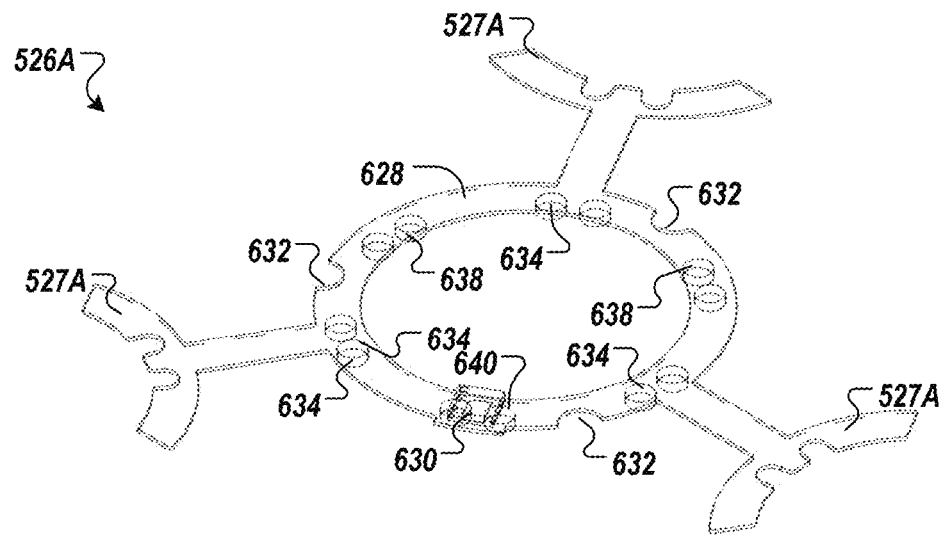
FIG. 10B is a perspective view of a different example contact sensor.
Figure 10C:
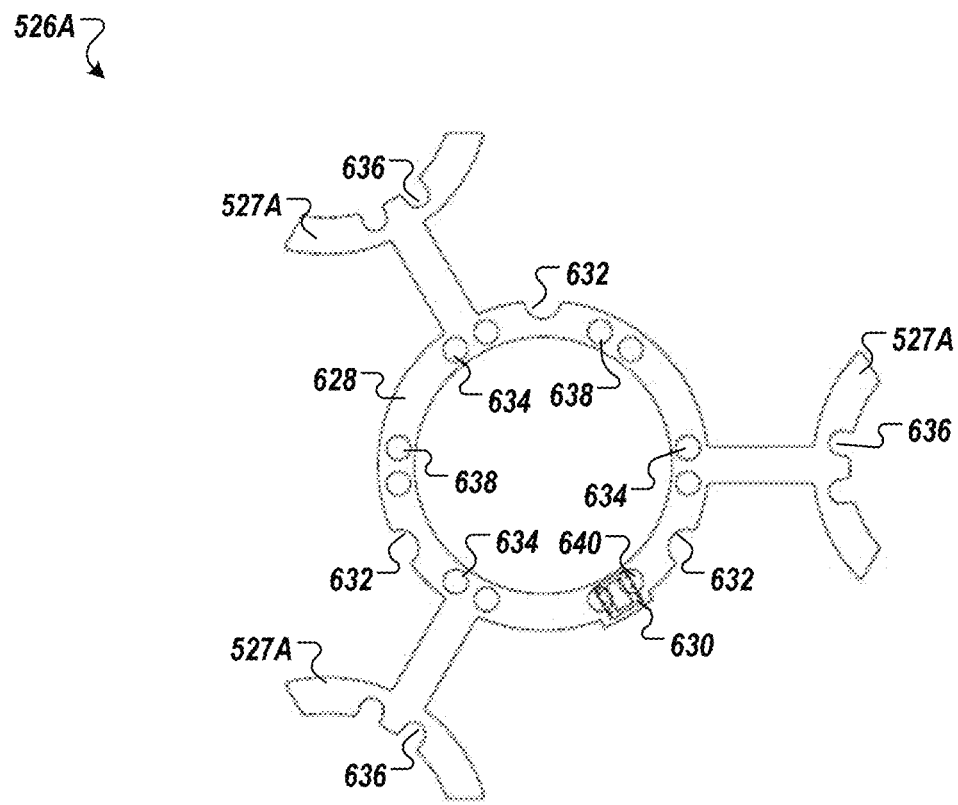
FIG. 10C is a top view of the contact sensor of FIG. 10B.

FIGS. 10B and 10C illustrate another example of a contact sensor device 526A that may be implemented into the light delivery device 100. The contact sensor device 526A is similar to the contact sensor device 526 of FIG. 10A. Thus, for ease of reference, and to the extent possible, the same or similar components of the second example contact sensor device 526A will retain the same reference numbers as outlined above with respect to the first example contact sensor device 526, although the reference numbers will be denoted by the letter 'A'. In addition to the functions described with respect to the first contact sensor device 526, the second contact sensor device 526A also provides different functionality. The contact sensor device 526A has three separate contact sensors 527A extending from a central ring 628 and that are configured to detect contact between the distal surface of a cartridge and the biological surface. Each of the contact sensors 527A is a curved flange and is connected to the central ring 628 by an arm. The arms are arranged to bend around an outer circumference of a core of a cartridge, placing the contact sensors 527A in contact with a surface of the core 424.

The central ring 628 includes a protruding tab 630 (i.e., a memory chip for the re-use prevention mechanism) extending from a first surface of the ring 628, a plurality of notches 632 formed in a circumference of the ring 628 and disposed between the contact sensors 527A, and a plurality of cartridge detection points 634, 638, 640 extending from a second surface (opposite the first surface) of the ring 628. The protruding tab 630 is shaped for extending into a corresponding space formed in the core of the cartridge. The notches 632 are sized to receive corresponding protrusions formed in an outer casing of the cartridge. Similarly, the contact sensors 527A include notches 636 that correspond with protruding elements formed in the cartridge cover and allow the positioning of metal needles in the perimeter of the cartridge.

In FIGS. 10B and 10C, the cartridge sensor 526A includes six pairs of contact points 634, 638, 640. Three pairs of the contact points 634 are aligned with the contact sensors 527A, two pairs 638 are used as a cartridge detection mechanism, and the remaining pair 640 is used for data interchange with the EEPROM memory (described further below with respect to FIGS. 12B and 12C). The two pairs 638 arranged for the cartridge detection are placed non-symmetrically. Once the two pairs of cartridge detection points 638 are detected in the proper position by the controller 510A, one of the light delivery protection mechanisms is disabled (skin contact and activating the button may also be required for light delivery).

Figure 10D:
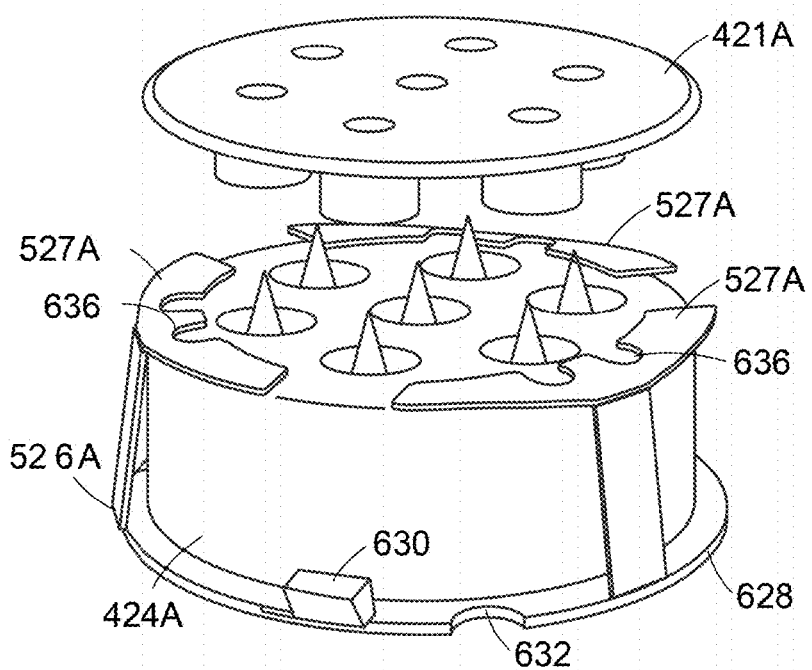
FIG. 10D is a partially exploded view of a cartridge core, piercing members, cover, and the contact sensor of FIG. 10B.
Figure 10E:
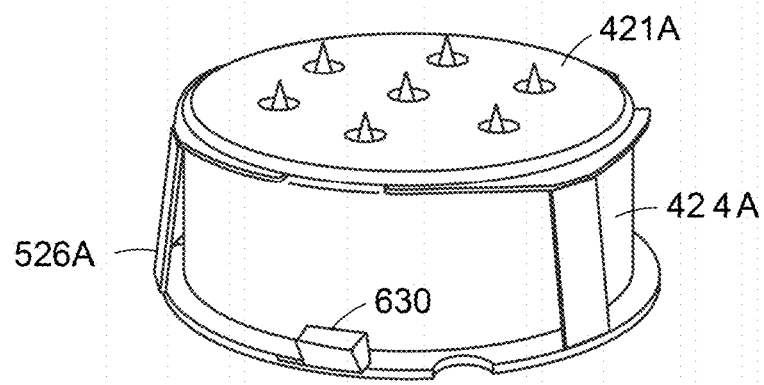
FIG. 10E is a perspective, assembled view of the cartridge core, piercing members, cover, and contact sensor of FIG. 10B.

As shown in FIGS. 10D and 10E, the notches 632 of the contact sensor device 526A are positioned to align with a cartridge 400A to facilitate a unique identification (UID) reading and correct alignment of the cartridge 400A and the handpiece assembly 300. The cartridge 400A is similar to the cartridge 400 of the other figures. Thus, for ease of reference, and to the extent possible, the same or similar components of the second example cartridge 400A will retain the same reference numbers as outlined above with respect to the first example light delivery device 100, although the reference numbers will be denoted with the letter 'A'. In the illustrated example, the notches 632, and tab 630 of the sensor device 526A are configured to align and couple with the cartridge 400A in only one position for proper installation. Specifically, the tab 630 aligns with a notch formed in the circumference of the core 424A. The notches 632 of the central ring 628 align with protruding portions of the cartridge casing and/or the conformable cover 422A to align the sensor 526A with the cartridge 400A. The protrusions 811A, 813A differ in shape so that the user cannot install the cartridge 400A improperly. While FIG. 11G illustrates two protrusions 811A, 813A, the cartridge 400A may include fewer or more protrusions arranged to create a reliable installation assembly.

Figure 10F:
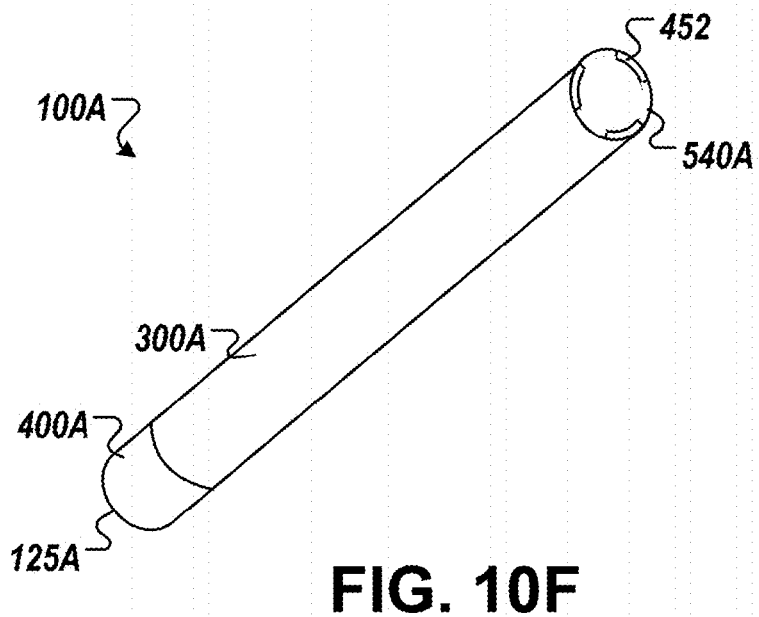
FIG. 10F is a back, perspective view of an example of a light delivery device showing a feedback mechanism.
Figure 10G:
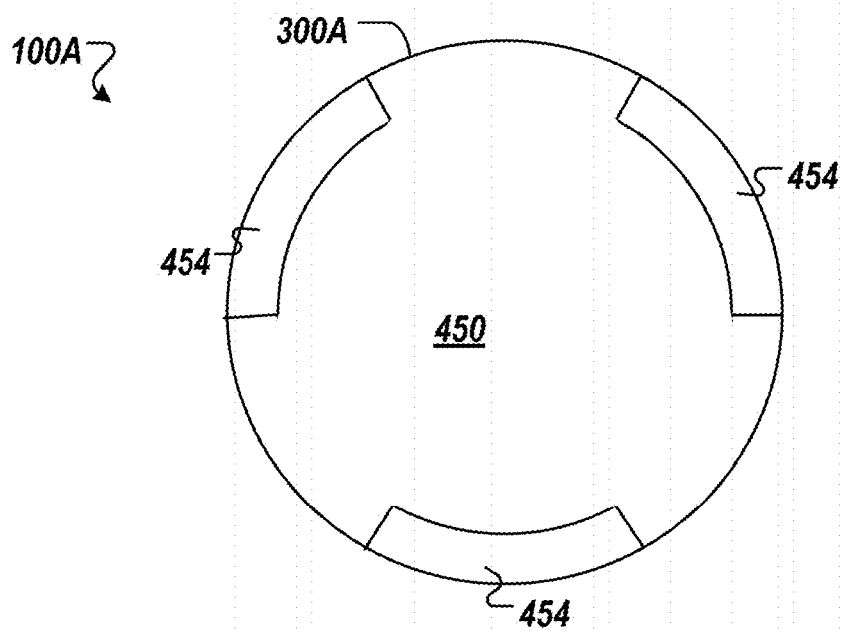
FIG. 10G is a magnified back view of the light delivery device of FIG. 10F.

FIGS. 10F and 10G illustrate another example of a light delivery device 100A incorporating the contact sensor device 526A. The light delivery device 100A is similar to the light delivery device 100 of the previous figures. Thus, for ease of reference, and to the extent possible, the same or similar components of the second example light delivery device 100A will retain the same reference numbers as outlined above with respect to the first example light delivery device 100, although the reference numbers will be denoted with the letter 'A'.

A handpiece assembly 300A of the light delivery device 100A of FIGS. 10F and 10G is configured to register real-time contact between the skin and the cartridge 400. The light delivery device 100A includes a measurement tool that translates a contact measurement into a capacitance measurement. The capacitance increases if the contact surface increases or if the distance between the light delivery device 100A and the patient (e.g., the head of the patient) decreases. For example, if the capacitance increases, the measurement tool can determine that the contact surface is increasing and/or the distance is decreasing. The measurement tool can utilize the capacitance to determine an alignment of the tool relative to the patient and/or a pressure value representing the pressure between the patient and the light delivery device 100A. For example, the measurement tool can record the measured capacitance and compare the capacitance with a table (e.g., a lookup table) to determine a corresponding pressure value, e.g., to determine thresholds for proper contact between the skin and the cartridge 400A.

A measurement module communicates the force and orientation map to a display module 540A that displays the result in the form of an LED ring 452. For example, capacitive values are used to determine thresholds for proper contact between the skin and the cartridge 400A, and can be translated into light or auditory feedback to the user. For example, the controller 510A is configured to translate a measured capacitance between the cartridge and the skin surface into pressure to determine proper alignment. Three conductive detection points 527A built inside the cartridge 400A make a "capacitive circuit" with the skin surface, and the controller 500A registers a capacitive value based on the measurements taken by the sensors. If the distance between the sensor 527A and the skin reaches a maximum distance, the capacitive measurement cannot be obtained. If the distance between the sensor 527A and the skin is less than 10 mm, pressure and capacitive measurements can be correlated. Applying more pressure into the skin with the cartridge 400A to increase surface contact between the skin and the cartridge results in a higher capacitive value.

In the illustrated example, the display module 540A is located on a proximal end of the handpiece assembly 300, opposite the cartridge 400A. However, in other examples, the display module 540A may be at a different location on the handpiece assembly 300. The LED ring, as shown in FIG. 10G, provides visual feedback to the user regarding the level of contact established between the skin and the cartridge 400A, and, more specifically, the level of contact established between each of three different sensors 427 of the cartridge 400A and the skin. A gradient of colors or brightness can be used to display intermediate states while the cartridge 400A is in contact, depending on the force and angle that is applied.

For example, when the handpiece assembly 300A is completely perpendicular to the target surface (e.g., skin surface S), then each of three ring segments 454 will register a color associated with a correct alignment, e.g., green. If, on the other hand, the handpiece assembly 300A is not in correct alignment with the target surface, then one or more of the ring segments 454 on the display module 540A will register a different color that is associated with an incorrect alignment, e.g., red. Because the ring segments 454 correspond to the position of the sensors 427, which are measuring the contact between the cartridge 400A and the skin surface, the user can adjust the positioning of the cartridge 400A relative to the skin by tilting the handpiece assembly 300A in a direction corresponding to the ring segment displaying an incorrect alignment color until each ring segment is in correct alignment. The system and method thus provide accurate and reliable device alignment detection for use in a variety of applications.

Example Re-Use Prevention Mechanisms

FIGS. 11A-11D illustrate a first example of a re-use prevention mechanism 800 for the cartridge 400 that can be included in certain implementations. The re-use prevention mechanism 800 is configured to prevent the cartridge 400 from being used more than once with the light delivery device 100. For example, the re-use prevention mechanism 800 can prevent operation of the light delivery device 100 (e.g., activation of the light source of the light delivery device 100) after removal of the cartridge 400 from the handpiece assembly 300. In further examples, the re-use prevention mechanism can prevent the cartridge 400 from being coupled to the handpiece assembly 300 after the cartridge 400 is removed from the handpiece assembly 300. A first portion 810 of the re-use prevention mechanism 800 can be positioned on the cartridge 400, and a second portion 820 of the re-use prevention mechanism 800 can be positioned on the handpiece assembly 300.

Figure 7C:
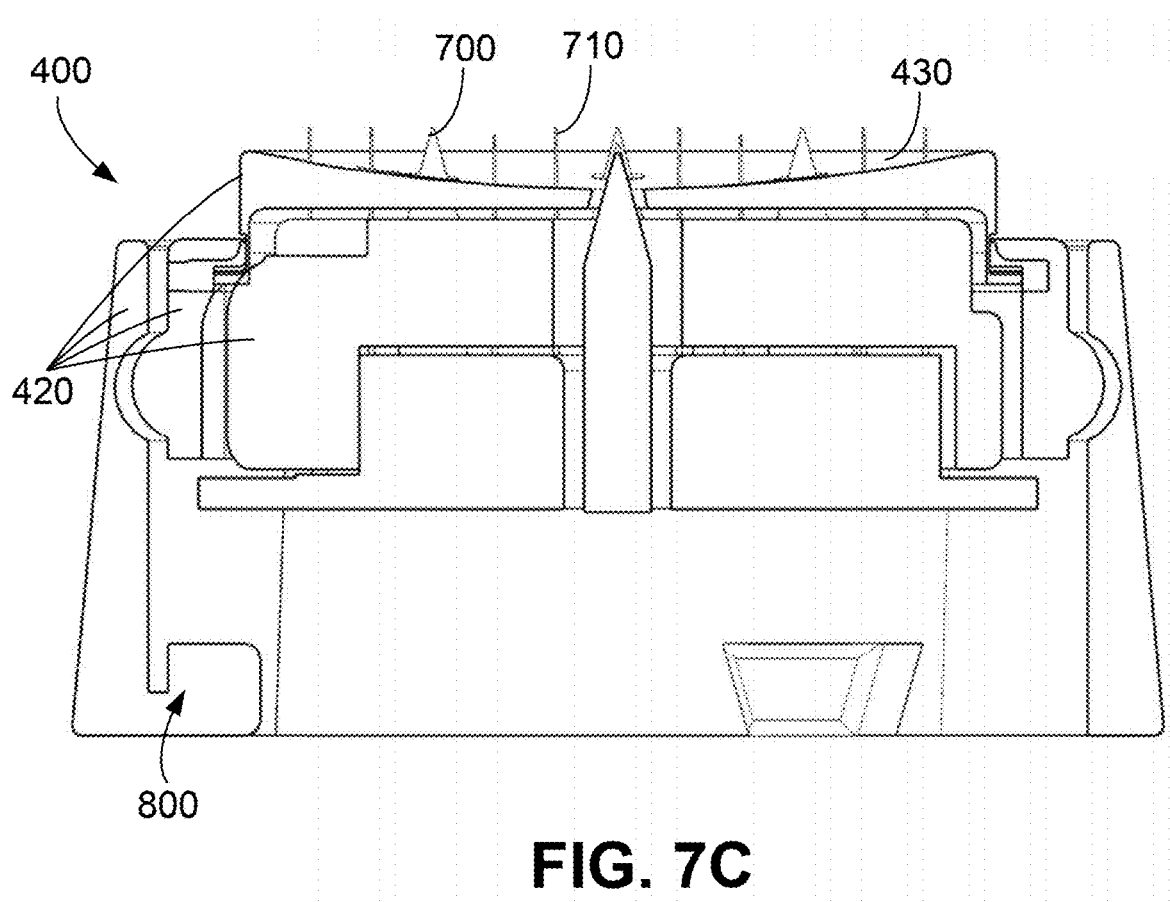
Figure 7D:
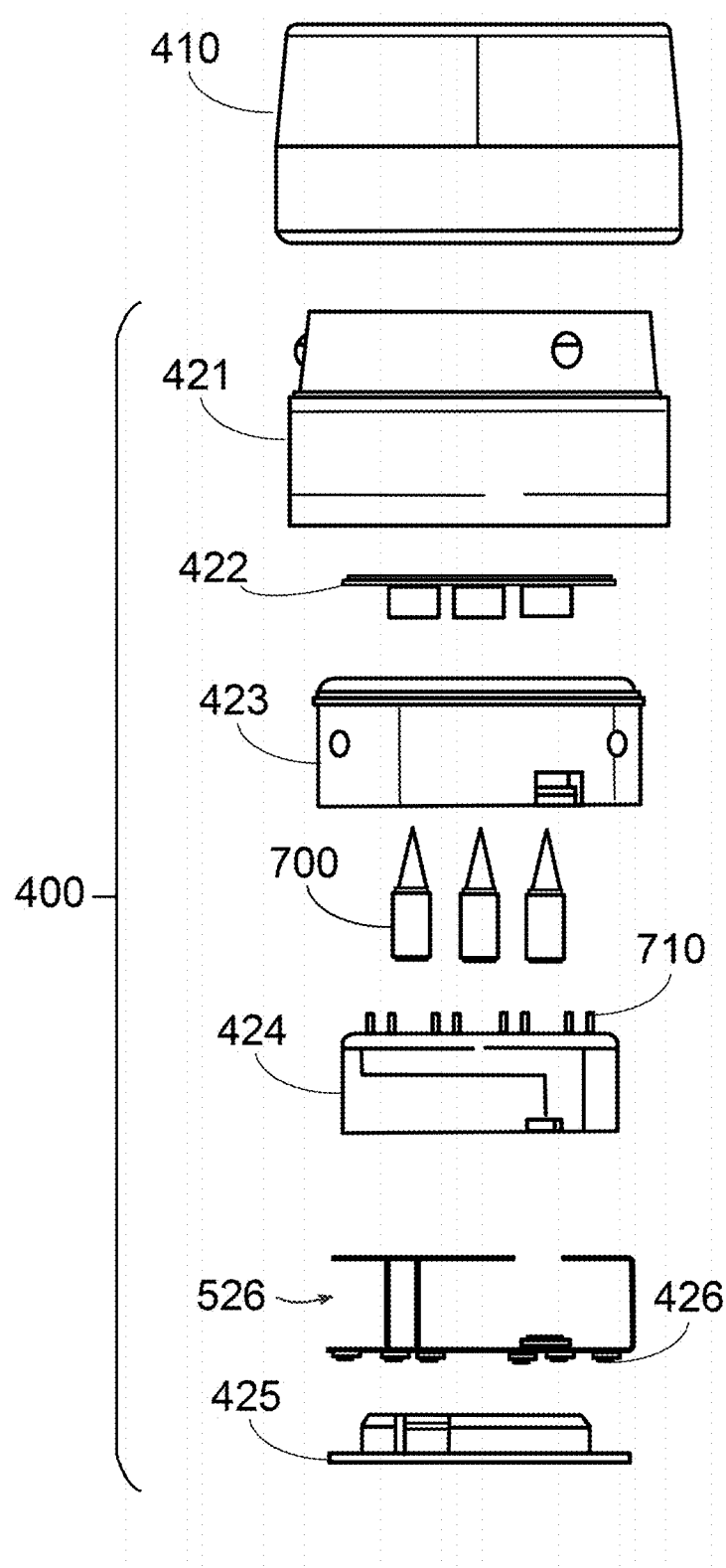

Examples of portions of the re-use prevention mechanism 800 are further shown in FIGS. 6B and 7C. In these examples, and as further illustrated in the example shown in FIGS. 11A-11D, the first portion 810 is a breakable re-use prevention member that is configured to couple the cartridge 400 to the handpiece assembly 300 and configured to break in response to the cartridge 400 being removed from the handpiece assembly 300. In implementations in which the cartridge 400 is single-use, the first portion 810 can be positioned on the cartridge 400 so that the cartridge 400 cannot be reused when the first portion 810 is broken.

The first portion 810 is positioned along the outer casing 421 of the cartridge 400 and protrudes inwardly from the outer casing 421 of the cartridge 400. For example, the first portion 810 includes one or more radial protrusions 811, e.g., two or more radial protrusions, three or more radial protrusions, or more. The radial protrusions 811 are positioned on or form part of the outer casing 421. For example, the radial protrusions 811 each include a breakable or frangible portion 812 protruding radially inwardly from the outer casing 421 and an abutment member 813 extending from the breakable or frangible portion 812. The second portion 820 includes one or more slots 821 that is configured to be aligned with the radial protrusions 811 of the first portion 810. The second portion 820 further includes an abutment surface 822 configured to abut the abutment member 813 when the cartridge 400 is mounted to the handpiece assembly 300.

The radial protrusion 811 is insertable into a corresponding slot 821 on the handpiece assembly 300, e.g., on the spacer 321 of the handpiece assembly 300, when the cartridge 400 is to be mounted to the handpiece assembly 300. The radial protrusion 811 is inserted beyond a locking member 823 in the slot 821 and then is rotated such that the abutment member 813 abuts the abutment surface 822. The locking member 823 prevents the cartridge 400 from being decoupled from the handpiece assembly 300 without breaking the breakable or frangible portion 812 on the cartridge 400.

The re-use prevention mechanism 800 varies in implementations.

Figure 11A:
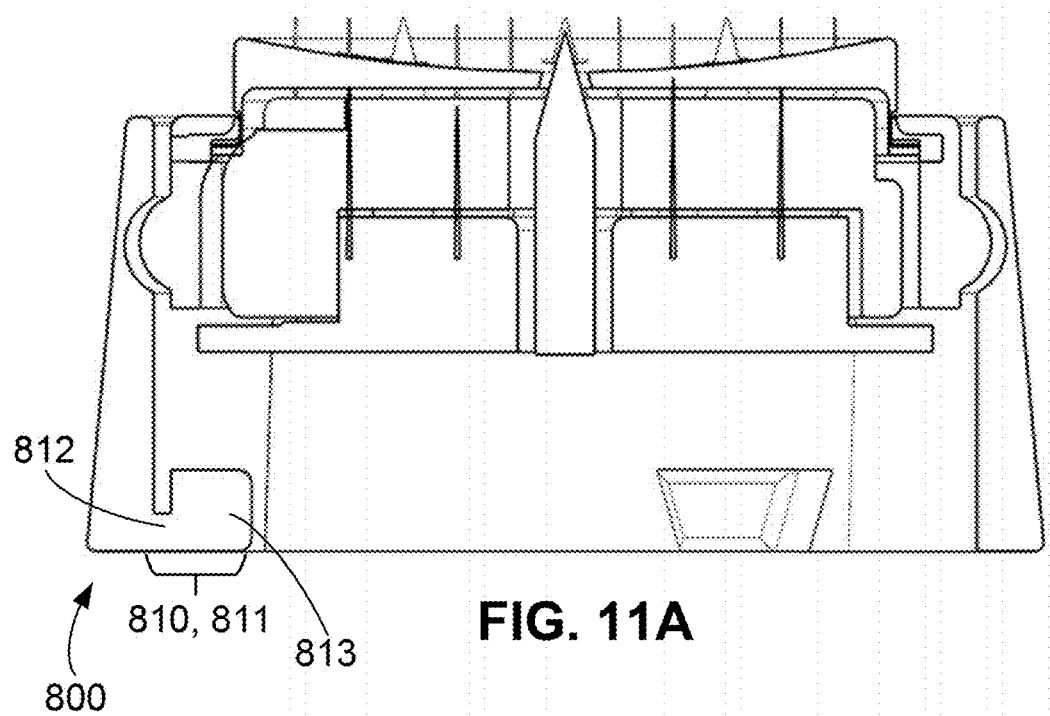
FIGS. 11A-11D are first side cross-sectional, second side cross-sectional, first perspective, and second perspective views, respectively, of an example of a re-use prevention mechanism for the cartridge of FIGS. 7A-7D.
Figure 11B:
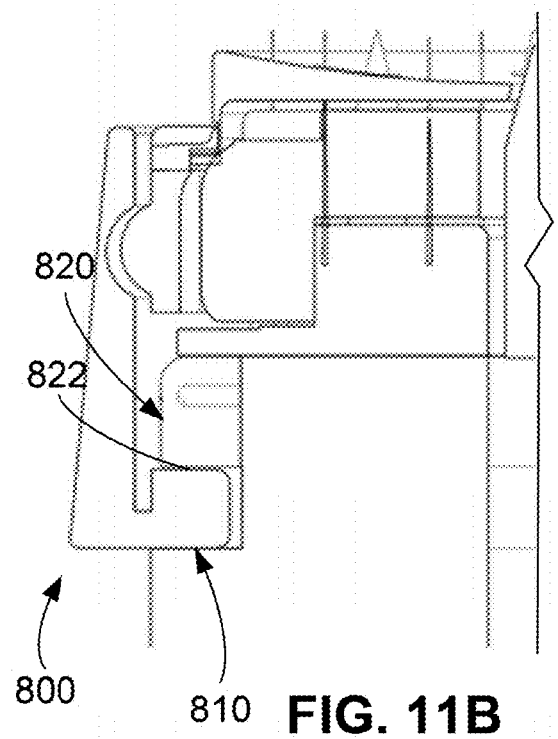
Figure 11C:
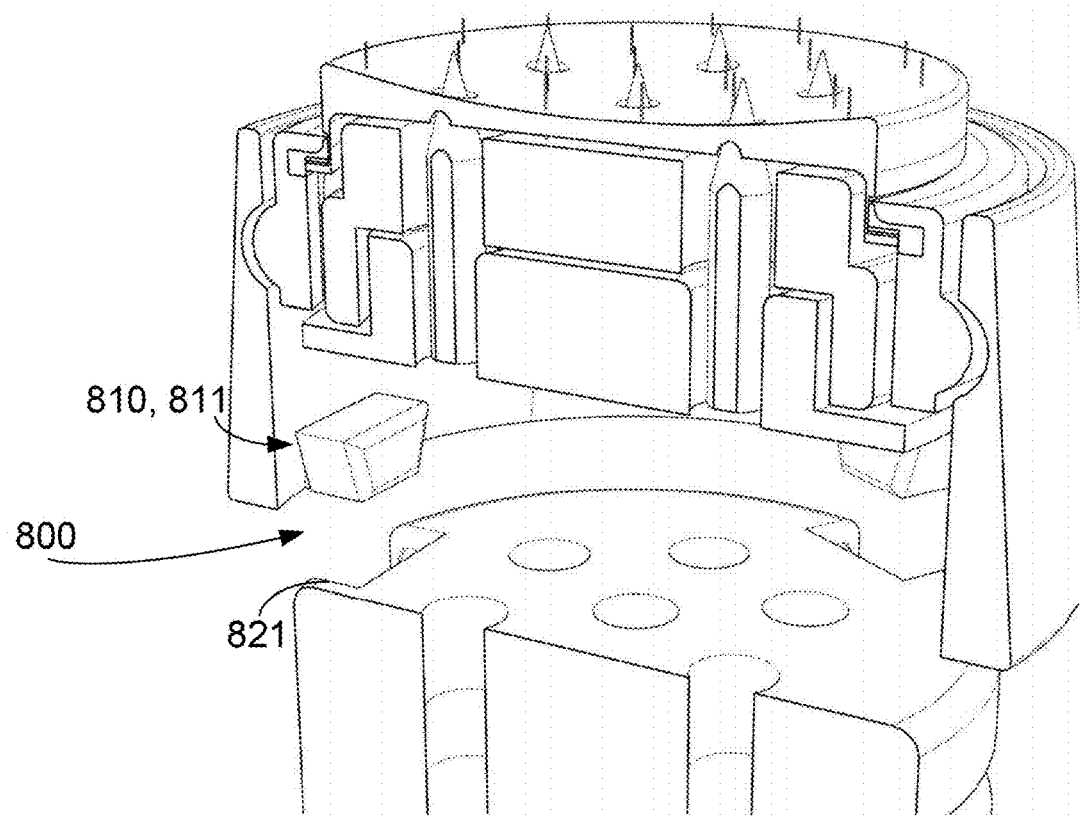
Figure 11D:
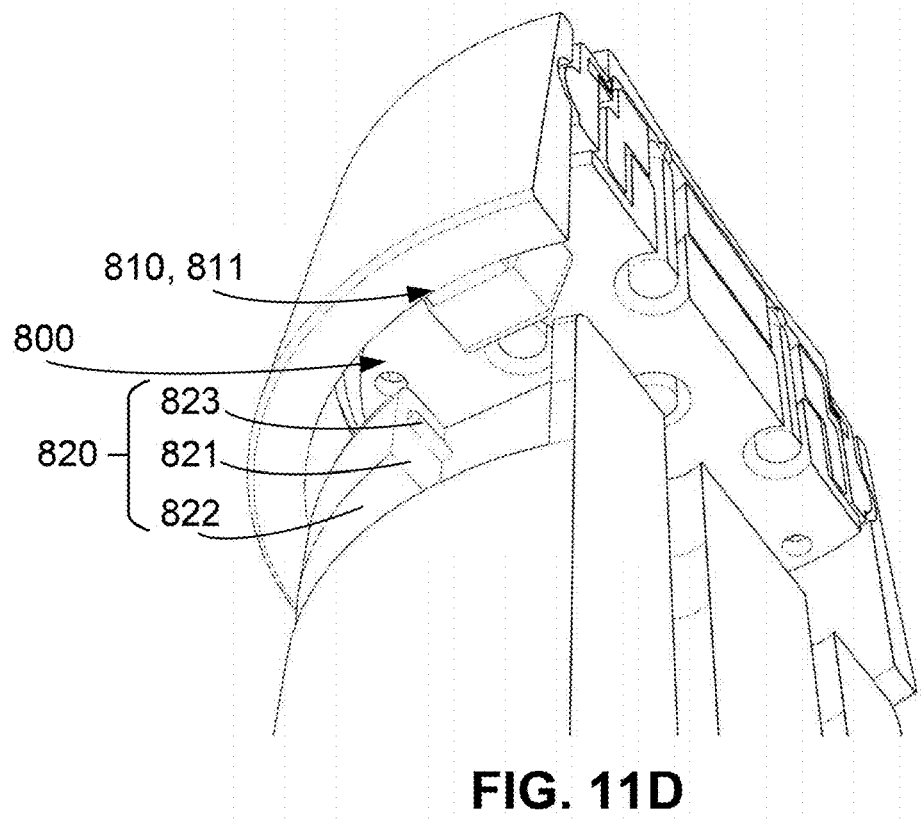
Figure 11E:
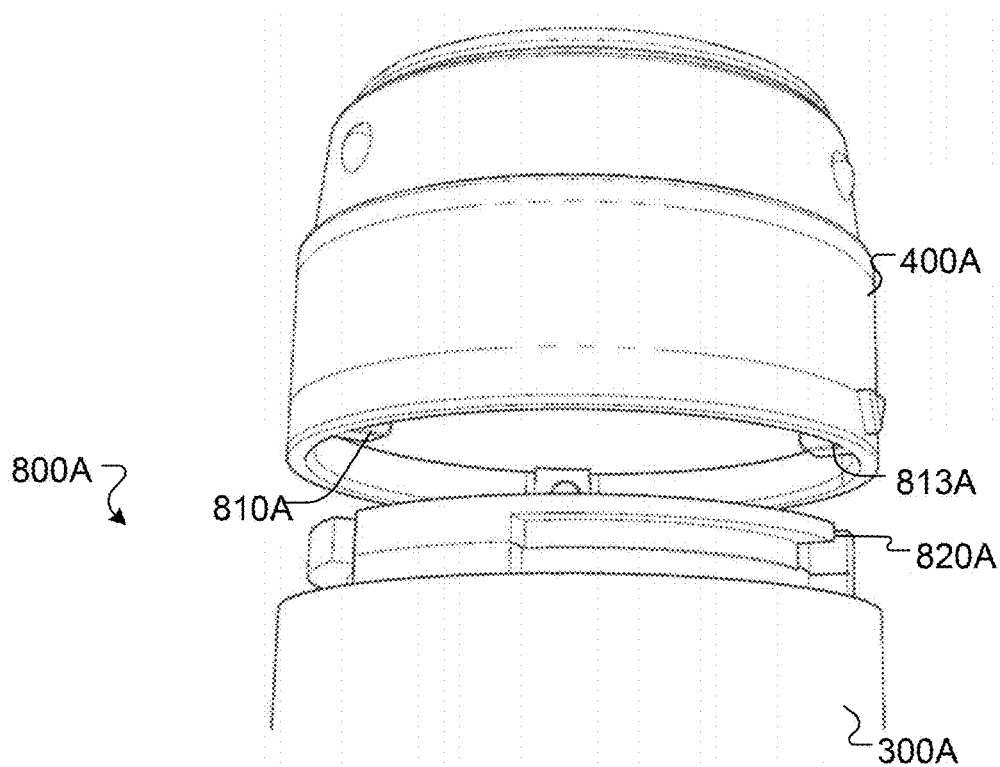
FIG. 11E is a perspective view of a different example of a mechanical alignment system for a cartridge.
Figure 11F:
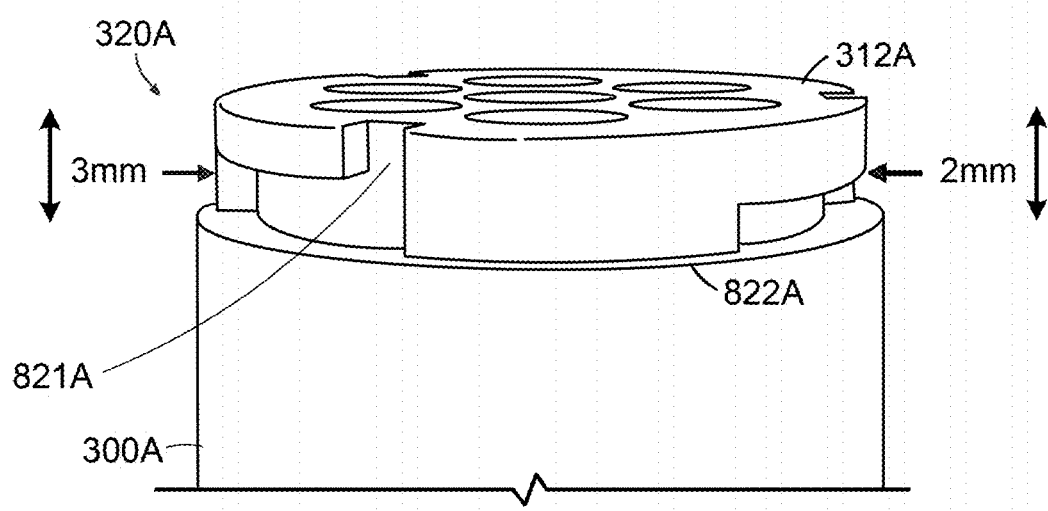
FIG. 11F is a perspective view of the mechanical alignment system of FIG. 11E on a handpiece assembly.
Figure 11G:
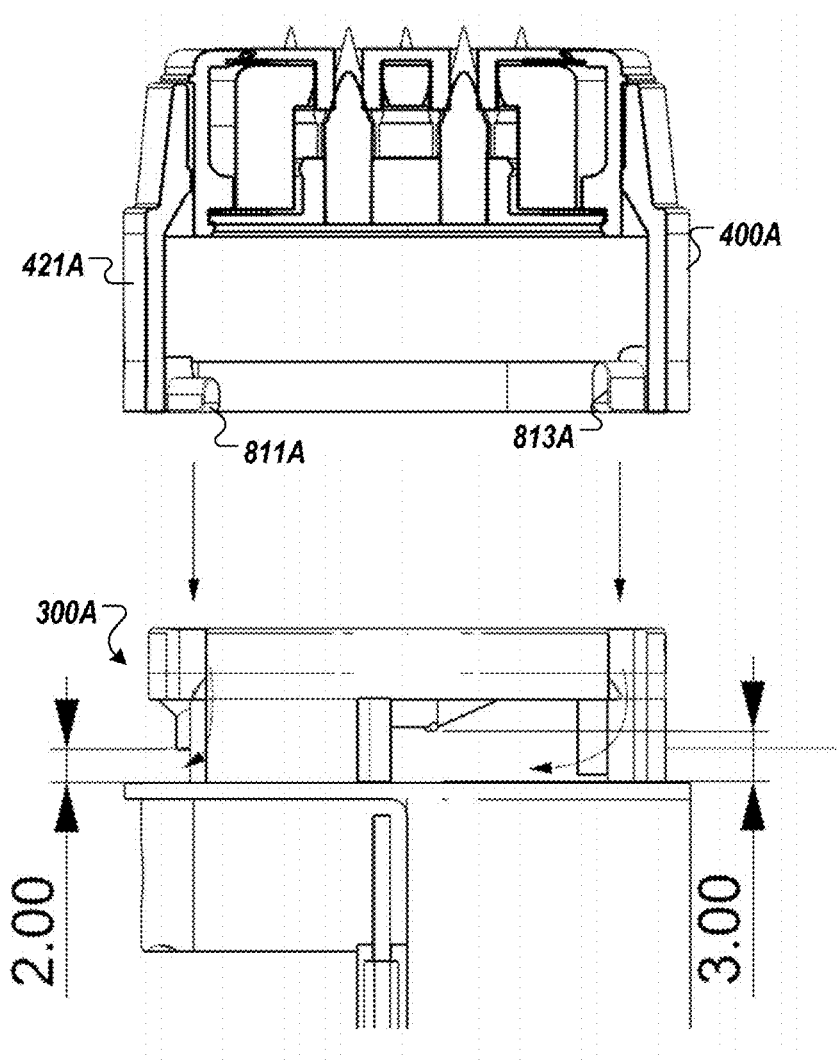
FIG. 11G is an exploded, cross-sectional side view of the mechanical alignment system of FIG. 11E.

FIGS. 11E-11G illustrate a second example of a mechanical alignment system 800A for the cartridge 400A that can be included in certain implementations. The mechanical alignment system 800A is similar to the light delivery device 100 of the previous figures. Thus, for ease of reference, and to the extent possible, the same or similar components of the second example mechanical alignment system 800A will retain the same reference numbers as outlined above with respect to the first example re-use prevention mechanism 100, although the reference numbers will be denoted with the letter 'A'. The alignment system ensures the electronic re-use prevention mechanism can work properly, i.e., the cartridge installation is proper to make the transmission of data between cartridge and handpiece.

A second portion 820A of the mechanical alignment system 800A is arranged to receive a first portion 810A of the cartridge 400A by inserting non-identical protrusions 811A, 813B formed in the outer casing 421A into slots 821A of the spacer 321A, and rotating the cartridge 400A relative to the handpiece assembly 300A to lock the cartridge 400A to the handpiece assembly 300A. The first and second portions 810A, 820A are configured to align the light source and penetrating needles before the light source can deliver any light.

As described above, cartridge installation can only be done in a specific position due to a mechanical installation assembly that ensures proper alignment. If the cartridge 400A is introduced in the wrong position, the handpiece assembly 300A cannot read properly the memory 815 of the cartridge 400A. This feature serves as a safety mechanism, as light delivery is disabled until the cartridge 400A is installed in the proper position. As described above with respect to FIGS. 10B and 10C, the cartridge sensor device 526A has two non-symmetrical points of contact 638 that need to be detected in the proper position to bypass the light delivery protection mechanism. This mechanical alignment also ensures that the light dose is delivered properly.

Figure 12A:
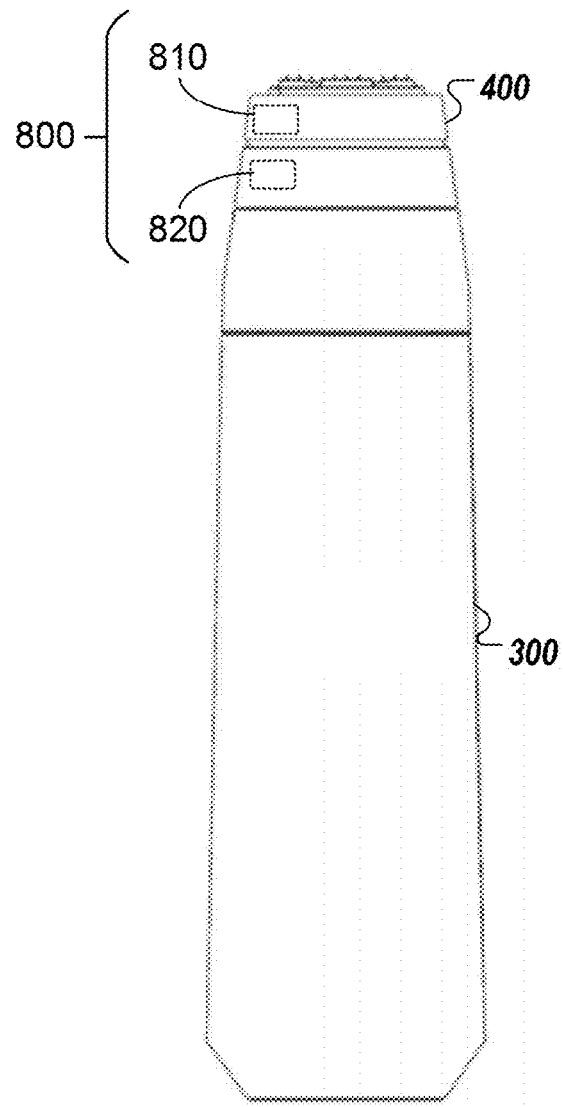
FIG. 12A is a side view of a light delivery device showing another example of a re-use prevention mechanism for a cartridge.

FIG. 12A illustrates another example of the re-use prevention mechanism 800. The first portion 810 of the re-use prevention mechanism 800 includes an electronically-readable tag positioned on the cartridge 400, and the second portion 820 of the re-use prevention mechanism 800 positioned on the handpiece assembly 300 includes an electronic reader. The electronic reader can register an identity of the cartridge 400 indicated by the electronically-readable tag. The control system of the light delivery device 100 can prevent operation of the light delivery device 100 in response to the electronic reader detecting the same identity for the cartridge 400 mounted to the handpiece assembly 300. In other words, the control system can be configured to register and check the identity of the cartridge 400 and allow only a single use of the cartridge 400.

In some implementations, the re-use prevention mechanism 800 is part of the controller 510 and includes a tracking module that monitors the number of light delivery operations executed with a particular cartridge. When the number of routines associated with a particular cartridge exceeds a threshold number, the controller 510 prevents the cartridge from being used for another light delivery operation.

Figure 12B:
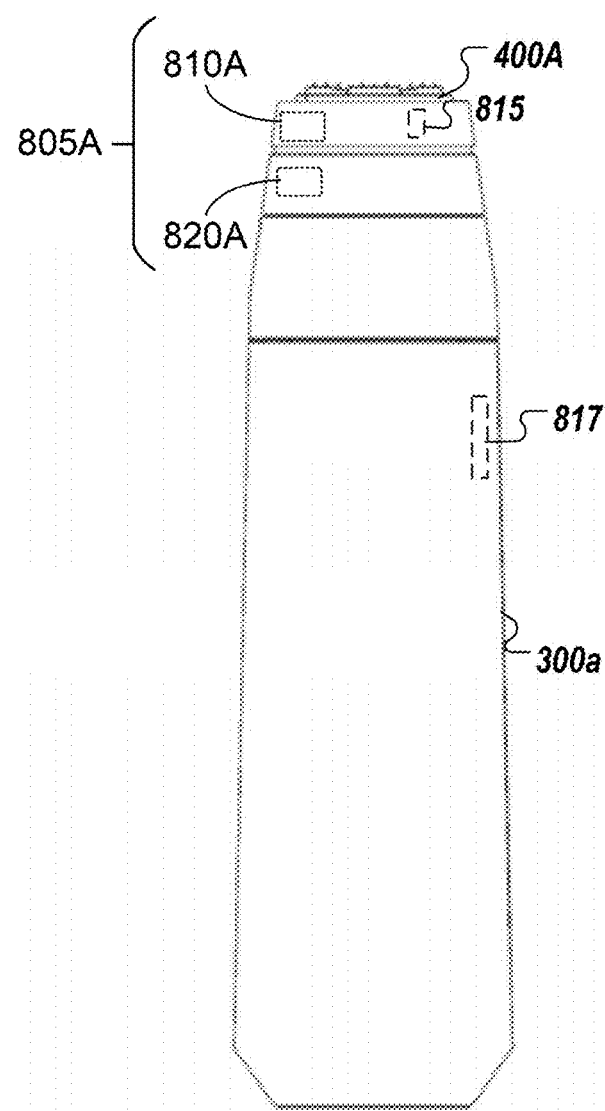
FIG. 12B is a side view of a light delivery device showing another example of a re-use prevention mechanism for a cartridge.
Figure 12C:
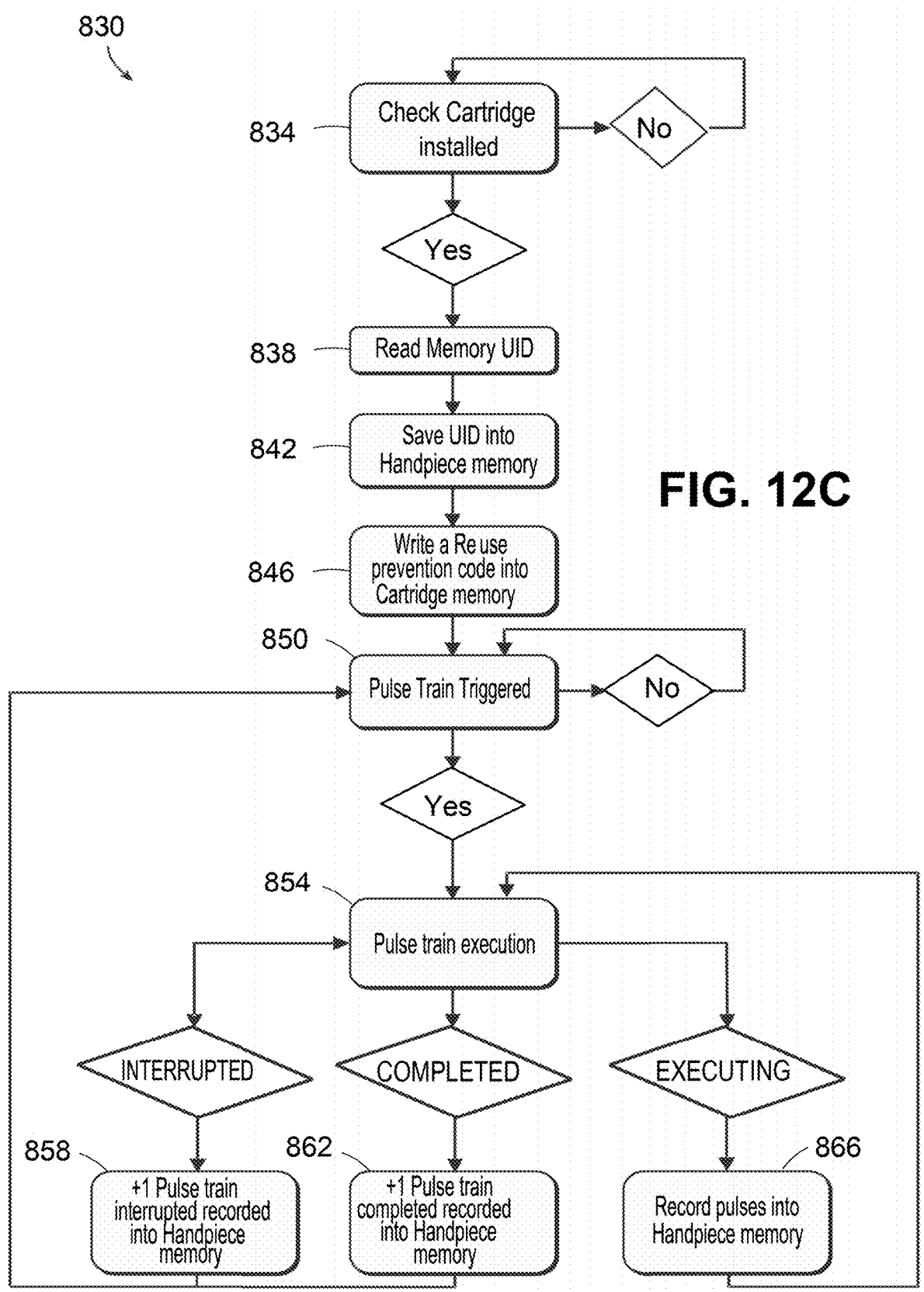
FIG. 12C is a schematic flow chart of a method of using the re-use prevention mechanism of FIG. 12B.

FIG. 12B depicts a different example electronic re-use prevention mechanism 805A, and will be described with reference to a method 830 in FIG. 12C. The electronic re-use prevention mechanism 805A includes a unique ID ("UID") 810A built inside the cartridge 400. An EEPROM memory 815 (FIG. 12A) is disposed inside the cartridge 400, and contains a memory block code defining a UID. This memory block is written during manufacturing of the EEPROM memory and is protected from being overwritten. In other words, the user cannot modify or tamper with the UID to successfully connect a used cartridge 400 again within the device 100. Once the cartridge 400 is placed into the handpiece assembly 300, the handpiece assembly 300 writes a different memory block into the EEPROM to register that the cartridge has been used. If this cartridge 400 is used again, the handpiece assembly 300 will be able to read if that assigned memory block has been read before, and will disable the light source from being activated.

The method 830 involves reading, recording, and storing a UID of each cartridge 400 to prevent reusing any cartridge. The method 830 includes a first step 834 of checking whether the cartridge 400 is installed properly on the handle assembly 300. For example, the re-use prevention mechanisms 800, 805A and alignment system 800A described above ensure that light source and penetrating needles are aligned. A second step 838 includes reading, using a reader 820A installed in the handpiece assembly 300, the UID from the installed cartridge 400, and saving the UID to a memory 815 (e.g., EEPROM) disposed inside the cartridge 400, which contains a memory block code defining a UID. The method 830 includes a step 842 of saving the UID into a memory 817 (FIG. 12A) of the handpiece assembly 300, and a step 846 of writing a reuse prevention code into the cartridge memory 815. If, for example, the handpiece assembly 300 reads the UID of the cartridge 400 for the first time, the light delivery device 100 may be further activated. For example, the method 830 can include the step 850 of triggering a pulse train of the optical transmission system.

Additionally, and before triggering the light 850, the method 830 may perform steps to ensure safe use of the device 100. For example, the step 834 ensures that the cartridge 400 is installed properly to the handpiece assembly 300. For example, the mechanical alignment system 800A of FIGS. 11E-11G ensure that the light source and the piercing members are aligned properly. If the cartridge 400A is not aligned properly with the handpiece assembly 300A, then the light source will be disabled. After the cartridge 400 is properly installed, the handpiece assembly 300 may then detect if the cartridge is properly aligned (e.g., perpendicular to a target surface) by using the sensing system 520A of the control system 500A of FIG. 3B. The light source will remain disabled until all contact sensors 526A indicate proper alignment of the cartridge 400 with the target surface. The controller 510 then receives a signal from the sensor system that the cartridge is installed properly and that the cartridge is properly aligned with the target surface. In response, the controller 510 turns on the light source, which is turned off by default. The energy storage device is turned on, a trigger button is depressed, and the controller 510 generates a pulsed signal in step 850. In some examples, all of these conditions must be met to permit the light source from emitting light. In some examples, the delivery device 100 may include fewer or more safety precautions to enable the light source.

Returning to FIG. 12C, the steps 858, 862, and 866 are optional steps of the method 830, and may be used to collect usage data that can be stored in the handpiece assembly 300. The handpiece assembly 300A collects information about the UID of the cartridges 400A and how much they were used, number of pulse trains completed, and interrupted. This information is stored inside the device 100A. After the pulse train is executed at a step 854, the memory 817 stores all instances of interruptions 858, completed sessions 862, and while light is being delivered 866. Because a UID of a cartridge cannot be modified (it is hard coded into memory chip) the UID will remain intact even if the cartridge memory is tampered with. If the device 100A detects a cartridge 400A with a previously used UID, the device 100A can prevent certain behaviours (e.g. prevention of turning on device, prevent of emission of light).

Example Methods of Operations

The light delivery device 100 or 100A can be operated by the subject or by a user separate from the subject. In some examples, referring back to FIG. 4C, the cartridge 400 (with the cartridge cap 410) is mounted to the handpiece assembly 300. The cartridge cap 410 is then removed from the cartridge 400.

Referring to FIGS. 1A and 7B, the piercing members 120 (e.g., including optical needles 700 and/or including the mechanical needles 710) are moved to an insertion position in which the piercing members 120 are inserted into the biological surface, e.g., skin, of the subject. For example, the piercing members 120 are inserted through the surface S10 of the skin S and into the subdermal or intradermal portion S20 (including the melanin layer) of the skin S. In implementations in which the cartridge 400 or 400A is present, the cartridge 400 or 400A is placed on the skin S of the subject to insert the piercing members 120 into the biological tissue. The depth of insertion can vary in implementations, depending on a location of the target layer of biological tissue relative to the surface of the biological tissue. In some implementations, the piercing members 120 can be inserted to a depth of 0 to 3 millimeters, e.g., at least 0.1 millimeters, at least 0.3 millimeters, at least 0.5 millimeters, at least 1 millimeter, at least 1.5 millimeters, at least 2 millimeters, etc. The depth of insertion can be no more than 5 millimeters, e.g., no more than 4 millimeters, no more than 3 millimeters, no more than 2 millimeters, no more than 1 millimeter, etc.

Referring to FIGS. 1A, 3A, 3B, and 10A-C, after the piercing members 120 are inserted into the biological surface, contact between the distal surface 125 of the light delivery device 100 or 100A and the skin S can be detected, e.g., using the contact sensor device 526 or 526A. This detected contact can be used by the control system 500 or 500A as a triggering event for permitting activation of the light delivery device 100 or 100A to emit light.

Referring to FIGS. 10F-10G, an alignment of the piercing members 120 relative to the skin S is detected using the contact sensors 527A of the device 526A before enabling light delivery. The control system 500A measures the alignment between each contact sensor 527A and the skin to determine whether the device 100A is properly aligned. The control system 500A delivers "correct alignment" or "incorrect alignment" signals to the display module 540A.

After proper contact is detected, referring to FIGS. 1A and 4B, delivery of light from the light delivery device 100 or 100A is initiated. The delivery of the light can be initiated in response to detecting the contact between the cartridge 400 or 400A and the skin S of the subject. In some implementations, a user can further press a button to initiate the delivery of the light. Furthermore, in some implementations, the delivery of light can be initiated only if a cartridge is attached to the handpiece assembly 300 or 300A, e.g., as discussed in connection with the cartridge detection sensor 524 or 524A (shown in FIGS. 3A and 3B). The light source 110 of the handpiece assembly 300 or 300A of the light delivery device 100 or 100A can be activated to emit light through the optical transmission system 320 and then through at least some of the piercing members 120 of the cartridge 400 or 400A, as described in this disclosure. An amount of power delivered to each piercing member 120 or to each optical needle 700 can be at least 1 mW, e.g., at least 2 mW, at least 3 mW, or more. The user can cause activation of the light source 110 by operating the button 102 to turn on the light delivery device 100 or 100A and then operating the button 104 to activate the light source 110. The user can further interrupt and stop delivery of light by the light source 110 by operating the button 102 during a light delivery routine.

The light can be delivered in pulses. For example, a pulse width of the light delivery can be 10 to 500 milliseconds. 10 to 100 pulses can be delivered per site of treatment by the light delivery device 100, and then the light delivery device 100 can be moved to another site to deliver treatment. A total duration for each site of treatment can be in a range of approximately 1 second or more (e.g., about 5 seconds or more, about 10 seconds or more, about 15 seconds or more, about 20 seconds or more, about 25 seconds or more, about 30 seconds or more) to approximately 60 seconds or less (e.g., about 55 seconds or less, about 50 seconds or less, about seconds or less, about 40 seconds or less, about 35 seconds or less), and, when used to promote hair regrowth on the head, the light delivery device 100 can be used at 10 to 200 sites of treatment, e.g., 10 to 30, 20 to 40, 30 to 50, 30 to 100, 30 to 150, 50 to 150, etc., sites of treatment.

After the light is delivered from the light delivery device 100 or 100A, the cartridge 400 or 400A is removed from the handpiece. Using the re-use prevention mechanism 800 or 805A, the cartridge 400 or 400A is prevented from being re-used with the handpiece assembly 300 or 300A. For example, the re-use prevention mechanism 800 or 805A can prevent the cartridge 400 or 400A from being attached to the handpiece assembly 300 or 300A in response to removing the cartridge 400 or 400A from the handpiece assembly 300 or 300A and/or storing the UID of the cartridge 400A in the handpiece memory 817. The light delivery device 100 or 100A and the methods 830 of using the light delivery device 100 or 100A can be used for treating a variety of conditions and delivering a variety of therapies. In some implementations, the light delivery device 100 is used to deliver light to the subdermal or intradermal portion of skin of the subject to promote hair growth. In further implementations, the light is delivered to relieve musculoskeletal pain. The light delivery device 100 can be used to treat conditions, relieve somatosensory issues, or relieve pain associated with muscular, neuromuscular, and pain-related disorders, carpal tunnel, bruxism, temporomandibular joint disorder, tension headaches, migraines, chronic pain, tendonitis, joint injuries (e.g., a rotator cuff injury), inflammation, numbness or loss of sensation, muscle stiffness, muscle spasms, post-surgery pain, carpal tunnel syndrome, pain associated with scoliosis, dermatitis, arthritis, or other skin conditions. In some implementations, the light delivery device 100, 100A is used to facilitate re-learning of motor control. In some implementations, the light delivery device 100 is used to activate photoactivated drugs that are separately placed into physiological systems of the subject. In some implementations, the light delivery device 100 is used to treat dermatological conditions, provide wound therapy, burn therapy, sunburn therapy, or achieve aesthetic outcomes, e.g., fractional treatment of the skin, hair removal/reduction, skin resurfacing, vaginal rejuvenation, facilitate healing of cold sores, body contouring, lipolysis of subdermal fat, reduction in body part circumference (e.g., waist size, arm size, leg size, etc.), increase in local blood circulation, coagulation and procedures, treatment of onychomycosis, increase clarity of nails. In further implementations, the light delivery device 100 is used to provide treatment or relief from hyperhidrosis or hypohydrosis, rhytids, wrinkles, acne, acne scars, acne vulgaris, chronic wounds, burn scars, psoriasis, eczema, dermatitis, allergic dermatitis, vitiligo, warts, hypertrophic and keloid scars, benign pigmented lesions, deformative scars including scars limiting the mobility of extremities and face, tattoos, pigmented lesions, spots, freckles, macules, skin tags, or keratosis, blisters, calluses, superficial veins and angiomas, spider veins, rosacea, venus lake, nevis, leg veins, birthmarks, hemangiomas, telangiectasias, port wine stains, other vascular lesions and blemishes, cellulite, collagen induction, increase in collagen production, increase of epidermal and/or dermal thickness, skin rejuvenation, fat-related dysmorphia, lupus scars, pityriasis versicolor, pityrasis alba, nevus anemicus, or chemo-related hair loss. In some implementations, the light delivery device 100 can be used to speed up muscle recovery after exercise.

Further Alternative Implementations

A number of implementations have been described. While this specification contains many specific implementation details, these should not be construed as limitations on the scope of what is being claimed, which is defined by the claims themselves, but rather as descriptions of features that may be specific to particular implementations of particular inventions. It will be understood that various modifications may be made.

As described in this disclosure, in some implementations, the wavelength of the light emitted by the light source 110 can be between 280 nanometers and 3000 nanometers. The light source 110 can be configured to emit a single or multiple wavelengths, or a range, spectrum, or bandwidth of wavelengths of light. The light source 110 can include one or more broadband light sources, LEDs, lasers, or laser diodes having various emission wavelength profiles. In some implementations, the light delivery device 100 can include a filter to eliminate part of a spectrum of light emitted by the light source 110. The filter can allow for passage of a part of the spectrum and filter out another part of the spectrum. In some implementations, the light source 110 may provide multiple colors and/or wavelengths through the same piercing or penetrating member (e.g., needle), or may alternate between multiple colors and wavelengths through the same needle. In some implementations, the light source 110 may provide multiple colors and/or wavelengths through the multiple, separate needles, or may alternate between multiple colors and wavelengths through multiple, separate needles.

The light delivery device 100 is described as including the cartridge assembly 415 and the handpiece assembly 300. In some implementations, the light delivery device 100 includes only the handpiece assembly 300. In these implementations, the light delivery device 100 does not include a separate cartridge assembly. The piercing members of the light delivery device 100 are integral to the light delivery device 100 and are not part of a removable cartridge assembly. In such implementations, components that are described as being part of the cartridge assembly 415 are integrated into the light delivery device 100 (e.g., integrated into the handpiece assembly 300). The light delivery device 100 in these implementations can be a multi-use device with piercing members that can be cleaned and disinfected or sterilized for re-use.

In implementations in which the cartridge assembly 415 is present, elements of the handpiece assembly 300 can be integrated into the cartridge assembly 415 rather than integrated into the handpiece assembly 300. For example, the optical transmission system 320 is described as being integrated into the handpiece assembly 300. In some implementations, the optical transmission system 320 is integrated into the cartridge assembly 415 and thus is removable from the handpiece assembly 300 with removal of the cartridge assembly 415 from the handpiece assembly 300. Similarly in some implementations, elements of the cartridge assembly 415 can be integrated into the handpiece assembly 300 rather than integrated into the cartridge assembly 415. For example, in some implementations, the cartridge assembly 415 includes only the optical needles 700 or only the mechanical needles 710, and the handpiece assembly 300 includes the other needles, e.g., the needles that are not present on the cartridge assembly 415. In some implementations, the contact sensor device 526 is integrated into the handpiece assembly 300 so that the contact sensor device 526 is not removed from the handpiece assembly 300 with removal of the cartridge assembly 415 from the handpiece assembly 300.

The system 200 is described as including the light delivery device 100 and the charging station 250. Alternatively or additionally, in some implementations, the light delivery device 100 can be directly charged by being plugged into a standard AC outlet. In some implementations, the light delivery device 100 does not include an energy storage device and is drawing energy from an external energy source. For example, the external energy source can be the power grid, and the light delivery device 100 can be plugged directly into a standard AC outlet to draw energy from the power grid. The external energy source can alternatively or additionally be a power pack that the light delivery device 100 can be electrically connected to. In some implementations, rather than the light delivery device 100 being placed onto the charging station 250, the external energy source (e.g., a power pack) can be placed onto the charging station 250 to enable the external energy source to be re-charged.

While the control systems 500 and 500A are described as including the energy storage device 140, the controller 510, the sensor system 520 or 520A, the optical system 530, and the indicator 540 or 540A, in implementations, one or more of these sub-systems of the control system 500 or 500A can be excluded. For example, in some implementations, the control system 500 or 500A can include the controller 510 or 510A, the sensor system 520 or 520A, and the optical system 530 but does not include the energy storage device 140 or the indicator 540 or display module 540A. In some implementations, the control system 500 or 500A can include the controller 510 or 510A and the optical system 530, but does not include the energy storage device 140, the indicator 540, display module 540A, or sensor system 520 or 520A. In some implementations, the sensor system 520 or 520A only includes a subset of the sensors described in this disclosure (e.g., a subset of the buttons 102, 104, the charge lock sensor 522, the cartridge detection sensor 524 or 524A, and the contact sensor device 526 or 526A). In some implementations, the sensor system 520 or 520A only includes a single multi-functional button that can be used to control powering on or off of a light delivery device, initiation of light delivery, interruption of light delivery, and other operations of the light delivery device.

The piercing members 120 are described as corresponding to all or a subset of the piercing members 120 of the light delivery device 100 or 100A. In implementations, the only piercing members of the light delivery device 100 or 100A can be optical needles, and mechanical needles that are opaque to light are absent from such an example of the light delivery device 100 or 100A.

The optical system 600 is described as including the light source 110, the optical needles 700, and the optical transmission system 320. In some implementations, the optical transmission system 320 is absent from the light delivery device 100. The light emitted by the light source 110 can be transmitted through free space into the proximal ends of the optical needles 700.

The form factor of the light delivery device 100 or 100A can vary in implementations. For example, FIGS. 1-12C are described in connection with the light delivery device 100 or 100A, which is placed against the skin surface and then activated to deliver light while the light delivery device 100 or 100A remains stationary. In further examples described below, piercing members are similarly inserted into a subsurface layer of biological tissue, such as the melanin layer, and then light is delivered through the piercing members to the subsurface layer of biological tissue. These examples of light delivery devices can include structural, control, and optical components similar to those described in connection with the light delivery device 100 (e.g., the control system 500 and its subsystems).

Figure 13A:
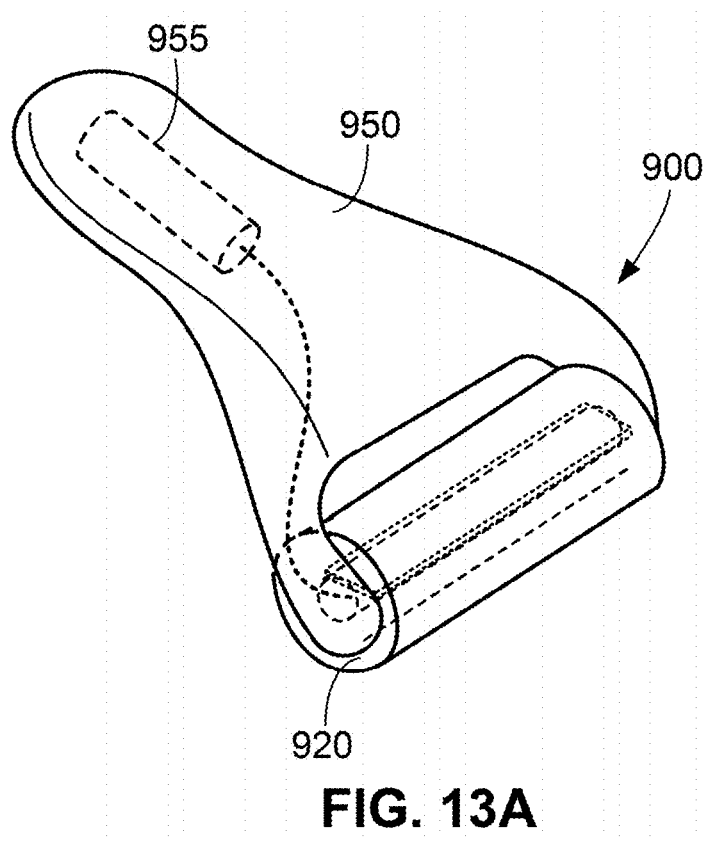
FIG. 13A is a perspective view of another example of a light delivery device.
Figure 13C:
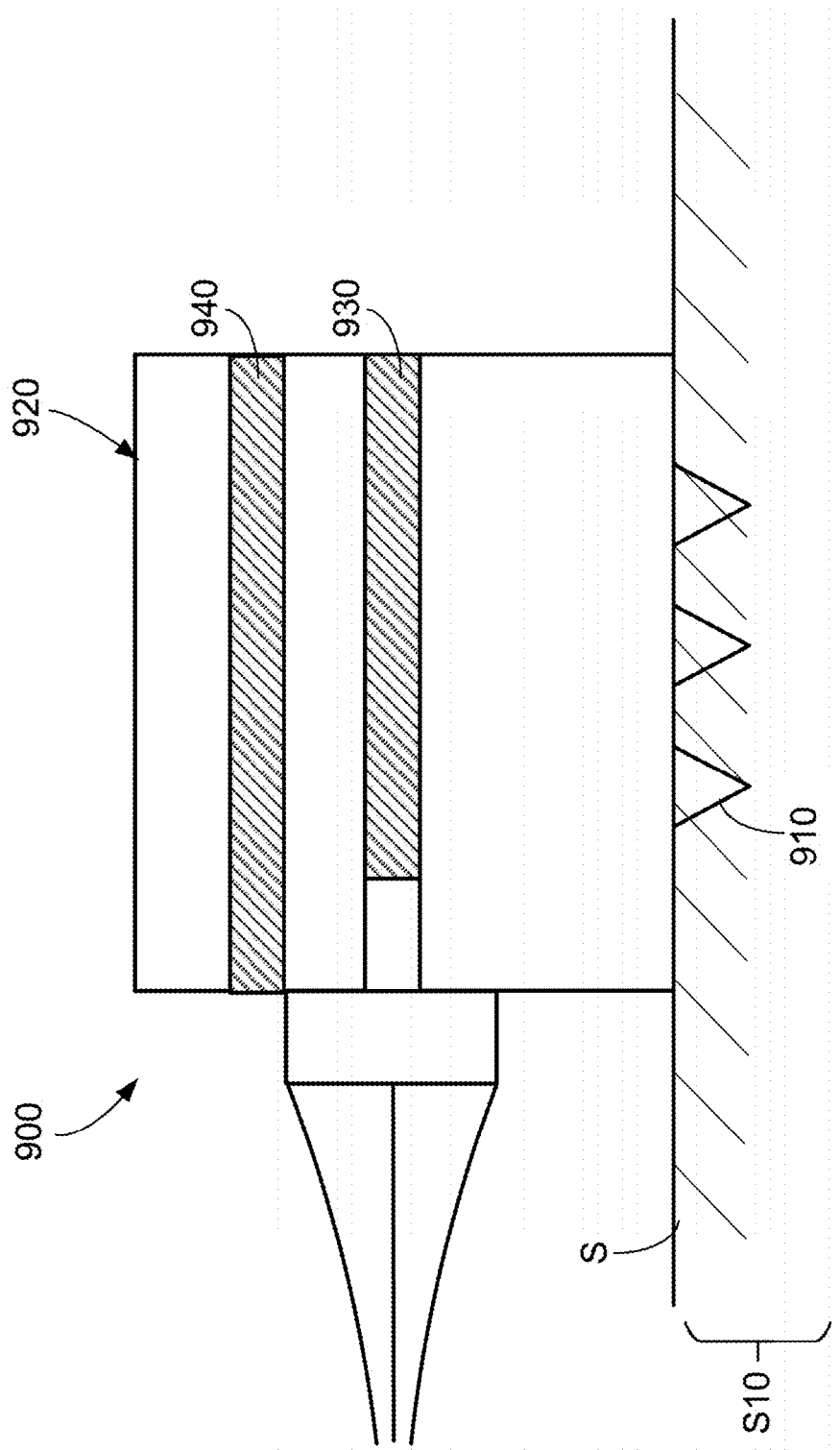

FIGS. 13A-13C illustrate an example of a light delivery device 900 with a form factor and a mechanism of operation that differ from the light delivery device 100. Rather than being stamped or pressed on a subject, the light delivery device 900 includes a rollable portion that is rolled or rotated along a biological surface, e.g., the skin, to cause the piercing members of the light delivery device 900 to puncture the biological surface.

The light delivery device 900 includes piercing members 910 and a roller 920 on which the piercing members 910 are positioned. The example of the light delivery device 900 of FIGS. 13A-13C differs from the light delivery device 100 in the way that the piercing members 910 of the light delivery device 900 are inserted into the skin S. The roller 920 is rollable on the skin S about a rotational axis to cause the piercing members 910 to puncture the skin S. When placed against the skin S, the piercing members 910 extend into the subdermal or intradermal portion S10 of the skin S. The light delivery device 900 can include a control system similar to the control system 500 described in connection with the light delivery device 100 and further include a handpiece assembly 950 that includes a light source 955 (similar to the light source 110) and that is reusable. The light delivery device 900 can further include a cartridge assembly that is single-use. The cartridge assembly can include the piercing members 910. The cartridge assembly can be in the form of an outer shell that is attachable to the roller 920 or can correspond to an entirety of the roller 920. Furthermore, the light delivery device 900 operates in a manner similar to the light delivery device 100 in that light is delivered to the target layer of tissue through the piercing members 910.

In the example shown in FIGS. 13A-13C, the light delivery device 900 includes a fiber optical cable 930 extending through a rotational axis of the roller 920 and a mirror 940 positioned around at least part of the fiber optical cable 930. An outer surface of the roller 920 is light-transmissive such that light is transmitted through both the outer surface of the roller 920 and the piercing members 910. The mirror 940 is positioned to direct the light through the piercing members 910 and into the subdermal or intradermal portion S10 of the skin S.

Figure 14A:
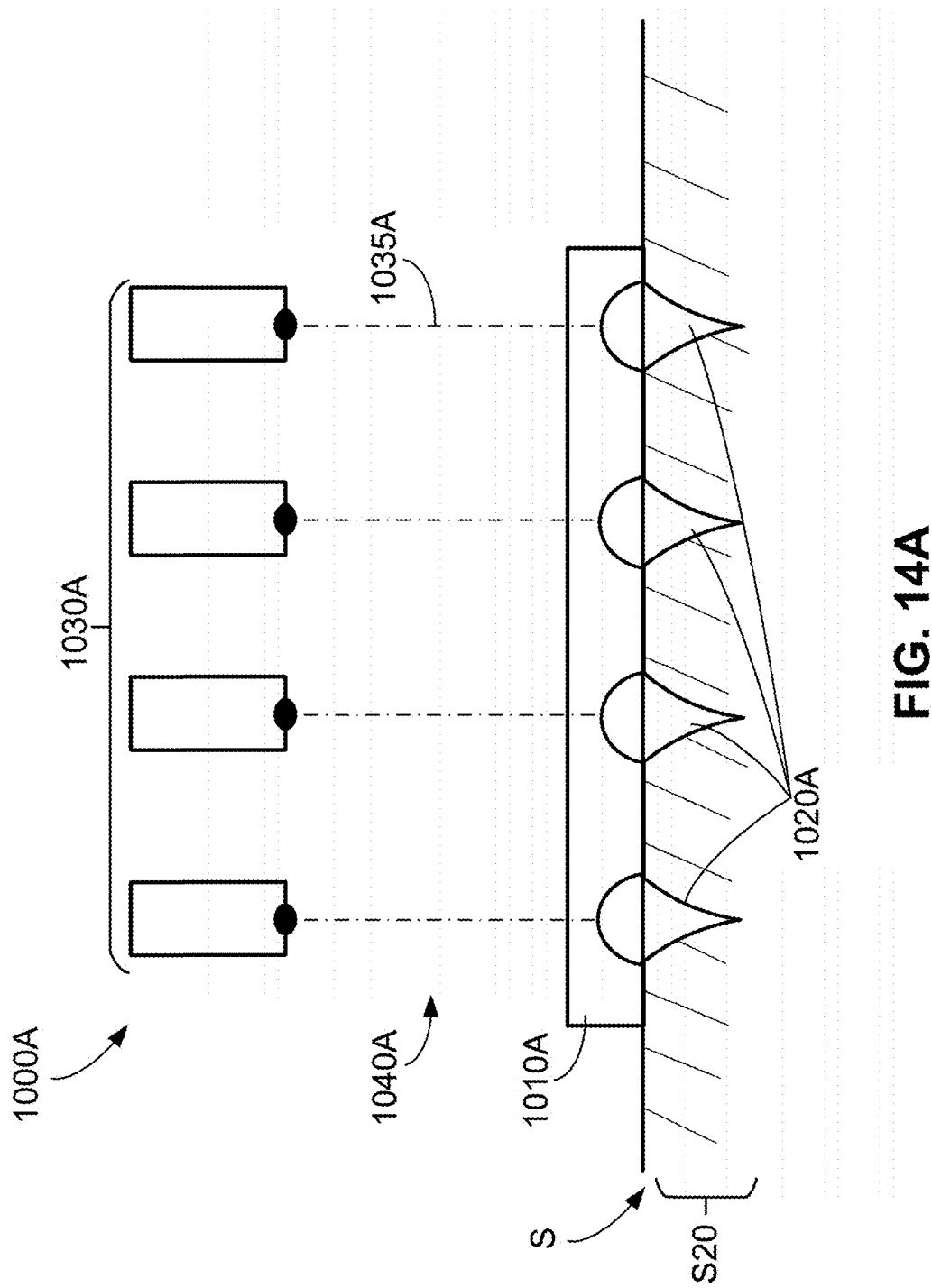
Figure 14C:
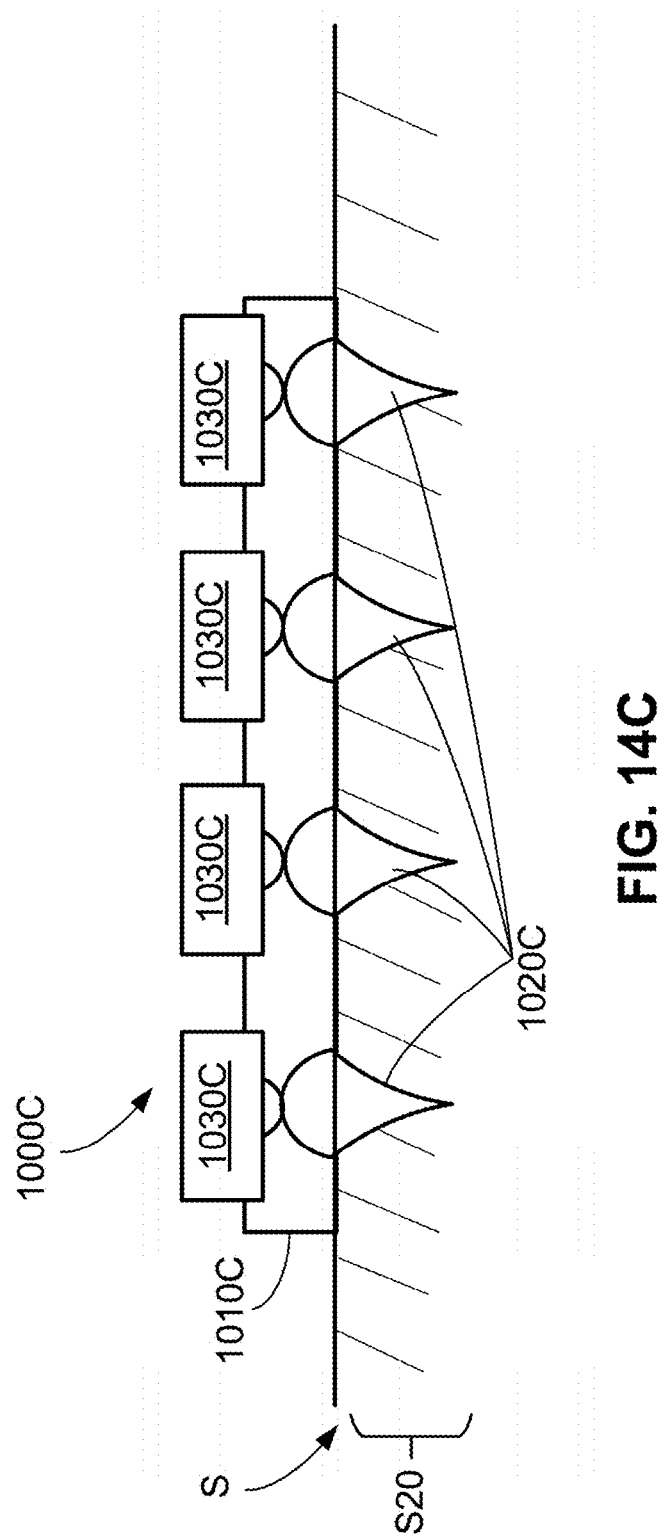

FIGS. 14A-14C illustrate further examples of light delivery devices 1000A, 1000B, 1000C with a form factor and a mechanism of operation that differ from the light delivery device 100. The light delivery devices 1000A, 1000B, 1000C include patches including surfaces that are affixed to the skin and that include piercing members that penetrate the skin when the surface is affixed to the skin. The light delivery devices 1000A, 1000B, 1000C include substrates 1010A, 1010B, 1010C (e.g., transparent substrates) and piercing members 1020A, 1020B, 1020C protruding from the substrates 1010A, 1010B, 1010C. Patch portions of the light delivery devices 1000A, 1000B, 1000C include the substrates 1010A, 1010B, 1010C and the piercing members 1020A, 1020B, 1020C. The patch portions of the light delivery devices 1000A, 1000B, 1000C can be affixed to the skin. For example, the substrates 1010A, 1010B, 1010C can be affixed to the skin S in a position such that the piercing members 1020A, 1020B, 1020C penetrate the skin S into the subdermal or intradermal portion S20 (including the melanin layer) of the skin S.

The examples of FIGS. 14A-14C differ from one another in the way that light is delivered to the piercing members. In FIG. 14A, light sources 1030A emit light 1035A through free space 1040A, through the substrate 1010A, and into the piercing members 1020A. The light sources 1030A are separate from the patch portion of the light delivery device 1000A. In FIG. 14B, light sources 1030B emit light through fiber optics 1040B, through the substrate 1010B, and into the piercing members 1020B. The fiber optics 1040B can be removably or integrally coupled to the patch portion of the light delivery device 1000B to allow for delivery of light to the piercing members 1020B. In FIG. 14C, light sources 1030C are integral to the light delivery device 1000C, e.g., integral to the patch, and include individual light sources corresponding to each of the piercing members 1020B.

Figure 15A:
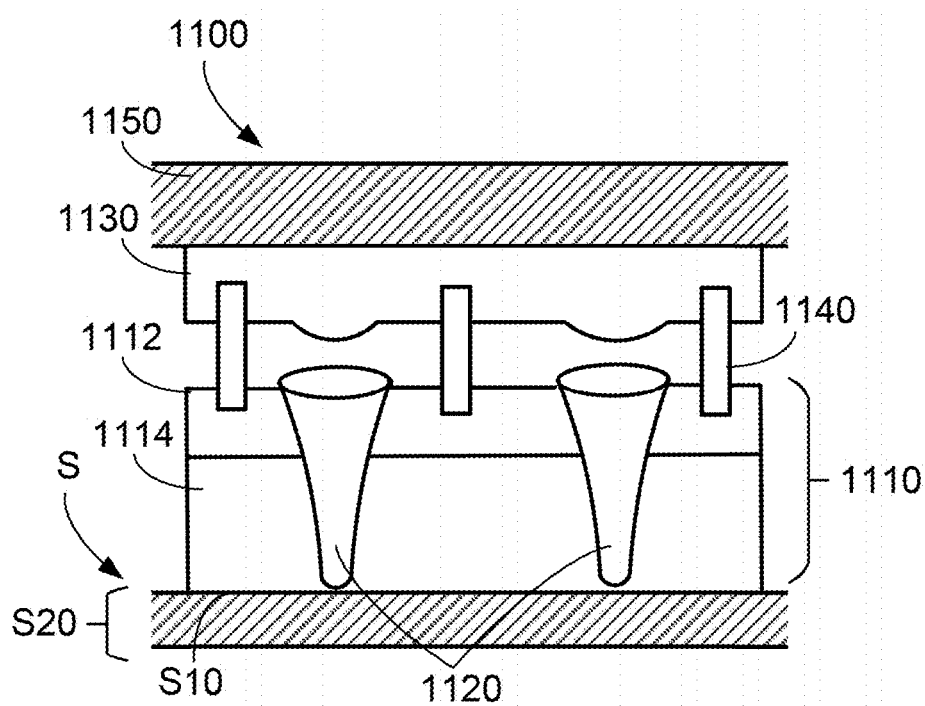
Figure 15B:
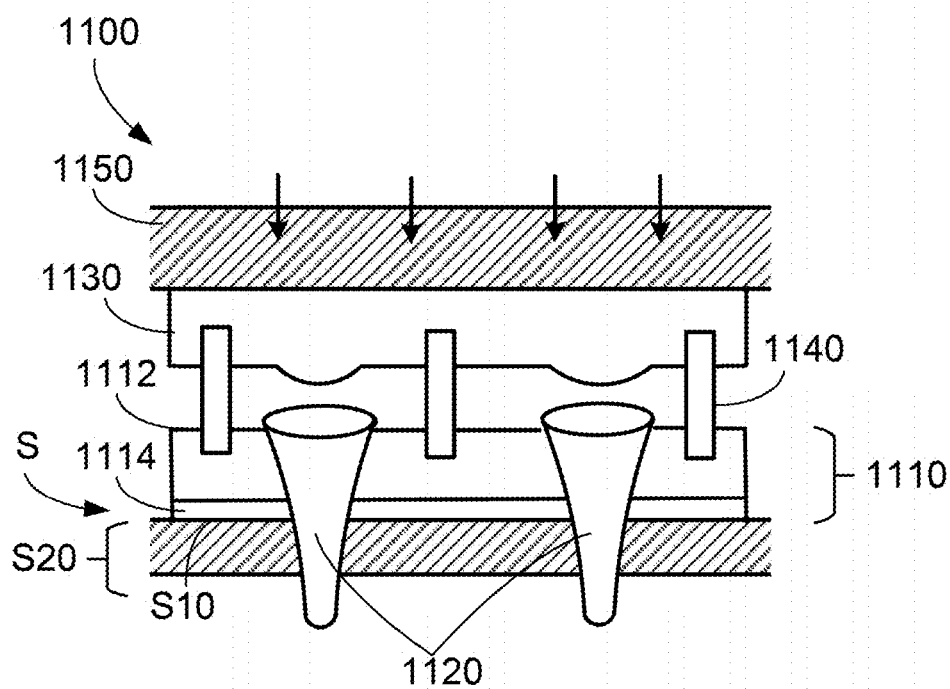

FIGS. 15A-15B illustrate another example of a light delivery device 1100 including a patch. The light delivery device 1100 includes a substrate 1110 (e.g., a transparent substrate) including a support portion 1112 and a collapsible portion 1114 positioned on the support portion 1112. The support portion 1112 can be a rigid plate for supporting piercing members 1120. The piercing members 1120 are mounted to the support portion 1112 and protrude into the collapsible portion 1114. The piercing members 1120 protrude through only part of the collapsible portion 1114 such that the collapsible portion 1114 prevents inadvertent pricking of a user by the piercing members 1120.

The light delivery device 1100 further includes an array of light emitters 1130 positioned above the substrate 1110 and aligned with the substrate 1110 via alignment members 1140, e.g., pins, protrusions, beams, or other structures for aligning the light emitters 1130 to the substrate 1110 and hence relative the piercing members 1120. The light emitters 1130 are configured to emit light through the substrate 1110, through the piercing members 1120, and into the skin S when the piercing members 1120 are inserted into the subdermal or intradermal portion S20 (including the melanin layer) of the skin S. The light delivery device 1100 further comprises a user-operable cap 1150 positioned above the light emitters 1130. The substrate 1110, the alignment members 1140, the light emitters 1130, and the cap 1150 form a stack, thus allowing force applied to the cap 1150 to be transferred to the underlying components.

To use the light delivery device 1100, as shown in FIG. 15A, a user can position the substrate 1110 on the surface S10 of the skin S. As shown in FIG. 15B, the user can then push down on the cap 1150 to cause the collapsible portion 1114 to collapse or compress and thereby cause the piercing members 1120 to puncture through the collapsible portion 1114 and into the skin S. The light emitters 1130 can then be activated to emit light through the substrate 1110, through the piercing members 1120, and then into the subdermal or intradermal portion S20 (including the melanin layer) of the skin S.

In the examples described with respect to FIGS. 1-12C, the cartridge 400 is mounted to the handpiece assembly 300, and then the user places the assembled light delivery device 100 against the skin S to cause the piercing members 120 to penetrate the skin S. In some implementations, a light delivery device can include one or more actuators that cause the piercing members to move relative to a portion of the light delivery device to be inserted into the skin. The one or more actuators can be cyclically activated to cause a reciprocal motion of the cartridge. For example, the one or more actuators can be actuated to cause motion of the cartridge of the light delivery device relative to the handpiece assembly of the light delivery device. The one or more actuators include, for example, an electromechanical actuator, a magnetic actuator, a motor, a rotary motor, a linear motor, a pneumatic or hydraulic actuator, a thermally-activated actuator, or another actuator for causing motion of the cartridge. Triggering of the one or more actuators can involve manual operation of a user (e.g., using a button or switch), generation of signals by the control system of the light delivery device, and/or actuation of a drivetrain between the one or more actuators and the cartridge. Implementations including the one or more actuators can improve the ease at which the user can use the light delivery device to insert the piercing members into the skin of the subject.

Figure 16:
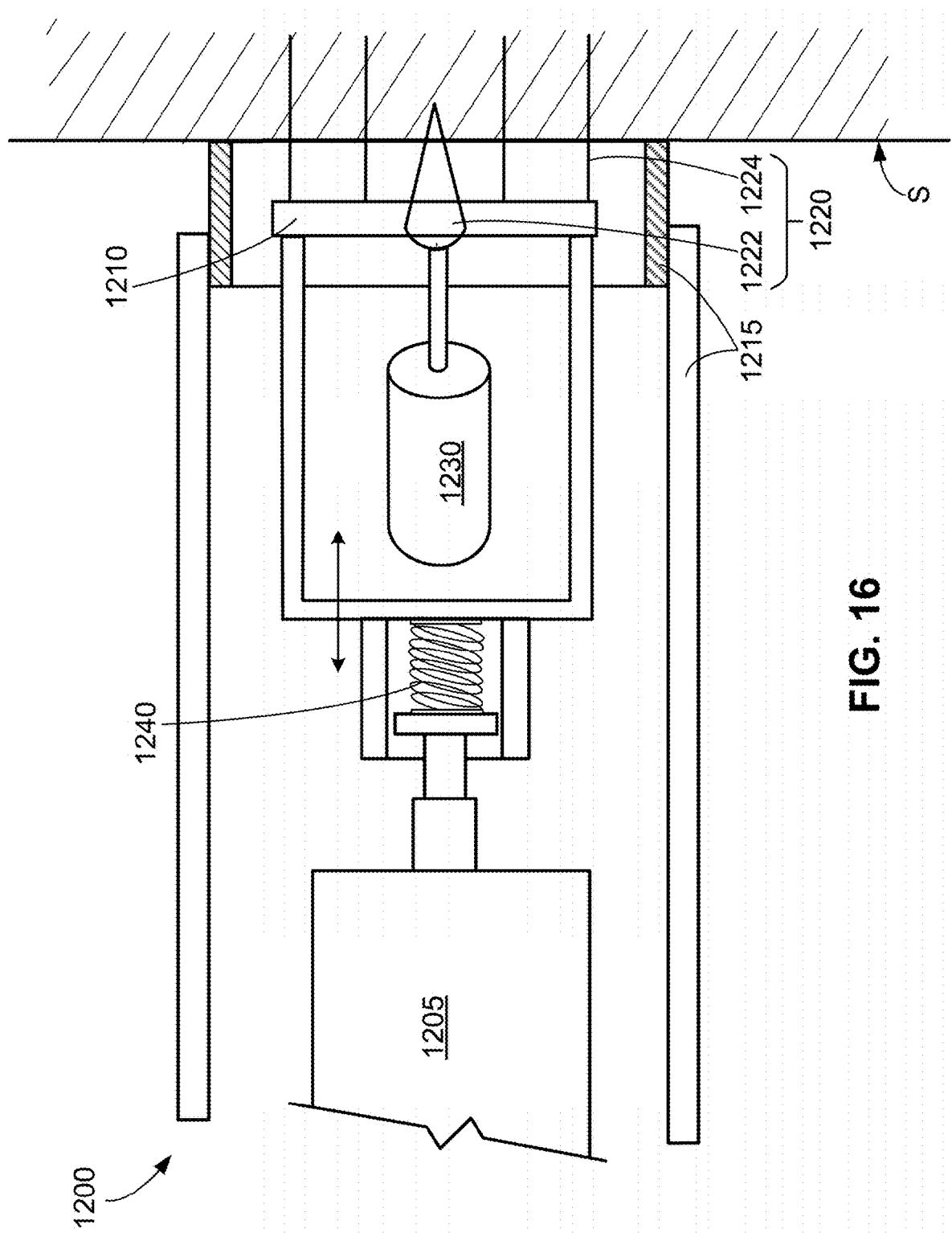
FIGS. 16-19 are schematic side views of additional examples of light delivery devices being used on skin of a subject.

FIG. 16 illustrates an example of a light delivery device 1200 including one or more actuators to move a cartridge of the light delivery device 1200. The light delivery device 1200 differs from the light delivery device 100 in that the light delivery device 1200 includes an actuator 1205 that moves a cartridge 1210 of the light delivery device 1200 relative to a handpiece assembly 1215 of the light delivery device 1200. The actuator 1205 can thus cause insertion of piercing members 1220 into the skin S. In the example of FIG. 14, a light source 1230 is stationary relative to the cartridge 1210 as the actuator 1205 is actuated to move the cartridge 1210. In some implementations, the cartridge 1210 and the actuator 1205 are configured to interact with one another such that optical needles 1222 of the piercing members 1220 and mechanical needles 1224 are inserted into the skin S upon actuation of the actuator 1205.

The light delivery device 1200, e.g., the handpiece assembly 1215 of the light delivery device 1200, can include a return spring 1240 that provides a return force to pull the cartridge 1210 toward the handpiece assembly 1215. For example, the return force pulls the cartridge 1210 to cause the piercing members 1220 to be pulled out of the skin S after the actuator 1205 is released.

Figure 17:
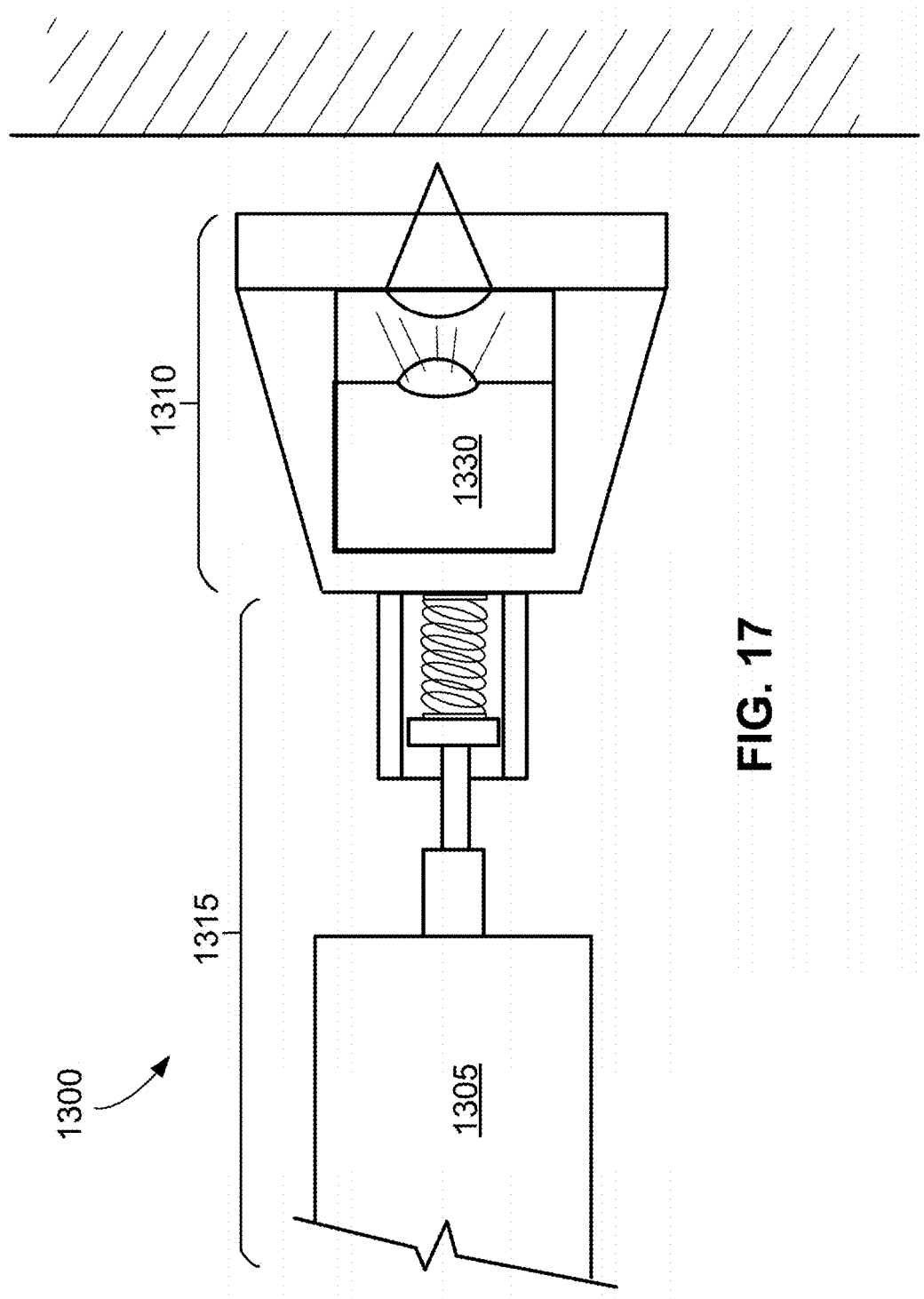

FIG. 17 illustrates another example of a light delivery device 1300. The light delivery device 1300 is similar to the light delivery device 1200 except that a light source 1330 of the light delivery device 1300 is positioned on a cartridge 1310 instead of on a handpiece assembly 1315 of the light delivery device 1300. In the light delivery device 1300, the light source 1330 moves with the cartridge 1310 as the cartridge 1310 is moved by an actuator 1305 of the light delivery device 1300. In this example of the light delivery device 1300, a power source (e.g., an energy storage device) for the light source 1330 can be located on the cartridge 1310 (and be disposable) or can be located on the handpiece assembly 1315 (and be reusable and rechargable).

Figure 18:
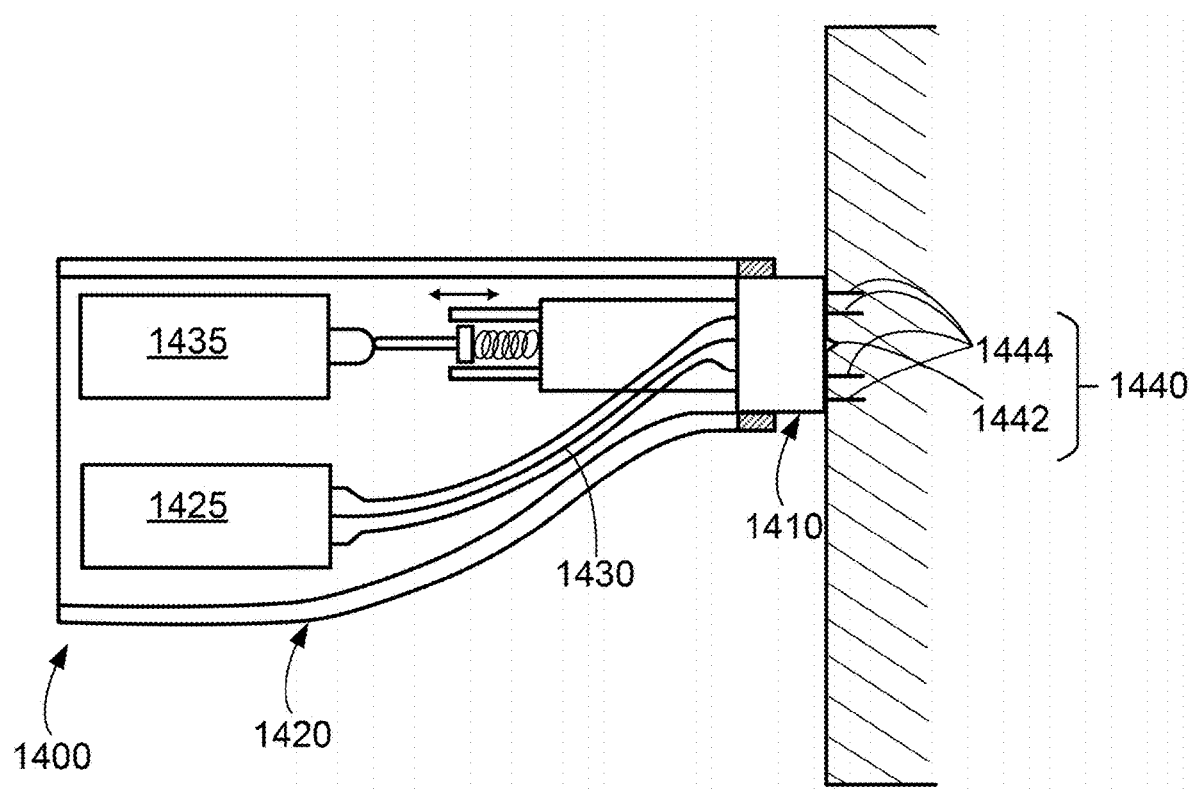

In the examples described with respect to FIGS. 1-12C, light is emitted by the light source through a lens and then through free space into the proximal end of a piercing member. As described in this disclosure, other optical elements can be present in implementations. For example, in the example of a light delivery device 1400 shown in FIG. 18, the light delivery device 1400 includes a cartridge 1410 and a handpiece assembly 1420. The handpiece assembly 1420 includes a light source 1425, an optical fiber 1430, and an actuator 1435 (e.g., similar to the actuator 1205, the actuator 1305, or another actuator described in this disclosure). The cartridge 1410 includes piercing members 1440, including an optical needle 1442 and mechanical needles 1444.

For delivering light to the optical needle 1442, the light source 1425 emits light into the optical fiber 1430, which in turn transmits the light to the optical needle 1442. The cartridge 1410 can include an optical coupling that interfaces with a corresponding optical coupling on the handpiece assembly 1420 and that allows transmission of light from the optical fiber 1430 into the cartridge 1410, thereby allowing light to be transmitted to the optical needle 1442.

Figure 19:
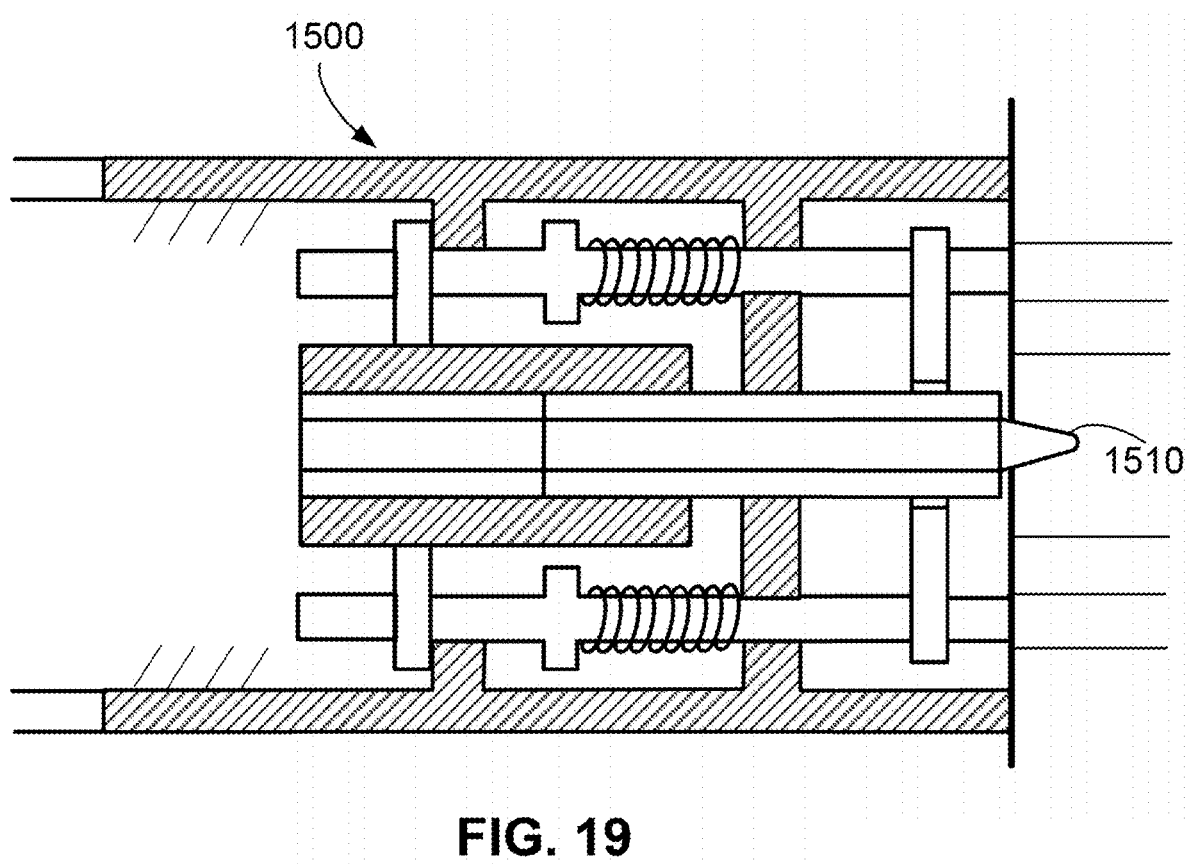

In implementations, the quantity of piercing members—e.g., the quantity of optical needles, the quantity of mechanical needles, or both the quantity of optical needles and the quantity of mechanical needles—can vary. For example, in the example of a light delivery device 1500 shown in FIG. 19, the light delivery device 1500 includes a single optical needle 1510 that is centrally located.

Geometry of the optical needles can vary in implementations. For example, the proximal portion of the optical needle can be cylindrical, prismatic, pyramidal, conical, or another geometric shape that is paired with the distal portion. The distal portion of the optical needle could be beveled on one or both sides to have a sharp edge that will reduce the force needed for insertion into the skin.

In some implementations, the needles may be arranged so that only some of the plurality of needles are piercing, and other needles are non-piercing.

In some implementations, the light delivery device may be equipped without a cartridge. Instead, the needles may be replaceable.

In some implementations, the light delivery device may include piercing and non-piercing members to create a combined treatment methodology. For example, non-piercing members (e.g., spheres, pins or other massaging elements, or other type of elements that deliver the same or different type of energy) may target different depths and treat the skin differently than the piercing members. In further examples, non-piercing members may create stimulation by creating sound waves and/or vibrations using radiofrequency, sound, ultrasound energy. In yet other examples, piercing members and non-piercing members may use any of the previously mentioned stimulation techniques or combine with massaging members or members that add pressure to the skin.

In some implementations, the capacitive sensor may be replaced with or used in combination with mechanical actuators, such as pushbuttons, switches or clips; electronic sensors, such as resistive sensors, such as pressure sensors, force sensors; capacitive sensors such as exposed metal plates or proximity sensors; inductive sensors, such as Hall effect sensors or inductance detectors; optical sensors, such as infrared, color detection sensors, light, ultraviolet sensors, laser sensors or phototransistors, photodiodes; thermal sensors as infrared or thermistors; distance sensors as ultrasonic or laser sensors; humidity sensors implemented with resistive, inductive or capacitive technology; and/or conductance sensors implemented with resistive, inductive or capacitive technology.

In some implementations, the re-use prevention mechanism may include or be replaced with mechanical detection, such as clips and headers; electronic detection without data interchange such as conductive paths; electronic detection with data interchange such as microcontrollers, memory chips or any logic array; and/or field detection technologies such as NFC, RFID, Bluetooth, Infrared, etc.

In some implementations, the re-use prevention mechanism includes an electronically-readable tag positioned on the handpiece assembly 300, and an electronic reader in the cartridge.

In some implementations, the light source may include multiple light sources. For example, the light delivery device might include a separate light source for each penetrating member.

In some examples, a single light source may be configured to deliver light through multiple needles. In some examples, a light source may deliver two different wavelengths into a single penetrating member.

The subject matter and the actions and operations described in this specification (e.g., performed by the controller 510, the control systems 500, 500A, or sub-components of the control systems 500, 500A) can be implemented in digital electronic circuitry, in tangibly-embodied computer software or firmware, in computer hardware, including the structures disclosed in this specification and their structural equivalents, or in combinations of one or more of them. The subject matter and the actions and operations described in this specification can be implemented as or in one or more computer programs, e.g., one or more modules of computer program instructions, encoded on a computer program carrier, for execution by, or to control the operation of, data processing apparatus. The carrier can be a tangible non-transitory computer storage medium. Alternatively or in addition, the carrier can be an artificially-generated propagated signal, e.g., a machine-generated electrical, optical, or electromagnetic signal that is generated to encode information for transmission to suitable receiver apparatus for execution by a data processing apparatus. The computer storage medium can be or be part of a machine-readable storage device, a machine-readable storage substrate, a random or serial access memory device, or a combination of one or more of them. A computer storage medium is not a propagated signal.

The term "data processing apparatus" encompasses all kinds of apparatus, devices, and machines for processing data, including by way of example a programmable processor, a computer, or multiple processors or computers. Data processing apparatus can include special-purpose logic circuitry, e.g., an FPGA (field programmable gate array), an ASIC (application-specific integrated circuit), or a GPU (graphics processing unit). The apparatus can also include, in addition to hardware, code that creates an execution environment for computer programs, e.g., code that constitutes processor firmware, a protocol stack, a database management system, an operating system, or a combination of one or more of them.

A computer program can be written in any form of programming language, including compiled or interpreted languages, or declarative or procedural languages; and it can be deployed in any form, including as a stand-alone program, e.g., as an app, or as a module, component, engine, subroutine, or other unit suitable for executing in a computing environment, which environment may include one or more computers interconnected by a data communication network in one or more locations.

The processes and logic flows described in this specification can be performed by one or more computers executing one or more computer programs to perform operations by operating on input data and generating output. The processes and logic flows can also be performed by special-purpose logic circuitry, e.g., an FPGA, an ASIC, or a GPU, or by a combination of special-purpose logic circuitry and one or more programmed computers.

Computers suitable for the execution of a computer program can be based on general or special-purpose microprocessors or both, or any other kind of central processing unit. Generally, a central processing unit will receive instructions and data from a read-only memory or a random access memory or both. The essential elements of a computer are a central processing unit for executing instructions and one or more memory devices for storing instructions and data. The central processing unit and the memory can be supplemented by, or incorporated in, special-purpose logic circuitry.

Generally, a computer will also include, or be operatively coupled to, one or more mass storage devices, and be configured to receive data from or transfer data to the mass storage devices. The mass storage devices can be, for example, magnetic, magneto-optical, or optical disks, or solid state drives. However, a computer need not have such devices.

This specification uses the term "configured to" in connection with systems, apparatus, and computer program components. That a system of one or more computers is configured to perform particular operations or actions means that the system has installed on it software, firmware, hardware, or a combination of them that in operation cause the system to perform the operations or actions. That one or more computer programs is configured to perform particular operations or actions means that the one or more programs include instructions that, when executed by data processing apparatus, cause the apparatus to perform the operations or actions. That special-purpose logic circuitry is configured to perform particular operations or actions means that the circuitry has electronic logic that performs the operations or actions.

Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially be claimed as such, one or more features from a claimed combination can in some cases be excised from the combination, and the claim may be directed to a subcombination or variation of a subcombination.

While operations are depicted in the drawings and recited in the claims in a particular order, this by itself should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the implementations described above should not be understood as requiring such separation in all implementations, and it should be understood that the described program components and systems can generally be integrated together in a single software product or packaged into multiple software products. Furthermore, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

Accordingly, other implementations are within the scope of the claims.

What is claimed:

1. A light delivery device for delivering light therapy to skin of a subject, the light delivery device comprising:
   a light source configured to emit light, the light source comprising a first light emitter and a second light emitter; and
   a plurality of first piercing members extending from a distal surface of the light delivery device, the plurality of first piercing members being light-transmissive and being configured to be inserted into a subdermal or intradermal portion of the skin of the subject as the distal surface is placed against the skin of the subject,
   a first lens positioned between the light source and a first piercing member of the plurality of first piercing members, the first lens spaced from the plurality of first piercing members;
   a second lens positioned between the light source and a second piercing member of the plurality of first piercing members;
   wherein the plurality of first piercing members are configured to, when inserted into the skin of the subject, deliver the light to the subdermal or intradermal portion of the skin of the subject.

2. The light delivery device of claim 1, comprising a cartridge comprising the plurality of first piercing members.

3. The light delivery device of claim 2, wherein the cartridge comprises:
   a needle holder to which the plurality of first piercing members are attached, the needle holder configured to align the plurality of first piercing members relative to the light emitted by the light source.

4. The light delivery device of claim 3, comprising:
   an optical transmission system for transmitting the light emitted by the light source to the plurality of first piercing members, wherein the needle holder is configured to align the plurality of first piercing members relative to the optical transmission system.

5. The light delivery device of claim 2, wherein the cartridge comprises one or more second piercing members extending from a distal surface of the cartridge, wherein the one or more second piercing members are configured to be inserted into the subdermal or intradermal portion of the skin of the subject as the cartridge is placed against the skin of the subject.

6. The light delivery device of claim 5, wherein a width of an insertable portion of each piercing member of the one or more second piercing members is between 0.001 millimeters and 3 millimeters.

7. The light delivery device of claim 1, wherein a width of an insertable portion of each piercing member of the plurality of first piercing members is in a range of approximately 0.03 millimeters to approximately 2 millimeters.

8. The light delivery device of claim 1, comprising:
an optical transmission system for transmitting the light emitted by the light source to the plurality of first piercing members, wherein the optical transmission system comprises at least one optical element selected from the group consisting of: a fiber optic cable, a waveguide, or an optical diffuser.

9. The light delivery device of claim 1, wherein the second lens is spaced from the second piercing member of the plurality of first piercing members.

10. The light delivery device of claim 1, wherein a wavelength of the light emitted by the light source is in a range of approximately 280 nanometers to approximately 3000 nanometers.

11. The light delivery device of claim 1, wherein the light delivery device is configured such that a power of a portion of light delivered by each piercing member of the plurality of first piercing members is at least 1 mW.

12. The light delivery device of claim 1, wherein each piercing member of the plurality of first piercing members is configured to be inserted to a depth in a range of approximately 0.001 millimeters to approximately 3 millimeters relative to a surface of the skin.

13. The light delivery device of claim 1, wherein each piercing member of the plurality of first piercing members is configured to be inserted to a depth of at least 0.1 millimeters relative to a surface of the skin.

14. The light delivery device of claim 1, wherein the plurality of first piercing members are configured to, when inserted into the skin of the subject, deliver at least a portion of the light bypassing the melanin layer of the skin.

15. The light delivery device of claim 1, wherein a quantity of the plurality of first piercing members is between 1 and 50.

16. The light delivery device of claim 1, comprising:
one or more contact sensors configured to detect contact between the distal surface of the light delivery device and the skin of the subject.

17. The light delivery device of claim 16, wherein the one or more contact sensors comprises:
at least three contact sensors configured to detect contact between the distal surface of the light delivery device and the skin.

18. The light delivery device of claim 17, comprising:
a status indicator responsive to a signal generated by the one or more contact sensors.

19. The light delivery device of claim 18, wherein the status indicator communicates a direction for tilting the device to achieve a desired alignment.

20. The light delivery device of claim 16, wherein the one or more contact sensors comprises a capacitive sensor.

21. The light delivery device of claim 1, further comprising:
a cartridge comprising the plurality of first piercing members; and
a handpiece assembly, wherein the cartridge is configured to be mounted to the handpiece assembly.

22. The light delivery device of claim 21, comprising:
a cartridge sensor configured to detect whether the cartridge is mounted to the handpiece assembly.

23. The light delivery device of claim 22, comprising:
one or more processors configured to prevent initiation of emission of the light by the light source in response to the cartridge sensor detecting that the cartridge is not mounted to the handpiece assembly.

24. The light delivery device of claim 21, comprising:
one or more processors configured to prevent initiation of emission of the light by the light source in response to a contact sensor detecting that the cartridge is not perpendicular relative to the skin of the subject.

25. The light delivery device of claim 21, comprising:
a re-use prevention mechanism for preventing the cartridge from being coupled to the handpiece assembly after the cartridge is removed from the handpiece assembly.

26. The light delivery device of claim 1, further comprising:
a handpiece assembly, wherein the plurality of first piercing members are integral to the handpiece assembly.

27. The light delivery device of claim 1, further comprising:
an actuator to initiate emission of the light by the light source.

28. The light delivery device of claim 1, further comprising:
a cartridge comprising the plurality of first piercing members, wherein the cartridge comprises a conformable layer defining at least part of the distal surface of the cartridge.

29. The light delivery device of claim 1, wherein the light delivered to the subdermal or intradermal portion of the skin of the subject is configured to promote hair growth and/or inhibit hair loss.

30. A cartridge mountable to a light delivery device comprising a light source having a first light emitter and a second light emitter for delivering light therapy to skin of a subject, wherein the cartridge comprises:
a housing mountable to the light delivery device;
a plurality of first piercing members attached to the housing, the plurality of first piercing members extending from a distal surface of the cartridge, the plurality of first piercing members being light-transmissive; and
a first lens configured to be positioned between the light source and a first piercing member of the plurality of first piercing members, the first lens spaced from the plurality of first piercing members,
a second lens configured to be positioned between the light source and a second piercing member of the plurality of first piercing members;
wherein the plurality of first piercing members are configured to be inserted into a subdermal or intradermal portion of the skin of the subject as the cartridge is placed against the skin of the subject, and
wherein the plurality of first piercing members are configured to, when the cartridge is mounted to the light delivery device and when the plurality of first piercing members are inserted into the skin of the subject, deliver light emitted by the light delivery device to the subdermal or intradermal portion of the skin of the subject.

* * * * *